US010696982B2

(12) United States Patent
Bramlett et al.

(10) Patent No.: US 10,696,982 B2
(45) Date of Patent: Jun. 30, 2020

(54) COMPOSITIONS AND METHODS FOR CONTROLLING PLANT PESTS

(71) Applicant: Syngenta Participations AG, Basel (CH)

(72) Inventors: Matthew Richard Bramlett, Gent-Zwijnaarde (BE); Katherine Seguin, Research Triangle Park, NC (US); Mark Scott Rose, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 40 days.

(21) Appl. No.: 15/736,192

(22) PCT Filed: Jun. 23, 2016

(86) PCT No.: PCT/US2016/038947
§ 371 (c)(1),
(2) Date: Dec. 13, 2017

(87) PCT Pub. No.: WO2017/003811
PCT Pub. Date: Jan. 5, 2017

(65) Prior Publication Data

US 2019/0177377 A1 Jun. 13, 2019

Related U.S. Application Data

(60) Provisional application No. 62/187,468, filed on Jul. 1, 2015.

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01)

(58) Field of Classification Search
CPC .......................... C12N 15/8286; C07K 14/325
See application file for complete search history.

(56) References Cited

U.S. PATENT DOCUMENTS

2009/0041869 A1 2/2009 Cosgrove

FOREIGN PATENT DOCUMENTS

| | | | | |
|---|---|---|---|---|
| CN | 101926365 | A | * | 12/2010 |
| CN | 101926365 | A | | 12/2010 |
| WO | 2011/075590 | A1 | | 6/2011 |
| WO | 2013/134734 | A2 | | 9/2013 |

OTHER PUBLICATIONS

De Maagd, Ruud A., et al. "Identification of Bacillus thuringiensisdelta-endotoxin Cry1C domain III amino acid residues involved in insect specificity." Appl. Environ. Microbiol. 65.10 (1999): 4369-4374 (Year: 1999).*

Aronson, Arthur I., and Yechiel Shai. "Why Bacillus thuringiensis insecticidal toxins are so effective: unique features of their mode of action." FEMS Microbiology Letters195.1 (2001): 1-8 (Year: 2001).*

Gryson, Nicolas, et al. "Detection of DNA during the refining of soybean oil." Journal of the American Oil Chemists' Society79.2 (2002): 171-174. (Year: 2002).*

Tounsi, S., N. Zouari, and S. Jaoua. "Cloning and study of the expression of a novel cry1Ia-type gene from *Bacillus thuringiensis* subsp. *kurstaki*." Journal of applied microbiology95.1 (2003): 23-28 (Year: 2003).*

Tan, S. Y., et al. "Comparative susceptibility of Ostrinia furnacalis, Ostrinia nubilalis and Diatraea saccharalis (Lepidoptera: Crambidae) to Bacillus thuringiensis Cry1 toxins." Crop protection 30.9 (2011): 1184-1189. (Year: 2011).*

Tan, S. Y., et al. "Comparative susceptibility of Ostrinia furnacalis, Ostrinia nubilalis and Diatraea saccharalis (Lepidoptera: Crambidae) to Bacillus thuringiensis Cry1 toxins." Crop protection;30.9 (2011): 1184-1189. (Year: 2011).*

International Search Report mailed in International Application No. PCT/US2016/038947 filed Jun. 23, 2016 dated Dec. 7, 2016.

Kuo et al., "Identification of novel cry-type genes from Bacillus thuringiensis strains on the basis of restriction fragment length polymorphism of the PCR-amplified DNA", Applied and Enviormental Microbiology, Apr. 1996, vol. 62, No. 4, pp. 1369-1377.

* cited by examiner

*Primary Examiner* — Lee A Visone
(74) *Attorney, Agent, or Firm* — Gregory W. Warren

(57) ABSTRACT

Novel insecticidal proteins that are toxic to lepidopteran pests are disclosed. The DNA encoding the insecticidal proteins can be used to transform prokaryotic and eukaryotic organisms to express the insecticidal proteins. The recombinant organisms or compositions containing the recombinant organisms or the insecticidal proteins alone or in combination with an appropriate agricultural carrier can be used to control lepidopteran pests in various environments.

3 Claims, No Drawings

Specification includes a Sequence Listing.

COMPOSITIONS AND METHODS FOR CONTROLLING PLANT PESTS

REFERENCE TO SEQUENCE LISTING SUBMITTED ELECTRONICALLY

The official copy of the sequence listing is submitted electronically via EFS-Web as an ASCII formatted sequence listing with a file named "80829-US-REG-ORG-P-1_SeqList_ST25.txt", created on Jul. 9, 2018, and having a size of 329 kilobytes and is filed concurrently with the specification. The sequence listing contained in this ASCII formatted document is part of the specification and is herein incorporated by reference in its entirety.

RELATED APPLICATION INFORMATION

This application is a 371 of International Application No. PCT/US2016/038947, filed Jun. 23, 2016, which claims priority to U.S. Provisional Application No. 62/187,468, filed Jul. 1, 2015, the contents of which are incorporated herein by reference herein.

FIELD OF THE INVENTION

This invention relates to pesticidal proteins and the nucleic acid molecules that encode them, as well as compositions and methods for controlling plant pests.

BACKGROUND

*Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions comprising *Bacillus thuringiensis* strains or their insecticidal proteins can be used as environmentally-acceptable insecticides to control agricultural insect pests or insect vectors of a variety of human or animal diseases.

Crystal (Cry) proteins from *Bacillus thuringiensis* have potent insecticidal activity against predominantly lepidopteran, dipteran, and coleopteran pest insects. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus Thuringiensis* family tree. In Advanced Engineered Pesticides. Marcel Dekker, Inc., New York, N.Y.). These proteins were originally classified as CryI to CryVI based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as CryIA, CryIB, CryIC, etc. Even more closely related proteins within each division were given names such as CryIC(a), CryIC(b), etc. The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each toxin is assigned a unique name incorporating a primary rank (an Arabic number), a secondary rank (an uppercase letter), a tertiary rank (a lowercase letter), and a quaternary rank (another Arabic number). In the current classification, Roman numerals have been exchanged for Arabic numerals in the primary rank. For example, "CryIA(a)" under the older nomenclature is now "Cry1Aa" under the current nomenclature. According to Ibrahim et al. (2010, Bioeng. Bugs, 1:31-50), the Cry toxins can still be separated into six major classes according to their insect host specificities and include: Group 1—lepidopteran e.g., Cry1, Cry9 and Cry15); group 2—lepidopteran and dipteran (e.g., Cry2); group 3—coleopteran (Cry3, Cry7 and Cry8); group 4—dipteran (Cry4, Cry10, Cry11, Cry16, Cry17, Cry19 and Cry20); group 5-lepidopteran and coleopteran (Cry1I); and group 6-nematodes (Cry6). The Cry1I, Cry2, Cry3, Cry10 and Cry11 toxins (73-82 kDa) are unique because they appear to be natural truncations of the larger Cry1 and Cry4 proteins (130-140 kDa).

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for many of the lepidopteran-active Cry proteins, such as Cry1 and Cry9, and 60-80 kDa for the coleopteran-active Cry3 proteins and the lepidopteran/dipteran-active Cry2 proteins. After the crystals are solubilized by a susceptible insect the released protoxins are processed by proteases in the insect gut, for example trypsin and chymotrypsin, to produce a protease-resistant core Cry protein toxin. This proteolytic processing involves the removal of amino acids from different regions of the various Cry protoxins. For example, Cry protoxins that are 130-140 kDa are typically activated through the proteolytic removal of an N-terminal peptide of 25-30 amino acids and approximately half of the remaining protein from the C-terminus resulting in an approximately 60-70 kDa mature Cry toxin. The protoxins that are 60-80 kDa, e.g. Cry2 and Cry3, are also processed but not to the same extent as the larger protoxins. The smaller protoxins typically have equal or more amino acids removed from the N-terminus than the larger protoxins but less amino acids removed from the C-terminus. For example, proteolytic activation of Cry2 family members typically involves the removal of approximately 40-50 N-terminal amino acids. Many of the Cry proteins are quite toxic to specific target insects, but many have narrow spectrums of activity.

Cry proteins generally have five conserved sequence domains, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain III typically consists of two antiparallel beta-sheets in 'jelly-roll' formation (de Maagd et al., 2001, supra). Domains II and III are involved in receptor recognition and binding, and are therefore considered determinants of toxin specificity.

Numerous commercially valuable plants, including common agricultural crops, are susceptible to attack by plant pests including insect and nematode pests, causing substantial reductions in crop yield and quality. For example, plant pests are a major factor in the loss of the world's important agricultural crops. About $8 billion are lost every year in the United States alone due to infestations of invertebrate pests including insects. Insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or compliment to chemical pesticides. The genes coding for some of these Cry proteins have been isolated and their expression in heterologous hosts such as transgenic plants have been shown to provide another tool for the control of economically important insect pests.

Good insect control can thus be reached, but certain chemicals can sometimes also affect non-target beneficial insects and certain biologicals have a very narrow spectrum of activity. In addition, the continued use of certain chemical and biological control methods heightens the chance for insect pests to develop resistance to such control measures. This has been partially alleviated by various resistance management practices, but there remains a need to develop new and effective pest control agents that provide an economic benefit to farmers and that are environmentally acceptable. Particularly needed are control agents that can target to a wider spectrum of economically important insect pests and that efficiently control insect strains that are or could become resistant to existing insect control agents.

SUMMARY

In view of these needs, it is an object of the present invention to provide new pest control agents by providing new *Bacillus thuringiensis* (Bt) isolates as well as novel genes and pesticidal proteins that may be used to control a variety of plant pests.

The invention provides compositions and methods for conferring pesticidal activity to bacteria, plants, plant cells, tissues and seeds. In particular, chimeric genes comprising novel polynucleotides that encode Cry proteins isolated from Bt and sequences substantially identical thereto, whose expression results in proteins with toxicity to economically important insect pests, particularly insect pests that infest plants, are provided. The invention is further drawn to the novel Cry proteins resulting from the expression of the polynucleotides, and to compositions and formulations containing the Cry proteins, which are toxic to insects by inhibiting the ability of insect pests to survive, grow and reproduce, or of limiting insect-related damage or loss to crop plants. Cry proteins of the invention include native Cry proteins and mutant or variant Cry proteins that have one or more amino acid substitutions, additions or deletions. Examples of mutant Cry proteins include without limitation those that are mutated to have a broader spectrum of activity or higher specific activity than their native Cry protein counterparts, those mutated to introduce an epitope to generate antibodies that differentially recognize the mutated protein from the native protein or those mutated to modulate expression in a transgenic organism. The novel Cry proteins of the invention are highly toxic to insect pests. For example, the Cry proteins of the invention can be used to control one or more economically important insect pests such as black cutworm (*Agrotis ipsilon*), European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and the like.

The invention also provides synthetic polynucleotides that encode the Cry proteins of the invention that have one or more codons optimized for expression in transgenic organisms such as transgenic bacteria or transgenic plants.

The invention is further drawn to expression cassettes and recombinant vectors comprising a polynucleotide that encodes a Cry protein of the invention. The invention also provides transformed bacteria, plants, plant cells, tissues, and seeds comprising a chimeric gene, or an expression cassette or a recombinant vector which are useful in expressing a Cry protein of the invention in the transformed bacteria, plants, plant cells, tissues and seeds.

The invention is also drawn to isolated *Bacillus thuringiensis* (Bt) strains that produce the Cry proteins of the invention. Such Bt strains may be a naturally occurring isolate or a transgenic Bt strain which produce one or more of the Cry proteins of the invention.

The invention is also drawn to methods of using the polynucleotides, for example in DNA constructs or chimeric genes or expression cassettes or recombinant vectors for transformation and expression in organisms, including plants and microorganisms, such as bacteria. The nucleotide or amino acid sequences may be native or synthetic sequences that have been designed for expression in an organism such as a plant or bacteria or in making hybrid Cry toxins with enhanced pesticidal activity. The invention is further drawn to methods of making the Cry proteins and to methods of using the polynucleotide sequences and Cry proteins, for example in microorganisms to control insects or in transgenic plants to confer protection from insect damage.

Another aspect of the invention includes insecticidal compositions and formulations comprising the Cry proteins or *Bacillus thuringiensis* strains of the invention, and methods of using the compositions or formulations to control insect populations, for example by applying the compositions or formulations to insect-infested areas, or to prophylactically treat insect-susceptible areas or plants to confer protection against the insect pests. Optionally, the compositions or formulations of the invention may, in addition to the Cry protein or Bt strain of the invention, comprises other pesticidal agents such as chemical pesticides in order to augment or enhance the insect-controlling capability of the composition or formulation.

The compositions and methods of the invention are useful for controlling insect pests that attack plants, particularly crop plants. The compositions of the invention are also useful for generating altered or improved Cry proteins that have pesticidal activity, or for detecting the presence of a Cry protein or nucleic acids in commercial products or transgenic organisms.

These and other features, aspects, and advantages of the invention will become better understood with reference to the following detailed description and claims.

BRIEF DESCRIPTION OF THE SEQUENCES IN THE SEQUENCE LISTING

SEQ ID NO:1 is a nucleotide sequence encoding a BT-0001 protein.

SEQ ID NO:2 is a nucleotide sequence encoding a BT-0003 protein.

SEQ ID NO:3 is a nucleotide sequence encoding a BT-0020 protein.

SEQ ID NO:4 is a nucleotide sequence encoding a BT-0022 protein.

SEQ ID NO:5 is a nucleotide sequence encoding a BT-0027 protein.

SEQ ID NO:6 is a nucleotide sequence encoding a BT-0029 protein.

SEQ ID NO:7 is a nucleotide sequence encoding a BT-0030 protein.

SEQ ID NO:8 is a nucleotide sequence encoding a BT-0031 protein.

SEQ ID NO:9 is a nucleotide sequence encoding a BT-0201 protein.

SEQ ID NO: 10 is a nucleotide sequence encoding a BT-0202 protein.

SEQ ID NO: 1 is a codon optimized sequence encoding a BT-0001 protein.

SEQ ID NO: 12 is a codon optimized sequence encoding a BT-0003 protein.

SEQ ID NO: 13 is a codon optimized sequence encoding a BT-0020 protein.

SEQ ID NO: 14 is a codon optimized sequence encoding a BT-0022 protein.

SEQ ID NO: 15 is a codon optimized sequence encoding a BT-0027 protein.

SEQ ID NO: 16 is a codon optimized sequence encoding a BT-0029 protein.

SEQ ID NO: 17 is a codon optimized sequence encoding a BT-0030 protein.

SEQ ID NO:18 is a codon optimized sequence encoding a BT-0031 protein.

SEQ ID NO:19 is a codon optimized sequence encoding a BT-0201 protein.

SEQ ID NO:20 is a codon optimized sequence encoding a BT-0202 protein.

SEQ ID NO:21 is a nucleotide sequence encoding a mutant BT-0001 protein.

SEQ ID NO:22 is a nucleotide sequence encoding a mutant BT-0003 protein.

SEQ ID NO:23 is a nucleotide sequence encoding a mutant BT-0020 protein.

SEQ ID NO:24 is a nucleotide sequence encoding a mutant BT-0022 protein.

SEQ ID NO:25 is a nucleotide sequence encoding a mutant BT-0027 protein.

SEQ ID NO:26 is a nucleotide sequence encoding a mutant BT-0029 protein.

SEQ ID NO:27 is a nucleotide sequence encoding a mutant BT-0030 protein.

SEQ ID NO:28 is a nucleotide sequence encoding a mutant BT-0031 protein.

SEQ ID NO:29 is a nucleotide sequence encoding a mutant BT-0201 protein.

SEQ ID NO:30 is a nucleotide sequence encoding a mutant BT-0202 protein.

SEQ ID NO:31 is an amino acid sequence of a BT-0001 protein.

SEQ ID NO:32 is an amino acid sequence of a BT-0003 protein.

SEQ ID NO:33 is an amino acid sequence of a BT-0020 protein.

SEQ ID NO:34 is an amino acid sequence of a BT-0022 protein.

SEQ ID NO:35 is an amino acid sequence of a BT-0027 protein.

SEQ ID NO:36 is an amino acid sequence of a BT-0029 protein.

SEQ ID NO:37 is an amino acid sequence of a BT-0030 protein.

SEQ ID NO:38 is an amino acid sequence of a BT-0031 protein.

SEQ ID NO:39 is an amino acid sequence of a BT-0201 protein.

SEQ ID NO:40 is an amino acid sequence of a BT-0202 protein.

SEQ ID NO:41 is an amino acid sequence of a mutant BT-0001 protein.

SEQ ID NO:42 is an amino acid sequence of a mutant BT-0003 protein.

SEQ ID NO:43 is an amino acid sequence of a mutant BT-0020 protein.

SEQ ID NO:44 is an amino acid sequence of a mutant BT-0022 protein

SEQ ID NO:45 is an amino acid sequence of a mutant BT-0027 protein.

SEQ ID NO:46 is an amino acid sequence of a mutant BT-0029 protein.

SEQ ID NO:47 is an amino acid sequence of a mutant BT-0030 protein.

SEQ ID NO:48 is an amino acid sequence of a mutant BT-0031 protein.

SEQ ID NO:49 is an amino acid sequence of a mutant BT-0201 protein

SEQ ID NO:50 is an amino acid sequence of a mutant BT-0202 protein.

SEQ ID NO:51 is an amino acid sequence of a Cry1Ah1 protein.

SEQ ID NO:52 is an amino acid sequence of a Cry1Aa1 protein.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Definitions

As used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

By "activity" of a toxic Cry protein of the invention is meant that the toxic protein functions as an orally active insect control agent, has a toxic effect, or is able to disrupt or deter insect feeding, which may or may not cause death of the insect. When a toxic protein of the invention is delivered to the insect, the result is typically death of the insect, or the insect does not feed upon the source that makes the toxic protein available to the insect.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of variant or homolog Cry proteins are aligned with each other, the amino acids that "correspond to" certain enumerated positions in the variant or homolog protein are those that align with these positions in a reference protein but that are not necessarily in these exact numerical positions relative to the particular reference amino acid sequence of the invention. For example, if SEQ ID NO:31 is the reference sequence and is aligned with SEQ ID NO:32, the Ser629 of SEQ ID NO:32 "corresponds to" Ser630 of SEQ ID NO:31.

As used herein, the term "Cry protein" means an insecticidal protein of a *Bacillus thuringiensis* crystal delta-endotoxin type. The term "Cry protein" can refer to the protoxin form or any insecticidally active fragment or toxin thereof.

To "deliver" a composition or toxic protein means that the composition or toxic protein comes in contact with an insect, which facilitates the oral ingestion of the composition or toxic protein, resulting in a toxic effect and control of the insect. The composition or toxic protein can be delivered in many recognized ways, including but not limited to, transgenic plant expression, formulated protein composition(s), sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of a toxic protein that inhibits, through a toxic effect, the ability of insects to survive, grow, feed or reproduce, or limits insect-related damage or loss in crop plants or protects the yield potential of a crop when grown in the presence of insect pests. "Effective insect-controlling amount" may or may not mean killing the insects, although it preferably means killing the insects.

"Expression cassette" as used herein means a nucleic acid molecule capable of directing expression of at least one polynucleotide of interest, such as a polynucleotide that encodes a Cry protein of the invention, in an appropriate host cell, comprising a promoter operably linked to the polynucleotide of interest which is operably linked to a termination signal. An "expression cassette" also typically comprises additional polynucleotides required for proper translation of the polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

A "gut protease" is a protease naturally found in the digestive tract of an insect. This protease is usually involved in the digestion of ingested proteins. Examples of gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y).

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Homologous recombination" is the exchange ("crossing over") of DNA fragments between two DNA molecules or chromatids of paired chromosomes in a region of identical polynucleotides. A "recombination event" is herein understood to mean a meiotic crossing-over.

A nucleic acid sequence is "isocoding" with a reference nucleic acid sequence when the nucleic acid sequence encodes a polypeptide having the same amino acid sequence as the polypeptide encoded by the reference nucleic acid sequence. For example, SEQ ID NO:11 is isocoding with SEQ ID NO: 1 because they both encode the amino acid sequence represented by SEQ ID NO:31.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant.

A "nucleic acid molecule" is single- or double-stranded DNA or RNA that can be isolated from any source. In the context of the present invention, the nucleic acid molecule is preferably a segment of DNA.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

As used herein "pesticidal," insecticidal," and the like, refer to the ability of a Cry protein of the invention to control a pest organism or an amount of a Cry protein that can control a pest organism as defined herein. Thus, a pesticidal Cry protein can kill or inhibit the ability of a pest organism (e.g., insect pest) to survive, grow, feed, or reproduce.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"Polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of commercially valuable enzymes or metabolites or altered reproductive capability.

The term "promoter" refers to a polynucleotide, usually upstream (5') of its coding polynucleotide, which controls the expression of the coding polynucleotide by providing the recognition for RNA polymerase and other factors required for proper transcription.

A "protoplast" is an isolated plant cell without a cell wall or with only parts of the cell wall.

As used herein, the term "recombinant" refers to a form of nucleic acid (e.g., DNA or RNA) or protein or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule incorporated into its genome. As a result of such genomic alteration, the recombinant plant is distinctly different from the related wild-type plant.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

The term "identity" or "identical" or "substantially identical," in the context of two nucleic acid or amino acid sequences, refers to two or more sequences or subsequences that have at least 60%, preferably at least 80%, more preferably 90%, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues or bases in length, more preferably over a region of at least about 100 residues or bases, and most preferably the sequences are substantially identical over at least about 150 residues or bases. In an especially preferred embodiment, the sequences are substantially identical over the entire length of the coding regions. Furthermore, substantially identical nucleic acid or amino acid sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, Md. 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising bases or structural features that are not present in the natural sequence. For example, an artificial sequence encoding a Cry protein of the invention that resembles more closely the G+C content and the normal codon distribution of dicot or monocot plant genes is said to be synthetic.

As used herein, a Cry protein that is "toxic" to an insect pest is meant that the Cry protein functions as an orally active insect control agent to kill the insect pest, or the Cry protein is able to disrupt or deter insect feeding, or causes growth inhibition to the insect pest, both of which may or may not cause death of the insect. When a Cry protein of the invention is delivered to an insect or an insect comes into oral contact with the Cry protein, the result is typically death of the insect, or the insect's growth is slowed, or the insect stops feeding upon the source that makes the toxic Cry protein available to the insect.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

This invention provides compositions and methods for controlling harmful plant pests. Particularly, the invention relates to Cry proteins that may be isolated from bacteria, such as *Bacillus thuringiensis*, that are toxic to insect pests and to polynucleotides that comprise nucleotide sequences that encode the Cry proteins, and to the making and using of the polynucleotides and Cry proteins to control insect pests.

According to some embodiments, the invention provides a nucleic acid molecule or optionally an isolated nucleic acid molecule comprising a nucleotide sequence encoding a Cry protein in its protoxin form or a biologically active or toxin fragment thereof, wherein the nucleotide sequence (a) has at least 80% to at least 99% sequence identity with any of SEQ ID NOs:1-10 or a toxin-encoding fragment thereof; or (b) encodes a protein comprising an amino acid sequence that has at least 80% to at least 99% sequence identity with any of SEQ ID NOs:31-40 or an toxin fragment thereof; or (c) is a synthetic sequence of (a) or (b) that has codons optimized for expression in a transgenic organism. In other embodiments, the nucleotide sequence comprises any of SEQ ID NOs:1-10 or any toxin-encoding fragments of any of SEQ ID NOs:1-10. In other embodiments, the synthetic nucleotide sequence comprises any of SEQ ID NOs:11-30 or any toxin-encoding fragments of any of SEQ ID NOs: 11-30.

Polynucleotides that are fragments of Cry protein protoxin-encoding polynucleotides are also encompassed by the invention. By "fragment" is intended a portion of the nucleotide sequence encoding a Cry protein. A fragment of a nucleotide sequence may encode a biologically active portion of a Cry protein, the so called "toxin fragment," or it may be a fragment that can be used as a hybridization probe or PCR primer using methods disclosed below. Nucleic acid molecules that are fragments of a Cry protein encoding nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450 contiguous nucleotides, or up to the number of nucleotides present in a full-length Cry protein encoding nucleotide sequence disclosed herein (for example, 3546 nucleotides for SEQ ID NO: 1) depending upon the intended use. By "contiguous" nucleotides is intended nucleotide residues that are immediately adjacent to one another. Some fragments of the nucleotide sequences of the invention will encode toxin fragments that retain the biological activity of the Cry protein and, hence, retain insecticidal activity. By "retains insecticidal activity" is intended that the fragment will have at least about 30%, preferably at least about 50%, more preferably at least about 70%, even more preferably at least about 80% of the insecticidal activity of the Cry protein. Methods for measuring insecticidal activity are well known in the art. See, for example, Czapla and Lang (1990) J. Econ. Entomol. 83:2480-2485; Andrews et al. (1988) Biochem. J. 252:199-206; Marrone et al. (1985) J. of Economic Entomology 78:290-293; and U.S. Pat. No. 5,743,477, all of which are herein incorporated by reference in their entirety.

A toxin fragment of a Cry protein of the invention will encode at least about 15, 25, 30, 50, 75, 100, 125, 150, 175, 200, 250, 300, 350, 400, and 450 contiguous amino acids, or up to the total number of amino acids present in a full-length Cry protein of the invention (for example, 1181 amino acids for SEQ ID NO:31).

In some embodiments, a nucleic acid molecule of the invention comprises, consists essentially of or consists of a nucleotide sequence encoding a Cry protein comprising an amino acid sequence that has at least 80% to at least 99% sequence identity with any of SEQ ID NOs:31-40 or a toxin fragment thereof. In some other embodiments, the amino acid sequence comprises, consists essentially of or consists of any of SEQ ID NOs:31-40 or a toxin fragment thereof. Thus, in some embodiments, Cry proteins which have been activated by means of proteolytic processing, for example, by proteases prepared from the gut of an insect, may be characterized and the N-terminal or C-terminal amino acids of the activated toxin fragment identified. In this aspect of the invention, the skilled person can determine that, for example, the toxin fragment of SEQ ID NO:31 or SEQ SEQ ID NO:32 or SEQ ID NO:33 likely comprises amino acids from about 29 to about 603 or from about 29 to about 624 or from about 29 to about 635 of SEQ ID NO:31 or SEQ ID NO:32 or SEQ ID NO:33, or the toxin fragment of SEQ ID NO:34 likely comprises amino acids from about amino acid 21 to about 606 or from about 21 to about 645 or from about 21 to about 648 of SEQ ID NO:34, and so forth. Cry protein variants produced by introduction or elimination of protease processing sites at appropriate positions in the coding sequence to allow, or eliminate, proteolytic cleavage of a larger variant protein by insect, plant or microorganism proteases are also within the scope of the invention. The end result of such manipulation is understood to be the generation of toxin fragment molecules having the same or better activity as the intact Cry protoxin protein.

In some embodiments of the invention, a chimeric gene is provided that comprises a heterologous promoter operably linked to a polynucleotide comprising, consisting essentially of or consisting of a nucleotide sequence that encodes a Cry protein toxic to a lepidopteran pest, wherein the nucleotide sequence (a) has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:1-10, or a toxin-encoding fragment thereof; or (b) encodes a protein comprising an amino acid sequence that has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:31-40, or a toxin fragment thereof; or (c) is a synthetic sequence of (a) or (b) that has codons optimized for expression in a transgenic organism.

In other embodiments, the heterologous promoter is a plant-expressible promoter. For example, without limitation, the plant-expressible promoter can be selected from the group of promoters consisting of ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, *petunia* chalcone isomerase, bean glycine rich protein 1, potato patatin, lectin, CaMV 35S and S-E9 small subunit RuBP carboxylase promoter.

In additional embodiments, the protein encoded by the chimeric gene is toxic to one or more lepidopteran pests selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In further embodiments, the polynucleotide comprises, consists essentially of or consists of a nucleotide sequence that has at least 80% to at least 99% sequence identity with SEQ ID NO:1, or a toxin-encoding fragment thereof, or has at least 80% to at least 99% sequence identity with SEQ ID NO:2, or a toxin-encoding fragment thereof, or has at least 80% to at least 99% sequence identity with SEQ ID NO:3, or a toxin-encoding fragment thereof, or has at least 80% to at least 99% sequence identity with SEQ ID NO:4, or a toxin-encoding fragment thereof, or has at least 80% to at least 99% sequence identity with SEQ ID NO:5, or has at least 80% to at least 99% sequence identity with SEQ ID NO:6, or has at least 80% to at least 99% sequence identity with SEQ ID NO:7, or has at least 80% to at least 99% sequence identity with SEQ ID NO:8, or has at least 80% to at least 99% sequence identity with SEQ ID NO:9, or has at least 80% to at least 99% sequence identity with SEQ ID NO:10.

In other embodiments, the polynucleotide comprises, consists essentially of or consists of any one of SEQ ID NOs:1-10, or a toxin-encoding fragment thereof.

In other embodiments, the polynucleotide comprises, consists essentially of or consists of a nucleotide sequence that encodes a protein comprising, consisting essentially of or consisting of an amino acid sequence that has at least 80% to at least 99% sequence identity with any one of SEQ ID NOS:31-40, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:31.

In further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:32.

In still further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:33, or a toxin fragment thereof.

In further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:34, or a toxin fragment thereof.

In still further embodiments, the amino acid sequence has at least 90%, or at least 81%, or at least 82%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:35.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:36.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:37, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:38, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:39, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:40.

In some embodiments, the chimeric gene of the invention comprises a polynucleotide comprising, consisting essentially of or consisting of a synthetic sequence of a nucleotide sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any of SEQ ID NOS:11-30, or a toxin-encoding fragment thereof, wherein the synthetic sequence has codons optimized for expression is a transgenic organism, such as a transgenic plant or a transgenic bacteria. In other embodiments, the chimeric gene of the invention comprises a polynucleotide comprising, consisting essentially of or consisting of a synthetic sequence of a nucleotide sequence that encodes a protein comprising an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any of SEQ ID NOS:31-50, or a toxin fragment thereof, wherein the synthetic sequence has codons optimized for expression is a transgenic organism. In further embodiments, the transgenic organism is a transgenic bacteria or a transgenic plant.

In some embodiments, the invention provides a synthetic polynucleotide comprising, consisting essentially of or consisting of a nucleotide sequence that encodes a protein that is toxic to a lepidopteran pest, wherein the nucleotide sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:11-30, or a toxin-encoding fragment thereof.

In other embodiments, the invention provides a synthetic polynucleotide comprising, consisting essentially of or consisting of a nucleotide sequence that encodes a protein that is toxic to a lepidopteran pest, wherein the nucleotide sequence encodes an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:31-50, or a toxin fragment thereof.

Cry proteins of the invention may be isolated from certain *Bacillus thuringiensis* (Bt) strains such as C0530, C0537, C0651, C0652, C0724, C0801, C1079 and M2776. It will be recognized that Cry proteins of the invention may also be isolated from other Bt strains and that such Bt strains can be isolated by standard techniques and tested for toxicity to a lepidopteran pest of the invention. Generally Bt strains can be isolated from any environmental sample, including soil, plant, insect, grain elevator dust, and other sample material, etc., by methods known in the art. See, for example, Travers et al. (1987) Appl. Environ. Microbiol. 53:1263-1266; Saleh et al. (1969) Can J. Microbiol. 15:1101-1104; DeLucca et al. (1981) Can J. Microbiol. 27:865-870; and Norris, et al. (1981) "The genera *Bacillus* and Sporolactobacillus," In Starr et al. (eds.), The Prokaryotes: A Handbook on Habitats, Isolation, and Identification of Bacteria, Vol. II, Springer-Verlog Berlin Heidelberg. After isolation, Bt strains can be tested for toxicity to a lepidopteran pest and Cry proteins encompassed by the invention can be identified. Therefore, in some embodiments, the invention provides an isolated *Bacillus thuringiensis* (Bt) strain that produces a Cry protein or a recombinant Cry protein comprising, consisting essentially of or consisting of an amino acid sequence having at least 80% to at least 99% sequence identity to any of SEQ ID NOs: 31-40. In other embodiments, the Bt strain is selected from the group consisting of C0530, C0537, C0651, C0652, C0724, C0801, C1079 and M2776. In still further embodiments, the Cry protein or recombinant Cry protein comprises, consists essentially of or consists of any of SEQ ID NOs:31-40.

According to some embodiments, the invention provides an optionally isolated Cry protein that is toxic to a lepidopteran pest, wherein the protein comprises, consists essentially of or consists of (a) an amino acid sequence that has at least 80% sequence identity to at least 99% sequence identity with an amino acid sequence represented by any one of SEQ ID NOs:31-50, or a toxin fragment thereof; or (b) an amino acid sequence that is encoded by a nucleotide sequence that has at least 80% sequence identity to at least 99% sequence identity with a nucleotide sequence represented by any one of SEQ ID NOs: 11-30, or a toxin-encoding fragment thereof.

In other embodiments, the optionally isolated Cry protein comprises, consists essentially of or consists of an amino acid sequence that has at least 80% to at least 99% sequence identity with any one of SEQ ID NOS:31-50, or a toxin fragment thereof. In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:31, or a toxin fragment thereof.

the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:31, or a toxin fragment thereof.

In further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:, or a toxin fragment thereof.

In still further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:33, or a toxin fragment thereof.

In other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:34, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:35, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:36, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:37, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:38, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:39, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:40.

In some embodiments, the amino acid sequence comprises, consists essentially of or consists of any one of SEQ ID NOs:31-50, or a toxin fragment thereof. In other embodiments, the amino acid sequence is encoded by a nucleotide sequence comprising, consisting essentially of or consisting of any of SEQ ID NOs:1-30, or a toxin-encoding fragment thereof.

In other embodiments, the Cry proteins of the invention are toxic to a lepidopteran pest selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In some embodiments, the invention encompasses a recombinant Cry protein that is toxic to a lepidopteran pest, wherein the recombinant Cry protein comprises, consists essentially of or consists of (a) an amino acid sequence that has at least 80% to at least 99% sequence identity with an amino acid sequence represented by any of SEQ ID NOs: 41-50, or a toxin fragment thereof; or (b) an amino acid sequence that is encoded by a nucleotide sequence that has at 80% to at least 99% sequence identity with a nucleotide sequence represented by any of SEQ ID NOs:21-30, or a toxin-encoding fragment thereof.

In other embodiments, the recombinant Cry protein comprises, consists essentially of or consists of an amino acid sequence that has at least 80% to at least 99% sequence identity with any one of SEQ ID NOs:41-50, or a toxin fragment thereof. In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:41, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:42, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:43, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:44, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:45, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:46, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:47, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:48, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:49, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:50, or a toxin fragment thereof.

In still further embodiments, the recombinant Cry protein comprises, consists essentially of or consists of an amino acid sequence of any of SEQ ID NOs:41-50, or a toxin fragment thereof. In other embodiments, the recombinant Cry protein is encoded by a nucleotide sequence that comprises, consists essentially of or consists of any of SEQ ID NOs:21-30, or a toxin-encoding fragment thereof.

Antibodies raised in response to immune challenge by a native or mutant BT-0001, BT-0003, BT-0020, BT-0022, BT-0027, BT-0029, BT-0030, BT-0031, BT-0201 and BT-0202 and the like or related Cry proteins are also encompassed by the invention. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988. Antibodies a laboratory manual. pp. 726. Cold Spring Harbor Laboratory) and as in Goding (Monoclonal Antibodies: Principles & practice. 1986. Academic Press, Inc., Orlando, Fla.). The present invention encompasses insecticidal proteins that cross-react with antibodies, particularly monoclonal antibodies, raised against one or more of the insecticidal Cry proteins of the present invention.

The antibodies produced in the invention are also useful in immunoassays for determining the amount or presence of a native or mutant BT-0001, BT-0003, BT-0020, BT-0022, BT-0027, BT-0029, BT-0030, BT-0031, BT-0201 and BT-0202 or related Cry protein in a biological sample. Such assays are also useful in quality-controlled production of compositions containing one or more of the Cry proteins of the invention or related toxic proteins. In addition, the antibodies can be used to assess the efficacy of recombinant production of one or more of the Cry proteins of the invention or a related protein, as well as for screening expression libraries for the presence of a nucleotide sequence encoding one or more of the Cry proteins of the invention or related protein coding sequences. Antibodies are useful also as affinity ligands for purifying or isolating any one or more of the proteins of the invention and related proteins. The Cry proteins of the invention and proteins containing related antigenic epitopes may be obtained by over expressing full or partial lengths of a sequence encoding all or part of a Cry protein of the invention or a related protein in a preferred host cell.

It is recognized that DNA sequences that encode a native Cry protein of the invention may be altered by various methods, and that these alterations may result in DNA sequences encoding proteins with amino acid sequences different than that encoded by a native Cry protein of the invention. A Cry protein may be altered in various ways to make a mutant Cry protein including amino acid substitutions, deletions, truncations, and insertions of one or more amino acids, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a native Cry protein can be prepared by mutations in a polynucleotide that encodes the protein. This may also be accomplished by one of several forms of mutagenesis or in directed evolution. In some aspects, the changes encoded in the amino acid sequence will not substantially affect the function of the protein. Such variants will possess the desired insecticidal activity. In some embodiments of the invention, nucleotide sequences represented by SEQ ID NOs: 1-10 are altered to introduce amino acid substitutions in the encoded protein. In other embodiments, the resulting mutant protein is encoded by a synthetic mutant polynucleotide comprising a nucleotide sequence represented by any one of SEQ ID NOs:21-30. In other embodiments, the mutant proteins comprise, consist essentially of or consist of an amino acid sequence represented by any one of SEQ ID NOs:41-50.

It is understood that the ability of an insecticidal protein to confer insecticidal activity may be improved by the use of such techniques upon the compositions of this invention. For example, one may express a Cry protein in host cells that exhibit high rates of base mis-incorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the Cry protein mutations in a non-mutagenic strain, and identify mutated genes with insecticidal activity, for example by performing an assay to test for insecticidal activity. Generally, the protein is mixed and used in feeding assays. See, for example Marrone et al. (1985) J. of Economic Entomology 78:290-293. Such assays can include contacting plants with one or more pests and determining the plant's ability to survive or cause the death of the pests. Examples of mutations that result in increased toxicity are found in Schnepf et al. (1998) Microbiol. Mol. Biol. Rev. 62:775-806.

Alternatively, alterations may be made to an amino acid sequence of the invention at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

A Cry protein of the invention can also be mutated to introduce an epitope to generate antibodies that recognize the mutated protein. Therefore, in some embodiments, the invention provides a mutated Cry protein, wherein an amino acid substitution in a native Cry protein produces a mutant Cry protein having an antigenic region that allows the mutant Cry protein to be distinguished from the native Cry protein in a protein detection assay.

In some embodiments, the invention provides a method of making an antibody that differentially recognizes a mutated Cry protein from the native Cry protein from which the mutated Cry protein is derived, the method comprising the steps of substituting amino acids in an antigenic loop of a native Cry protein and raising antibodies that specifically recognize the mutated antigenic loop in the mutated Cry protein and does not recognize the native Cry protein. In one embodiment, the antigenic loop is identified in non-conserved regions outside of domain I of the native Cry protein. In another embodiment, the antigenic loop is not a loop involved in the Cry protein's insect gut receptor recognition or involved in the protease activation of the Cry protein.

Variant nucleotide and amino acid sequences of the invention also encompass sequences derived from mutagenic and recombinogenic procedures such as DNA shuffling. With such a procedure, one or more different toxic protein coding regions can be used to create a new toxic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

Domain swapping or shuffling is another mechanism for generating altered Cry proteins of the invention. Domains may be swapped between Cry proteins, resulting in hybrid or chimeric toxic proteins with improved pesticidal activity or target spectrum. Methods for generating recombinant proteins and testing them for pesticidal activity are well known in the art (see, for example, Naimov et al. (2001) Appl. Environ. Microbiol. 67:5328-5330; de Maagd et al. (1996) Appl. Environ. Microbiol. 62:1537-1543; Ge et al. (1991) J. Biol. Chem. 266:17954-17958; Schnepf et al. (1990) J. Biol. Chem. 265:20923-20930; Rang et al. 91999) Appl. Environ. Microbiol. 65:2918-2925). In some embodiments, the invention provides hybrid Cry proteins comprising at a C-terminus, amino acids from a first Cry protein of the invention and at an N-terminus, amino acids from a second Cry protein of the invention different from the first Cry protein of the invention.

In some embodiments, the invention provides a recombinant vector comprising a polynucleotide, a nucleic acid molecule, an expression cassette or a chimeric gene of the invention. In other embodiments, the vector is further defined as a plasmid, cosmid, phagemid, artificial chromosome, phage or viral vector. Certain vectors for use in transformation of plants and other organisms are known in the art.

Thus, some embodiments of the invention are directed to expression cassettes designed to express the polynucleotides and nucleic acid molecules of the invention. As used herein, “expression cassette” means a nucleic acid molecule having at least a control sequence operatively linked to a nucleotide sequence of interest. In this manner, for example, plant promoters operably linked to the nucleotide sequences to be expressed are provided in expression cassettes for expression in a plant, plant part or plant cell.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the invention, an expression cassette of this invention also can include other regulatory sequences. As used herein, “regulatory sequences” means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, termination signals, and polyadenylation signal sequences.

In some embodiments, an expression cassette of the invention also can include polynucleotides that encode other desired traits in addition to the Cry proteins of the invention. Such expression cassettes comprising the stacked traits may be used to create plants, plant parts or plant cells having a desired phenotype with the stacked traits (i.e., molecular stacking). Such stacked combinations in plants can also be created by other methods including, but not limited to, cross breeding plants by any conventional methodology. If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int’l Patent Application Publication Nos. WO 99/25821; WO 99/25854; WO 99/25840; WO 99/25855 and WO 99/25853.

The expression cassette also can include an additional coding sequence for one or more polypeptides or double stranded RNA molecules (dsRNA) of interest for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as “herbicide tolerance”), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903, 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), 3-glucosidase (EC 3.2.1.21); c) L-arabinases, such as endo-1,5-a-L-arabinase (EC 3.2.1.99), α-arabinosidases (EC 3.2.1.55) and the like; d) galactanases such as endo-1,4-3-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like. In one embodiment, the α-amylase is the synthetic α-amylase, Amy797E, described is U.S. Pat. No. 8,093,453, herein incorporated by reference in its entirety.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Double stranded RNA molecules useful with the invention include, but are not limited to those that suppress target insect genes. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

In some embodiments, the invention provides a transgenic non-human host cell comprising a polynucleotide, a nucleic acid molecule, a chimeric gene, an expression cassette or a recombinant vector of the invention. The transgenic non-human host cell can include, but is not limited to, a plant cell, a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc*, or *Alcaligenes*. Thus, for example, as biological insect control agents, the Cry proteins of the invention can be produced by expression of a chimeric gene encoding the Cry proteins of the invention in a bacterial cell. For example, in some embodiments, a *Bacillus thuringiensis* cell comprising a chimeric gene of the invention is provided.

In further embodiments, the invention provides a transgenic plant cell that is a dicot plant cell or a monocot plant cell. In additional embodiments, the dicot plant cell is selected from the group consisting of a soybean cell, sunflower cell, tomato cell, cole crop cell, cotton cell, sugar beet cell and tobacco cell. In further embodiments, the monocot cell is selected from the group consisting of a barley cell, maize cell, oat cell, rice cell, sorghum cell, sugar cane cell and wheat cell. In some embodiments, the invention provides a plurality of dicot cells or monocot cells expressing a Cry protein of the invention that is encoded by a chimeric gene of the invention. In other embodiments the plurality of cells are juxtaposed to form an apoplast and are grown in natural sunlight.

In other embodiments of the invention, an insecticidal Cry protein of the invention is expressed in a higher organism, for example, a plant. In this case, transgenic plants expressing effective amounts of the insecticidal protein protect themselves from plant pests such as insect pests. When an insect starts feeding on such a transgenic plant, it ingests the expressed insecticidal Cry protein. This can deter the insect from further biting into the plant tissue or may even harm or kill the insect. A polynucleotide of the invention is inserted into an expression cassette, which is then stably integrated in the genome of the plant. In other embodiments, the polynucleotide is included in a non-pathogenic self-replicating virus. Plants transformed in accordance with the invention may be monocots or dicots and include, but are not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, *papaya*, mango, banana, and specialty plants, such as *Arabidopsis*, and woody plants such as coniferous and deciduous trees. Preferably, plants of the of the invention are crop plants such as maize, sorghum, wheat, sunflower, tomato, crucifers, peppers, potato, cotton, rice, soybean, sugar beet, sugarcane, tobacco, barley, oilseed rape, and the like.

Once a desired polynucleotide has been transformed into a particular plant species, it may be propagated in that species or moved into other varieties of the same species, particularly including commercial varieties, using traditional breeding techniques.

A polynucleotide of the invention is expressed in transgenic plants, thus causing the biosynthesis of the corresponding Cry protein, either in protoxin or mature toxin form, in the transgenic plants. In this way, transgenic plants with enhanced yield protection in the presence of insect pressure are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, high expression in plants, for example corn plants, is best achieved from coding sequences that have at least about 35% GC content, or at least about 45%, or at least about 50%, or at least about 60%. Microbial nucleotide sequences that have low GC contents may express poorly in plants due to the existence of ATTTA motifs that may destabilize messages, and AATAAA motifs that may cause inappropriate polyadenylation. Although certain gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described for example in U.S. Pat. Nos. 5,625,136; 5,500,365 and 6,013,523.

In some embodiments, the invention provides synthetic coding sequences or polynucleotide made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are represented by any one of SEQ ID NOs: 11-30. It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

The novel Cry protein coding sequences of the invention, either as their native sequence or as synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Suitable constitutive promoters include, for example, CaMV 35S promoter (SEQ ID NO:1546; Odell et al., Nature 313:810-812, 1985); *Arabidopsis* At6669 promoter (SEQ ID NO:1652; see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.Molec. Biol.

Tissue-specific or tissue-preferential promoters useful for the expression of the novel cry protein coding sequences of the invention in plants, particularly maize, are those that direct expression in root, pith, leaf or pollen. Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143). 323-32 1990), napA (Stalberg, et al., Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMB03:1409-15, 1984), Barley Itrl promoter, barley BI, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters [e.g., rice OSH1 (Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), *apetala*-3, plant reproductive tissues [e.g., OsMADS promoters (U.S. Patent Application 2007/0006344)].

The nucleotide sequences of this invention can also be expressed under the regulation of promoters that are chemically regulated. This enables the Cry proteins of the invention to be synthesized only when the crop plants are treated with the inducing chemicals. Examples of such technology for chemical induction of gene expression is detailed in the published application EP 0 332 104 and U.S. Pat. No. 5,614,395. In one embodiment, the chemically regulated promoter is the tobacco PR-la promoter.

Another category of promoters useful in the invention is that which is wound inducible. Numerous promoters have been described which are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Non-limiting examples of promoters that cause tissue specific expression patterns that are useful in the invention include green tissue specific, root specific, stem specific, or flower specific. Promoters suitable for expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition to the selection of a suitable promoter, constructs for expression of an insecticidal toxin in plants require an appropriate transcription terminator to be operably linked downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Plant Transformation

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (Phosphomannose Isomerase), provide resistance to an antibiotic (kanamycin, hygromycin or methotrexate) or a herbicide (glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) *Nucleic Acids Res.* 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) *Proc. Nati. Acad. Sci. USA* 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) *Proc. Natl. Acad. Sci. USA* 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransf erase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell. As used herein, "selectable marker" means a nucleotide sequence that when expressed imparts a distinct phenotype to the plant, plant part or plant cell expressing the marker and thus allows such transformed plants, plant parts or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptll, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding j-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Additional embodiments of the invention include harvested products produced from the transgenic plants or parts thereof of the invention, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention, wherein said seed or other plant part comprises a nucleic acid molecule/polynucleotide/nucleotide sequence of this invention.

In other embodiments, the invention provides an extract from a transgenic seed or a transgenic plant of the invention, wherein the extract comprises a nucleic acid molecule, a polynucleotide, a nucleotide sequence or a toxic protein of the invention. Extracts from plants or plant parts can be made according to procedures well known in the art (See, de la Torre et al., *Food, Agric. Environ.* 2(1):84-89 (2004); *Guidet, Nucleic Acids Res.* 22(9): 1772-1773 (1994); Lipton et al., *FoodAgric. Immun.* 12:153-164 (2000)).

Insecticidal Compositions

In some embodiments, the invention provides an insecticidal composition comprising a Cry protein of the invention in an agriculturally acceptable carrier. As used herein an "agriculturally-acceptable carrier" can include natural or synthetic, organic or inorganic material which is combined with the active Cry protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing a Cry protein of the invention in planta is an agricultural-carrier of the expressed Cry protein.

In further embodiments, the insecticidal composition comprises a bacterial cell or a transgenic bacterial cell of the invention, wherein the bacterial cell or transgenic bacterial cell produces a Cry protein of the invention. Such an insecticidal composition can be prepared by desiccation, lyophilization, homogenization, extraction, filtration, centrifugation, sedimentation, or concentration of a culture of *Bacillus thuringiensis* (Bt). Such Bt cultures can be selected from the group of Bt strains consisting of C0537, C0651, C0652, C0724, C0801, C1079 and M2776 described below in the Examples or transgenic Bt cultures. In additional embodiments, the composition comprises from about 1% to about 99% by weight of the Cry protein of the invention.

The Cry proteins of the invention can be used in combination with other pest control agents to increase pest target range or for the prevention or management of insect resistance. Therefore, in some embodiments, the invention provides a composition that controls one or more plant pests, wherein the composition comprises a first Cry protein of the invention and a second pest control agent different from the first Cry protein. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first Cry protein of the invention when the transgenic plant comprises the second pest control agent. In other embodiments, the formulation comprises the second pest control agent when the transgenic plant comprises the first Cry protein of the invention.

In some embodiments, the second pest control agent can be an agent selected from the group consisting of a chemical pesticide, such as an insecticide, a *Bacillus thuringiensis* (Bt) insecticidal protein, a *Xenorhabdus* insecticidal protein, a *Photorhabdus* insecticidal protein, a *Brevibacillus laterosporus* insecticidal protein, a *Bacillus sphaericus* insecticidal protein, a protease inhibitors (both serine and cysteine types), lectins, alpha-amylase, peroxidase, cholesterol oxidase and a double stranded RNA (dsRNA) molecule.

In other embodiments, the second pest control agent is a chemical pesticide selected from the group consisting of pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from the group consisting of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from the group consisting of Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa and Cry73Aa.

In further embodiments, the second pest control agent is a Vip3 vegetative insecticidal protein selected from the group consisting of Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2 and Vip3Bb3.

In still further embodiments, the first Cry protein of the invention and the second pest control agent are co-expressed in a transgenic plant. This co-expression of more than one pesticidal principle in the same transgenic plant can be achieved by genetically engineering a plant to contain and express all the genes necessary. Alternatively, a plant, Parent 1, can be genetically engineered for the expression of the Cry protein of the invention. A second plant, Parent 2, can be genetically engineered for the expression of a second pest control agent. By crossing Parent 1 with Parent 2, progeny plants are obtained which express all the genes introduced into Parents 1 and 2.

In other embodiments, the invention provides a stacked transgenic plant resistant to plant pest infestation comprising a DNA sequence encoding a dsRNA for suppression of an essential gene in a target pest and a DNA sequence encoding a Cry protein of the invention exhibiting biological activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, a Cry protein of the invention acts to transiently reduce the midgut pH which serves to stabilize the co-ingested dsRNA rendering the dsRNA effective in silencing the target genes.

In addition to providing compositions, the invention provides methods of producing a Cry protein toxic to a lepidopteran pest. Such a method comprises, culturing a transgenic non-human host cell that comprises polynucleotide or a chimeric gene or nucleic acid molecule or a recombinant vector of the invention under conditions in which the host cell produces a protein toxic to the lepidopteran pest. In some embodiments, the transgenic non-human host cell is a plant cell. In some other embodiments, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In other embodiments of the method, the lepidopteran pest is selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*), rice leaffolder (*Cnaphalocrocis medinalis*), and any combination thereof.

In further embodiments of the method, the chimeric gene comprises any of SEQ ID NOs:1-10. In still other embodiments, the produced protein comprises an amino acid sequence of any of SEQ ID NOs: 31-40.

In some embodiments of the method, the chimeric gene comprises a nucleotide sequence that is codon optimized for expression in a plant. In other embodiments, the chimeric gene comprises any of SEQ ID NOs: 11-20. In further embodiments, the produced protein comprises an amino acid sequence of any of SEQ ID NOs:31-50.

In further embodiments, the invention provides a method of producing a pest-resistant (e.g., an insect-resistant) transgenic plant, comprising: introducing into a plant a polynucleotide, a chimeric gene, a recombinant vector, an expression cassette or a nucleic acid molecule of the invention comprising a nucleotide sequence that encodes a Cry protein of the invention, wherein the nucleotide sequence is expressed in the plant, thereby conferring to the plant resistance to at least a lepidopteran insect pest, and producing a insect-resistant transgenic plant. In some embodiments, a pest-resistant transgenic plant is resistant to at least European corn borer (*Ostrinia nubilalis*) or black cutworm (*Agrotis ipsilon*) as compared to a control plant lacking the polynucleotide, chimeric gene, recombinant vector, expression cassette or nucleic acid molecule of the invention. In some embodiments, the introducing is achieved by transforming the plant. In other embodiments, the introducing is achieved by crossing a first plant comprising the chimeric gene, recombinant vector, expression cassette or nucleic acid molecule of the invention with a different second plant.

In some embodiments, a transgenic plant of the invention that is resistant to at least European corn borer (*Ostrinia nubilalis*) or black cutworm (*Agrotis ipsilon*) is further resistant to at least one additional insect, wherein the additional insect includes, but is not limited to, fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia furnacalis*), cotton bollworm (*Helicoverpa armigera*), striped stem borer (*Chilo suppressalis*), pink stem borer (*Sesamia calamistis*) or rice leaffolder (*Cnaphalocrocis medinalis*), and any combination thereof.

In further embodiments, a method of controlling at least a lepidopteran insect pest such as European corn borer (*Ostrinia nubilalis*) or black cutworm (*Agrotis ipsilon*) is provided, the method comprising delivering to the insects an effective amount of a Cry protein of the invention. To be effective, the Cry protein is first orally ingested by the insect. However, the Cry protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic Cry proteins of the invention. In some particular embodiments, the Cry protein of the invention is delivered orally to an insect, wherein the insect ingests one or more parts of a transgenic plant.

In other embodiments, the Cry protein of the invention is delivered orally to an insect, wherein the insect ingests one or more parts of a plant sprayed with a composition comprising the Cry proteins of the invention. Delivering the compositions of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

In further embodiments, the invention provides a method of controlling a Cry1Ab-resistant lepidopteran insect comprising delivering to the insect an effective amount of an insecticidal protein having at least 80% identity to SEQ ID NO:31 or SEQ ID NO:32. In other embodiments, the Cry1Ab-resistant insect is sugarcane borer (Diatreae *saccharalis*). In still other embodiments, the insecticidal protein comprises SEQ ID NO:31, SEQ ID NO:32, SEQ ID NO:41 or SEQ ID NO:42.

In other embodiments, the invention provides a method of preventing the development of resistance in a population of a target lepidopteran insect pest to a Cry1Ab protein expressed in a transgenic plant comprising stacking in the transgenic plant in addition to the Cry1Ab protein a second insecticidal protein having at least 80% identity to SEQ ID NO:31 or SEQ ID NO:41. In some embodiments, the target lepidopteran insect pest is sugarcane borer (*Diatraea saccharalis*). In still other embodiments, the second insecticidal protein comprises SEQ ID NO:31, SEQ ID NO:32, SEQ ID NO:41 or SEQ ID NO:42.

In some embodiments, the invention encompasses a method of providing a farmer with a means of controlling a lepidopteran pest, the method comprising supplying or selling to the farmer plant material such as a seed, the plant material comprising a polynucleotide, chimeric gene, expression cassette or a recombinant vector capable of expressing a Cry protein of the invention in a plant grown from the seed, as described above.

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

EXAMPLES

Example 1. Identification of Active Bt Strains

*Bacillus thuringiensis* isolates were cultured from spores present in current collections and maintained on T3+ penicillin agar plates. Each isolate was grown aerobically in 24 well deep blocks for about 10 days at 28° C. until sporulation, which was verified by staining with Coomasie blue/acetic acid and visualization with a microscope. After sporulation both the soluble and insoluble fractions were tested for activity against lepidopteran species of interest. Fractions were tested in a surface contamination bioassay, where the fractions were overlaid onto a multispecies artificial diet. Each isolate was screened against at least four lepidopteran species, including *Helicoverpa zea* (corn earworm), *Agrotis ipsilon* (black cutworm), *Ostrinia nubilalis* (European corn borer), and *Spodoptera frugiperda* (fall armyworm) with a sample size of 12 neonate larvae. The duration of each assay was about 7 days at room temperature; the plates were scored for mortality as well as larval growth inhibition. Observed mortality at an increase of 30% over the negative control was considered active. Based on the initial insect testing, strains C0530, C0537, C0651, C0652, C0724, C0801, C1079 and M2776 were selected for further analysis.

Example 2. Genome Assembly and Analysis

Bt cry genes of the invention were identified from the strains identified in Example 1 using a whole genome sequencing approach. Briefly, *Bacillus* DNA was sheared using a Covaris S2 ultrasonic device (Covaris, Inc., Woburn, Mass.) with the program DNA_400 bp set at duty cycle: 10%; intensity: 4; cycles/burst: 200. The DNA was treated with the NEBNext® Ultra™ End Repair/dA-tailing module (New England Biolabs, Inc. Ipswich, Mass.). Biooscience indexes 1-57 adapters (1-27 Brazil, 28-57 USA, UK and Switzerland) were ligated using NEB Quick Ligation™ as described by the supplier (New England Biolabs, Inc. Ipswich, Mass.). Ligations were cleaned up using Agencourt AMPure XP beads as described by the supplier (Beckman Coulter, Inc., Indianapolis, Ind.).

The library was size fractionated as follows: A 50 uL sample was mixed with 45 ul 75% bead mix (25% AMPure beads plus 75% NaCl/PEG solution TekNova cat # P4136). The mix was stirred and placed on magnetic rack. The resulting supernatant was transferred to a new well and 45 ul 50% bead mix (50% AMPure beads plus 50% NaCl/PEG solution TekNova cat # P4136) was added. This mix was stirred and placed on a magnetic rack. The resulting supernatant was removed and the beads were washed with 80% ethanol. 25 uL of elution buffer (EB) buffer was added and the mix placed on a magnetic rack. The final resulting supernatant was removed and placed in 1.5 mL tube. This method yielded libraries in the 525 DNA base pairs (bp) (insert plus adapter) size range.

The sized DNA library was amplified using KAPA Biosystem HiFi Hot Start (Kapa Biosystems, Inc., Wilmington, Mass.) using the following cycle conditions: [98° C., 45s]; 12×[98° C., 15s, 60° C., 30s, 72° C., 30s]; [72° C., 1 min]. Each reaction contained: 5 ul DNA library, 1 uL Bioscience universal primer (25 uM), 18 uL sterile water, luL Bioscience indexed primer (25 uM), 25 ul 2×KAPA HiFi polymerase.

Libraries were run on the Agilent 2100 Bioanalyzer (Agilent Technologies, Santa Clara, Calif.) using High Sensitivity chips to determine the library size range and average insert size. All libraries were processed for paired end (PE) sequencing (100 cycles per read; 12-24 libraries per lane) on a HiSeq 2500 sequencing system using standard manufacturer's sequencing protocols (Illumina, Inc., San Diego, Calif.).

A *Bacillus* computational analysis tool developed to identify and characterize likely Cry-like genes was used for prioritization of leads for further laboratory testing.

The genome assembly and analysis as well as the genomic library analysis described above led to the identification of five Cry1-like genes in the *Bacillus thuringiensis* strains with toxicity to at least European corn borer (*Ostrinia nubilalis*) or black cutworm (*Agrotis ipsilon*). Identifying characteristics of the Cry1-like genes and proteins are shown in Table 1.

TABLE 1

Cry genes/proteins identified in *Bacillus thuringiensis* strains.

| Strain | Protein/ Gene Name | Nearest Cry Family Member | Molecular Weight (kD) | Nucleotide SEQ ID NO: | Amino Acid SEQ ID NO: |
|---|---|---|---|---|---|
| C0530 | BT0001 | Cry1Ai | 132.2 | 1 | 31 |
| C0537 | BT0003 | Cry1Aa | 129.7 | 2 | 32 |
| C0651 | BT0020 | Cry1Bg | 129.6 | 3 | 33 |
| C0652 | BT0022 | Cry1If | 130.8 | 4 | 34 |
| C0724 | BT0027 | Cry1La | 130.3 | 5 | 35 |
| C0801 | BT0029 | Cry1Gb | 133.1 | 6 | 36 |
| C1079 | BT0030 | Cry1Hb | 128.9 | 7 | 37 |
| C1079 | BT0031 | Cry1Ib | 81.0 | 8 | 38 |
| M2776 | BT0201 | Cry1Ga | 132.0 | 9 | 39 |
| M2776 | BT0202 | Cry1Jd | 132.6 | 10 | 40 |

Example 3. Bt Protein Expression in Recombinant Host Cells

*Bacillus* Expression. The Cry proteins described in Example 2 were expressed in a crystal minus *Bacillus thuringiensis* (Bt) strain having no observable background insecticidal activity via a shuttle vector designated pCIB5634', designed for expression in both *E. coli* and Bt. Vector pCIB5634' comprises a Cry1Ac promoter that drives expression of the cloned Bt Cry gene and a erythromycin resistance marker. Expression cassettes comprising the Cry coding sequence of interest were transformed into the host Bt strain via electroporation and transgenic Bt strains were selected for on erythromycin containing agar plates. Selected transgenic Bt strains were grown to the sporulation phase in T3 media at 28° C. for 4-5 days. Cell pellets were harvested and washed iteratively before solubilization in high pH carbonate buffer (50 mM) containing 2 mM DTT.

*E. coli* Expression.

Cry proteins were expressed in *E. coli* strains using pET28a or pET29a vectors (Merck KGaA, Darmstadt, Germany). Constructs were transformed by electroporation and transgenic *E. coli* clones were selected for on kanamycin-containing agar plates. Selected transgenic *E. coli* strains were grown and Cry protein expression induced using IPTG induction at 28° C. Cells were resuspended in high pH carbonate buffer (50 mM) containing 2 mM DTT and then broken using a Microfluidics LV-1 homogenizer.

Expression Analysis.

Resulting cell lysates from either transgenic Bt or *E. coli* strains were then clarified via centrifugation and samples were analyzed for purity via SDS-PAGE and electropherogram using a BioRad Experion system (Biorad, Hercules, Calif.). Total protein concentrations were determined via Bradford or Thermo 660 assay. Purified Cry proteins were then tested in bioassays described below.

Example 4. Activity of Cry Proteins in Bioassays

The Cry proteins produced in Example 3 were tested against one or more of the following lepidopteran pest species using an art-recognized artificial diet bioassay method: European corn borer (ECB; *Ostrinia nubilalis*), black cutworm (BCW; *Agrotis ipsilon*), sugarcane borer (SCB; *Diatraea saccharlis*), fall armyworm (FAW; *Spodoptera frugiperda*), corn earworm (CEW; *Helicoverpa zea*), velvet bean caterpillar (VBC; *Anticarsia gemmatalis*), soybean looper (SBL; *Pseudoplusia includens*), southwestern corn borer (SWCB; *Diatraea grandiosella*), western bean cutworm (WBCW; *Striacosta albicosta*), tobacco budworm (TBW; *Heliothis virescens*), Asian corn borer (ACB; *Ostrinia furnacalis*), cotton bollworm (CBW; *Helicoverpa armigera*), striped stem borer (SSB; *Chilo suppressalis*), pink stem borer (PSB; *Sesamia inferens*), Oriental armyworm (OAW; *Mythimna separata*) and rice leaf folder (RLF; *Cnaphalocrocis medinails*).

An equal amount of protein in solution was applied to the surface of an artifical insect diet (Bioserv, Inc., Frenchtown, N.J.) in 24 well plates. After the diet surface dried, larvae of the insect species being tested were added to each well. The plates were sealed and maintained at ambient laboratory conditions with regard to temperature, lighting and relative himidity. A positive-control group consisted of larvae exposed to a very active and broad-spectrum wild-type *Bacillus* strain. Negative control groups consisted of larvae exposed to insect diet treated with only the buffer solution and larvea on untreated insect diet; i.e. diet alone. Mortality was assessed after about 120 hours and scored relative to the controls.

Results are shown in Table 2, where a "-" means no activity compared to the control group, a "+/−" means 0-10% activity compared to check (this category also includes 0% mortality with strong larval growth inhibition), a "+" means 10-25% activity compared to check, a "++" means 26-75% activity compared to check, and a "+++" 76-100% activity compared to check. The designation "nt" in Table 2 means the indicated protein was not tested against that particular pest.

TABLE 2

Results of bioassays with Cry Proteins.

| Insect | BT Cry Protein 0001 | 0003 | 0020 | 0022 | 0027 | 0029 | 0030 | 0031 | 0201 | 0202 |
|---|---|---|---|---|---|---|---|---|---|---|
| FAW | − | − | − | − | + | + | − | − | − | +/− |
| CEW | +++ | ++ | − | + | − | +/− | +/− | − | − | − |
| ECB | +++ | +++ | +++ | +++ | +++ | − | +/− | − | ++ | ++ |
| BCW | +++ | +++ | ++ | +++ | − | + | − | +/− | − | +/− |
| SCB | +++ | +++ | +++ | +++ | − | ++ | nt | − | − | − |
| VBC | nt | nt | +++ | +++ | nt | +++ | nt | − | +++ | nt |
| SBL | +++ | +++ | +++ | +++ | nt | +++ | nt | − | − | +++ |
| SWCB | ++ | ++ | ++ | +++ | nt | + | nt | nt | +++ | +/− |
| WBCW | ++ | ++ | + | − | nt | nt | ++ | nt | − | nt |
| TBW | +++ | +++ | +++ | ++ | nt | nt | nt | nt | − | +/− |
| ACB | +++ | +++ | +++ | | | + | +++ | | ++ | + |
| OAW | +++ | ++ | + | | | − | +/− | | +/− | − |

the potential for developing economically-relevant levels of resistance to the Cry proteins currently being used commercially in transgenic crops. For example, Zhang et al. (2013. J. Invert. Pathol. 112:267-272) screened field collected sugarcane borer (SCB; *Diatraea saccharalis*) for resistance and identified eight out of 191 individual SCB that possessed major resistance alleles to Cry1Ab corn plants. From these eight individuals Zhang et al. established and further selected Cry1Ab-resistant SCB populations in the laboratory. Zhang et al. also determined that the Cry1Ab-resistant SCB were highly cross-resistant to other Cry proteins, including Cry1Aa and Cry1Ac and moderately cross-resistant to Cry1F.

Sugarcane borer is a major lepidopteran pest of corn in the mid-southern region of the United States and in South America. Therefore, it is important to find Cry proteins that have a different mode of action than the Cry proteins currently on the market for use as insect resistance management tools. Particularly useful are proteins that have high efficacy against Cry1Ab-resistant insects.

Certain Cry proteins of the invention were tested for efficacy against the Cry1Ab-resistant sugarcane borer described in Zhang et al. (supra). Both a Cry1Ab-susceptable (wildtype) and the Cry1Ab-resistant SCB were assayed at the same time essentially as described in Zhang et al. Results, shown in Table 3, indicate that BT-0001 and BT-0003 are highly efficacious against the Cry1Ab-resistant insects. This is particularly surprising since BT-0003 and BT-0001 have 93 and 87 percent identity, respectively, to

Example 5. Cry Proteins Active Against Cry1Ab-Resistant Insects

Although widespread use of transgenic crops expressing Cry proteins provides unprecedented control of certain lepidopteran insect pests, the threat that targeted insects pests may develop resistance to such technology is real. To date there have been reports of field resistance that leads to control failure or significantly reduced control efficacy due to intensive use of transgenic crops expressing Cry proteins in at least four cases: fall armyworm (*Spodoptera frugiperda*) to Cry1F in corn in Puerto Rico (Storer et al. 2010. J. Econ. Entomol. 103:1031-1038), African stem borer (*Busseola fusca*) to Cry1Ab corn in South Africa (Van Rensburg. 2007. J. Plant Soil. 24:147-151), pink bollworm (*Pectinophora gossypiella*) to Cry1Ac cotton in India (Dhurua & Gujar. 2011. India Pest Manage. Sci. 67:898-903) and western corn rootworm (*Diabrotica virgifera*) to Cry3Bb1 corn in the United States. Other insect pests may also have Cry1Aa; a protein that Zhang et al. demonstrated was not efficacious against Cry1Ab-resistant sugarcane borer due to cross-resistance.

TABLE 3

Activity of Cry Proteins Against Cry1Ab-resistant Insects.

| Treatment | SCB Percent Mortality Cry1Ab-Susceptable | Cry1Ab-Resistant |
|---|---|---|
| BT-0001 | 100 | 92* |
| BT-0003 | 100 | 92* |
| Negative Control 1 | 12 | 0 |
| Negative Control 2 | 8 | 0 |

*'Practical' mortality, as defined by Zhang et al. (supra), was 100%.

This result is particularly surprising for the BT-0003 protein since more than 80% of the protein is a Cry1Aa sequence, having only three amino acid differences from Cry1Aa1 in the region from position 203-1176 of SEQ ID NO:32 as shown in Tables 4A. 4B and 4C below. Amino acid differences are shown by letter changes. Same amino acids are indicated by a period ("."). Interestingly, the native BT-0003 amino acid sequence is a hybrid between Cry1Ah (SEQ ID NO:51) from amino acid position 1-202 and a Cry1Aa (SEQ ID NO:52)_from amino acid position 203-1176. Thus it appears that the first 202 amino acids and/or the three amino acid mutations in the region from position 203-1176 are responsible for the efficacy against the Cry1Ab-resistant insects.

Thus it is clear from these results that both BT-0001 and BT-0003 provide a means of mitigating resistance development to the current transgenic crops containing a Cry1Ab protein or a means of combatting Cry1Ab-resistant insects, particularly in tropical regions where certain aspects of pest biology, such as overlapping generations per growing season, aid in the evolution of resistance.

TABLE 4A

Sequence Alignment of BT-0003 with Cry1Ah1 and Cry1Aa1.

| | | |
|---|---|---|
| BT0003 (SEQ ID NO: 32) | 1 | MEIVNNQNQCVPYNCLNNPEIEILEGGRISVGNTPIDISL |
| Cry1Ah1 (SEQ ID NO: 51) | 1 | ........................................ |
| Cry1Aa1 (SEQ ID NO: 52) | 1 | .DNNP.I.E.I.....S...V.V.G.E..ET.Y....... |
| BT0003 (SEQ ID NO: 32) | 41 | SLTQFLLSEFVPGAGFVLGLIDLIWGFVGPSQWDAFLAQV |
| Cry1Ah1 (SEQ ID NO: 51) | 41 | ........................................ |
| Cry1Aa1 (SEQ ID NO: 52) | 41 | ....................V.I...IF........PV.I |
| BT0003 (SEQ ID NO: 32) | 81 | EQLINQRIAEAVRNTAIQELEGMARVYRTYATAFAEWEKA |
| Cry1Ah1 (SEQ ID NO: 51) | 81 | ........................................ |
| Cry1Aa1 (SEQ ID NO: 52) | 81 | ........E.FA..Q..SR...LSNL.QI..ES.R...AD |
| BT0003 (SEQ ID NO: 32) | 121 | PDDPELREALRTQFTATETYISGRISVLKIQTFEVQLLSV |
| Cry1Ah1 (SEQ ID NO: 51) | 121 | ........................................ |
| Cry1Aa1 (SEQ ID NO: 52) | 121 | .TN.A...EM.I..NDMNSALTTA.PL.AV.NYQ.P.... |
| BT0003 (SEQ ID NO: 32) | 161 | FAQAANLHLSLLRDVVFFGQRWGFSTTTVNNYYNDLTEGI |
| Cry1Ah1 (SEQ ID NO: 51) | 161 | ........................................ |
| Cry1Aa1 (SEQ ID NO: 52) | 161 | YV........V....SV.......DAA.I.SR.....RL. |
| BT0003 (SEQ ID NO: 32) | 201 | STYTDYAVRWYNTGLERVWGPDSRDWVRYNQFRRELTLTV |
| Cry1Ah1 (SEQ ID NO: 51) | 201 | ........................................ |
| Cry1Aa1 (SEQ ID NO: 52) | 201 | GN...................................... |
| BT0003 (SEQ ID NO: 32) | 241 | LDIVALFSNYDSRRYPIRTVSQLTREIYTNPVLENFDGSF |
| Cry1Ah1 (SEQ ID NO: 51) | 241 | .......P................................ |
| Cry1Aa1 (SEQ ID NO: 52) | 241 | ........................................ |
| BT0003 (SEQ ID NO: 32) | 281 | RGMAQRIEQNIRQPHLMDILNSITIYTDVHRGFNYWSGHQ |
| Cry1Ah1 (SEQ ID NO: 51) | 281 | ..S..G..RS..S..............A...YY....... |
| Cry1Aa1 (SEQ ID NO: 52) | 281 | ........................................ |
| BT0003 (SEQ ID NO: 32) | 321 | ITASPVGFSGPEFAFPLFGNAGNAAPPV-LVSLTGLGIFR |
| Cry1Ah1 (SEQ ID NO: 51) | 321 | .M...........T...Y.TM.....QQRI.AQL.Q.VY. |
| Cry1Aa1 (SEQ ID NO: 52) | 321 | ............................-........... |
| BT0003 (SEQ ID NO: 32) | 360 | TLSSPLYRRIILGSGPNNQELFVLDGTEFSFASLTTNLPS |
| Cry1Ah1 (SEQ ID NO: 51) | 361 | ....TF...-PFNI.I...Q.S.......AYGT-SS.... |
| Cry1Aa1 (SEQ ID NO: 52) | 360 | ........................................ |
| BT0003 (SEQ ID NO: 32) | 400 | TIYRQRGTVDSLDVIPPQDNSVPPRAGFSHRLSHVTML-S |
| Cry1Ah1 (SEQ ID NO: 51) | 399 | AV..KS.......E....N.N....Q.........S.FR. |
| Cry1Aa1 (SEQ ID NO: 52) | 400 | ......................................-. |
| BT0003 (SEQ ID NO: 32) | 439 | QAAGAVYTLRAPTFSWQHRSAEFNNIIPSSQITQIPLTKS |
| Cry1Ah1 (SEQ ID NO: 51) | 439 | GSSSS.SII...M...I ..........ADS.....AV.G |
| Cry1Aa1 (SEQ ID NO: 52) | 439 | ........................................ |
| BT0003 (SEQ ID NO: 32) | 479 | TNLGSGTSVVKGPGFTGGDILRRTSPGQISTLRVNITAPL |
| Cry1Ah1 (SEQ ID NO: 51) | 479 | NF.FN.-..IS........LV.LN.S.NNIQN.GY.EV.I |
| Cry1Aa1 (SEQ ID NO: 52) | 479 | ........................................ |
| BT0003 (SEQ ID NO: 32) | 519 | -----SQRYRVRIRYASTTNLQFHTSIDGRPINQGNFSAT |
| Cry1Ah1 (SEQ ID NO: 51) | 518 | HFPST.T.....V....V.PIHLNVNWGNSS.FSNTVP.. |
| Cry1Aa1 (SEQ ID NO: 52) | 519 | -----................................... |

TABLE 4B

Continued Alignment of BT-0003 with Cry1Ah1 and Cry1Aa1.

| | | |
|---|---|---|
| BT0003 (SEQ ID NO: 32) | 554 | MSSGSNLQSGSFRTVGFTTPFNFSNGSSVFTLSAHVFNSG |
| Cry1Ah1 (SEQ ID NO: 51) | 558 | AT.LD....SD.GYFESANA.TS.L.NI.---GVRN.SGT |
| Cry1Aa1 (SEQ ID NO: 52) | 554 | ........................................ |

TABLE 4B-continued

| Continued Alignment of BT-0003 with Cry1Ah1 and Cry1Aa1. | | |
|---|---|---|
| BT0003 (SEQ ID NO: 32) | 594 | NEVYIDRIEFVPAEVTFEAEYDLERAQKAVNELFTSSNQI |
| Cry1Ah1 (SEQ ID NO: 51) | 595 | AG.I...F..I.VTA.L....N.........A....T..L |
| Cry1Aa1 (SEQ ID NO: 52) | 594 | ........................................ |
| BT0003 (SEQ ID NO: 32) | 634 | GLKTDVTDYHIDQVSNLVECLSDEFCLDEKQELSEKVKHA |
| Cry1Ah1 (SEQ ID NO: 51) | 635 | ....N.............T...........R......... |
| Cry1Aa1 (SEQ ID NO: 52) | 634 | ........................................ |
| BT0003 (SEQ ID NO: 32) | 674 | KRLSDERNLLQDPNFRGINRQLDRGWRGSTDITIQGGDDV |
| Cry1Ah1 (SEQ ID NO: 51) | 675 | ............S..KD....PE...G...G.....V... |
| Cry1Aa1 (SEQ ID NO: 52) | 674 | ........................................ |
| BT0003 (SEQ ID NO: 32) | 714 | FKENYVTLLGTFDECYPTYLYQKIDESKLKAYTRYQLRGY |
| Cry1Ah1 (SEQ ID NO: 51) | 715 | ........S......................F........ |
| Cry1Aa1 (SEQ ID NO: 52) | 714 | ........................................ |
| BT0003 (SEQ ID NO: 32) | 754 | IEDSQDLEIYLIRYNAKHETVNVPGTGSLWPLSAQSPIGK |
| Cry1Ah1 (SEQ ID NO: 51) | 755 | ........V...........L...........AVK....R |
| Cry1Aa1 (SEQ ID NO: 52) | 754 | ........................................ |
| BT0003 (SEQ ID NO: 32) | 794 | CGEPNRCAPHLEWNPDLDCSCRDGEKCAHHSHHFSLDIDV |
| Cry1Ah1 (SEQ ID NO: 51) | 795 | ......--------------------.............. |
| Cry1Aa1 (SEQ ID NO: 52) | 794 | ........................................ |
| BT0003 (SEQ ID NO: 32) | 834 | GCTDLNEDLGVWVIFKIKTQDGHARLGNLEFLEEKPLVGE |
| Cry1Ah1 (SEQ ID NO: 51) | 815 | ........................KI.........L.L.. |
| Cry1Aa1 (SEQ ID NO: 52) | 834 | ........................................ |
| BT0003 (SEQ ID NO: 32) | 874 | ALARVKIAEKKWRDKREKLEWETNIVYKEAKESVDALFVN |
| Cry1Ah1 (SEQ ID NO: 51) | 855 | ......K................................D |
| Cry1Aa1 (SEQ ID NO: 52) | 874 | ......R................................. |
| BT0003 (SEQ ID NO: 32) | 914 | SQYDQLQADTNIAMIHAADKRVHSIREAYLPELSVIPGVN |
| Cry1Ah1 (SEQ ID NO: 51) | 895 | ...NR..T...............R................ |
| Cry1Aa1 (SEQ ID NO: 52) | 914 | ........................................ |
| BT0003 (SEQ ID NO: 32) | 954 | AAIFEELEGRIFTAFSLYDARNVIKNGDFNNGLSCWNVKG |
| Cry1Ah1 (SEQ ID NO: 51) | 935 | .........L....................Y......... |
| Cry1Aa1 (SEQ ID NO: 52) | 954 | ........................................ |
| BT0003 (SEQ ID NO: 32) | 994 | HVDVEEQNNQRSVLVVPEWEAEVSQEVRVCPGRGYILRVT |
| Cry1Ah1 (SEQ ID NO: 51) | 975 | .........H.....I........................ |
| Cry1Aa1 (SEQ ID NO: 52) | 994 | ...............L........................ |
| BT0003 (SEQ ID NO: 32) | 1034 | AYKEGYGEGCVTIHEIENNTDELKFSNCVEEEIYSNNTVT |
| Cry1Ah1 (SEQ ID NO: 51) | 1015 | .................D..............V.P..... |
| Cry1Aa1 (SEQ ID NO: 52) | 1034 | ..................................P..... |
| BT0003 (SEQ ID NO: 32) | 1074 | CNDYTVNQEEYGGAYTSRNRGYNEA----PSVPADYASVY |
| Cry1Ah1 (SEQ ID NO: 51) | 1055 | .....AT....E.T........DG.YESNS........A. |
| Cry1Aa1 (SEQ ID NO: 52) | 1074 | ........................................ |

TABLE 4C

| Continued Alignment of BT-0003 with Cry1Ah1 and Cry1Aa1. | | |
|---|---|---|
| BT0003 (SEQ ID NO: 32) | 1110 | EEKSYTDGRRENPCEFNRGYRDYTPLPVGYVTKELEYFPE |
| Cry1Ah1 (SEQ ID NO: 51) | 1095 | ...A......D....S...........A............ |
| Cry1Aa1 (SEQ ID NO: 52) | 1110 | ........................................ |
| BT0003 (SEQ ID NO: 32) | 1150 | TDKVWIEIGETEGTFIVDSVELLLMEE |
| Cry1Ah1 (SEQ ID NO: 51) | 1135 | ........................... |
| Cry1Aa1 (SEQ ID NO: 52) | 1150 | ........................... |

Example 6. Vectoring of Genes for Plant Expression

Prior to expression in plants, synthetic polynucleotides comprising a nucleotide sequence encoding the mutant Cry proteins, mBT-0001 and mBT-0003 (SEQ ID NOs:41 and 42, respectively) was synthesized on an automated gene synthesis platform (Genscript, Inc., Piscataway, N.J.). For this example, a first expression cassette was made comprising a maize ubiquitin promoter (Ubil) operably linked to the Cry protein coding sequence which was operably linked to a Nos terminator and a second expression cassette was made comprising a Ubil promoter operably linked to a phosphomannose isomerase (PMI) coding sequence which was operably linked to a Nos terminator. Expression of PMI allows for positive selection of transgenic plants on mannose. Both expression cassettes were cloned into a suitable vector for *Agrobacterium*-mediated maize transformation.

Example 7. Expression and Activity of Cry Proteins in Maize Plants

Transformation of immature maize embryos was performed essentially as described in Negrotto et al., 2000, Plant Cell Reports 19: 798 803. Briefly, *Agrobacterium* strain LBA4404 (pSB 1) comprising an expression vector described in Example 5 is grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* cells are suspended in LS-inf media supplemented with 100 µM As. Bacteria are pre-induced in this medium for approximately 30-60 minutes.

Immature embryos from an inbred maize line are excised from 8-12 day old ears into liquid LS-inf+100 µM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/l) and silver nitrate (1.6 mg/l) and cultured in the dark at approximately 28° C. for 10 days.

Immature embryos, producing embryogenic callus are transferred to LSD1M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the PMI genes and the Bt cry gene by PCR. Positive plants from the PCR assay are transferred to a greenhouse for further evaluation.

Transgenic plants are evaluated for copy number (determined by Taqman analysis), protein expression level (determined by ELISA), and efficacy against insect species of interest in leaf excision bioassays. Specifically, plant tissue (leaf or silks) is excised from single copy events (V3-V4 stage) and infested with neonate larvae of a target pest, then incubated at room temperature for 5 days. Leaf disks from transgenic plants expressing BT-0001 were tested against European corn borer (*Ostrinia nubilalis*), corn earworm (*Helicoverpa zea*) and black cutworm (*Agrotis ipsilon*). Leaf disks from transgenic plants expressing BT-0003 were active against at least Asian corn borer (*Ostrinia furnacalis*) and black cutworm (*Agrotis ipsilon*).

Results of the transgenic plant tissue bioassay confirm that the Cry proteins of the invention when expressed in transgenic plants are toxic to target insects. For example, BT-0001 expressed in maize stably transformed with a chimeric gene of the invention was active against at least European corn borer (*Ostrinia nubilalis*), corn earworm (*Helicoverpa zea*) and black cutworm (*Agrotis ipsilon*). BT-0003 was active against at least Asian corn borer (*Ostrinia furnacalis*) and black cutworm (*Agrotis ipsilon*).

What is claimed is:

1. A method of controlling a Cry1Ab-resistant lepidopteran insect comprising delivering to the Cry1Ab-resistant insect an effective amount of an insecticidal protein comprising SEQ ID NO:31.

2. The method of claim 1, wherein the Cry1Ab-resistant insect is sugarcane borer (*Diatraea saccharalis*).

3. A method of preventing the development of resistance in a population of sugarcane borer (*Diatraea saccharalis*) to a Cry1Ab protein expressed in a transgenic plant comprising stacking in the transgenic plant in addition to the Cry1Ab protein a second insecticidal protein comprising SEQ ID NO:31.

* * * * *

SEQUENCE LISTING

```
<160> NUMBER OF SEQ ID NOS: 52

<210> SEQ ID NO 1
<211> LENGTH: 3546
<212> TYPE: DNA
<213> ORGANISM: Bacillus thuringiensis

<400> SEQUENCE: 1

atggataaca atccgaacat caatgaatgc attccttata attgtttaag taaccctgaa     60

gtagaagtat taggtggaga aagaatagaa actggttaca ccccaatcga tatttccttg    120

tcgctaacgc aatttctttt gagtgaattt gttcccggtg ctggatttgt gttaggacta    180

gttgatataa tatggggaat ttttggtccc tctcaatggg acgcatttct tgtacaaatt    240

gaacagttaa ttaaccaaag aatagaagaa ttcgctagga accaagccat ttctagatta    300

gaaggactaa gcaatcttta tcaaatttac gcagaatctt ttagagagtg ggaagcagat    360

cctactaatc cagcattaag agaagagatg cgtattcaat tcaatgacat gaacagtgcc    420

cttacaaccg ctattcctct tttgcagtt caaaattatc aagttcctct tttatcagta    480

tatgttcaag ctgcaaattt acatttatca gttttgagag atgtttcagt gtttggacaa    540

aggtggggat ttgatgccgc gactatcaat agtcgttata atgatttaac taggcttatt    600

ggcaactata cagattatgc tgtgcgctgg tacaatacgg gattagagcg tgtatgggga    660

ccggattcta gagattgggt aaggtataat caatttagaa gagagctaac acttactgta    720

ttagatatcg ttgctctatt ctcaaattat gatagtcgaa ggtatccaat tcgaacagtt    780

tcccaattaa caagagaaat ttatacgaac ccagtattag aaaattttga tggtagtttt    840
```

-continued

```
cgtggaatgg ctcagagaat agaacagaat attaggcaac cacatcttat ggatatcctt    900
aatagtataa ccatttatac tgatgtgcat agaggcttta attattggtc agggcatcaa    960
ataacagctt ctcctgtagg gttttcagga ccagaattcg cattcccttt atttgggaat   1020
gcggggaatg cagctccacc cgtacttgtc tcattaactg gtttggggat tttttagaaca   1080
ttatcttcac ctttatatag aagaattata cttggttcag gcccaaataa tcaggaactg   1140
tttgtccttg atggaacgga gttttctttt gcctccctaa cgaccaactt gccttccact   1200
atatatagac aaaggggtac agtcgattca ctagatgtaa taccgccaca ggataatagt   1260
gtaccacctc gtgcgggatt tagccatcga ttgagtcatg ttacaatgct gagccaagca   1320
gctggagcag tttacacctt gagagctcca acgttttctt ggcagcatcg cagtgctgaa   1380
tttaataata taattgcatc ggatagtatt actcaaatcc ctgcagtgaa gggaaacttt   1440
ctttttaatg gttctgtaat ttcaggacca ggatttactg gtggggactt agttagatta   1500
aatagtagtg gaaataacat tcagaataga gggtatattg aagttccaat tcacttccca   1560
tcgacatcta ccagatatcg agttcgtgta cggtatgctt ctgtaacccc gattcacctc   1620
aacgttaatt ggggtaattc atccattttt tccaatacag taccagctac agctacgtca   1680
ttagataatc tacaatcaag tgattttggt tattttgaaa gtgccaatgc ttttacatct   1740
tcattaggta atatagtagg tgttagaaat tttagtggga ctgcaggagt gataatagac   1800
agatttgaat ttattccagt tactgcaaca ctcgaggctg aatataatct ggaaagagcg   1860
cagaaggcgg tgaatgcgct gtttacgtct acaaaccaac tagggctaaa aacaaatgta   1920
acggattatc atattgatca agtgtccaat ttagttacgt gtttatcgga tgaattttgt   1980
ctggatgaaa agcgagaatt gtccgagaaa gtcaaacatg cgaagcgact cagtgatgaa   2040
cgcaatttac tccaagattc aaatttcaaa gacattaata ggcaaccaga acgtgggtgg   2100
ggcggaagta cagggattac catccaagga ggggatgacg tatttaaaga aaattacgtc   2160
acactatcag gtacctttga tgagtgctat ccaacatatt tgtatcaaaa aatcgatgaa   2220
tcaaaattaa aagcctttac ccgttatcaa ttaagagggt acatcgaaga tagtcaagat   2280
ttagaagttt atttgatccg ttacaatgca aaacacgaaa cgttaaacgt gccaggtacg   2340
ggttccttat ggccacttgc agttaaaagt ccaattggaa ggtgcggtga accgaatcga   2400
tgtgcaccac ggattgagtg gaaacctgat gtagattgtt cctgcagaga cggagaaaaa   2460
tgtgcgcatc attcccatca tttctccttg gacattgatg taggatgtac agacttaaat   2520
gaggatttag gcgtatgggt gatattcaag attaagacac aagatggcca tgcgaaaata   2580
ggaaatctag aatttctcga agagaagctt ttattaggag aagcattagc acgtgtgaag   2640
aaagcggaga aaaaatggag agacaaacgc gaaaaattgg aatgggaaac aaatattgtt   2700
tataaagagg caaaagaatc tgtagatgct ttattcgtag attctcaata taatagatta   2760
caaacggata cgaacattgc gatgattcat gcggcagata aacgcgttca tcgaatccga   2820
gaagcgtatt tgccagagtt atctgtgatt ccgggtgtca atgcggctat tttcgaagaa   2880
ttagaaggtc ttattttcac cgcattctcc ctatatgatg cgagaaatgt cattaaaaac   2940
ggagatttca attatggttt atcatgctgg aatgtgaaag ggcatgtaga tgtagaagaa   3000
caaaacaacc accgttccgt ccttgttatc ccagaatggg aagcagaagt gtcccaagaa   3060
gttcgtgtct gtccaggtcg tggctatatc cttcgtgtta cagcgtacaa agagggatat   3120
ggagagggct gcgtaacgat ccatgagatc gaagacaata cagacgaact gaaattcagc   3180
```

-continued

```
aactgtgtag aagaggaagt atatccaaac aacacggtaa cgtgtaatga ttatactgcg   3240

actcaagaag aatatgaggg tacgtacact tctcgtaatc gaggatatga cggagcctat   3300

gaaagcaatt cttctgtacc agctgattat gcatcagcct atgaagaaaa agcgtataca   3360

gatggacgaa gagacaatcc ttgtgaatct aacagaggat atagggatta cacaccacta   3420

ccagctggct atgtgacaaa agaattagag tacttcccag aaaccgataa ggtatggatt   3480

gagatcggag aaacggaagg aacattcatt gtggatagcg tggaattact ccttatggag   3540

gaatag                                                              3546
```

```
<210> SEQ ID NO 2
<211> LENGTH: 3531
<212> TYPE: DNA
<213> ORGANISM: Bacillus thuringiensis

<400> SEQUENCE: 2
```

```
atggagatag tgaataatca gaatcaatgc gtgccttata attgtttgaa taatcccgaa     60

atcgaaatat tagaaggcgg aagaatatca gttggtaata ccccaattga tatttctctt    120

tcgcttactc agtttctttt gagtgaattt gtcccaggtg cggggtttgt attaggatta    180

attgatttaa tatggggatt tgtaggtcct tcccaatggg acgcatttct tgctcaagtg    240

gaacagttaa ttaaccaaag aatagcagaa gctgtaagaa atacagcaat tcaggaatta    300

gagggaatgg cacgggttta tagaacctat gctactgctt ttgctgagtg ggaaaaagct    360

cctgatgacc cagagctaag agaagcacta cgtacacaat ttacagcaac tgagacttat    420

ataagtggaa gaatatccgt tttaaaaatt caaacttttg aagtacagct gttatcagtg    480

tttgcccaag ctgcaaattt acatttatct ttattaagag acgttgtgtt ttttgggcaa    540

agatggggtt tttcaacgac aaccgtaaat aattactaca atgatttaac agaagggatt    600

agtacctata cagattatgc tgtacgctgg tacaatacgg gattagaacg tgtatgggga    660

ccggattcta gagattgggt aaggtataat caatttagaa gagagctaac acttactgta    720

ttagatatcg ttgctctatt ctcaaattat gatagtagaa gatatccaat tcgaacagtt    780

tcccaattaa caagagaaat ttatacgaac ccagtattag aaaattttga tggtagtttt    840

cgtggaatgg ctcagagaat agaacagaat attaggcaac cacatcttat ggatatcctt    900

aatagtataa ccatttatac tgatgtgcat agaggcttta attattggtc agggcatcaa    960

ataacagctt ctcctgtagg gttttcagga ccagaattcg cattcccttt atttgggaat   1020

gcggggaatg cagctccacc cgtacttgtc tcattaactg gtttggggat ttttagaaca   1080

ttatcttcac ctttatatag aagaattata cttggttcag gcccaaataa tcaggaactg   1140

tttgtccttg atggaacgga gttttctttt gcctccctaa cgaccaactt gccttccact   1200

atatatagac aaaggggtac agtcgattca ctagatgtaa taccgccaca ggataatagt   1260

gtaccacctc gtgcgggatt tagccatcga ttgagtcatg ttacaatgct gagccaagca   1320

gctggagcag tttacacctt gagagcccca acgttttctt ggcagcatcg cagtgctgaa   1380

tttaataata taattccttc atcacaaatt acacaaatac ctttaacaaa atctactaat   1440

cttggctctg gaacttctgt cgttaaagga ccaggattta caggaggaga tattcttcga   1500

agaacttcac ctggccagat ttcaacctta agagtaaata ttactgcacc attatcacaa   1560

agatatcggg taagaattcg ctacgcttct actacaaatt tacaattcca tacatcaatt   1620

gacggaagac ctattaatca gggtaatttt tcagcaacta tgagtagtgg gagtaattta   1680

cagtccggaa gctttaggac tgtaggtttt actactccgt ttaactttc aaatggatca    1740
```

-continued

```
agtgtattta cgttaagtgc tcatgtcttc aattcaggca atgaagttta tatagatcga   1800
attgaatttg ttccggcaga agtaaccttt gaggcagaat atgatttaga aagagcacaa   1860
aaggcggtga atgagctgtt tacttcttcc aatcaaatcg ggttaaaaac agatgtgacg   1920
gattatcata ttgatcaagt atccaattta gttgagtgtt tatcagatga attttgtttg   1980
gatgaaaaac aagaattgtc cgagaaagtc aaacatgcga agcgacttag tgatgagcgg   2040
aatttacttc aagatccaaa cttcagaggg atcaatagac aactagaccg tggctggaga   2100
ggaagtacgg atattaccat ccaaggaggc gatgacgtat ttaaagagaa ttacgttacg   2160
ctattgggta cctttgatga gtgctatcca acgtatttat atcaaaaaat agatgagtcg   2220
aaattaaaag cctatacccg ttatcaatta agagggtata tcgaagatag tcaagactta   2280
gaaatctatt taattcgcta caatgcaaaa catgaaacag taaatgtgcc aggtacgggt   2340
tccttatggc cgctttcagc ccaaagtcca atcggaaagt gtggagagcc gaatcgatgc   2400
gcgccacacc ttgaatggaa tcctgactta gattgttcgt gtagggatgg agaaaagtgt   2460
gcccatcatt cgcatcattt ctccttagac attgatgtag gatgtacaga cttaaatgag   2520
gacctaggtg tatgggtgat ctttaagatt aagacgcaag atgggcacgc aagactaggg   2580
aatctagagt ttctcgaaga gaaaccatta gtaggagaag cgctagctcg tgtgaaaata   2640
gcggagaaaa aatggagaga caaacgtgaa aaattggaat gggaaacaaa tatcgtttat   2700
aaagaggcaa aagaatctgt agatgcttta tttgtaaact ctcaatatga tcaattacaa   2760
gcggatacga atattgccat gattcatgcg gcggataaac gtgttcatag cattcgagaa   2820
gcttatctgc ctgagctgtc tgtgattccg ggtgtcaatg cggctatttt tgaagaatta   2880
gaagggcgta ttttcactgc attctcccta tatgatgcga gaaatgtcat taaaaatggt   2940
gattttaata atggcttatc ctgctggaac gtgaaagggc atgtagatgt agaagaacaa   3000
aacaaccaac gttcggtcct tgttgttccg gaatgggaag cagaagtgtc acaagaagtt   3060
cgtgtctgtc cgggtcgtgg ctatatcctt cgtgtcacag cgtacaagga gggatatgga   3120
gaaggttgcg taaccattca tgagatcgag aacaatacag acgaactgaa gtttagcaac   3180
tgcgtagaag aggaaatcta ttcaaataac acggtaacgt gtaatgatta tactgtaaat   3240
caagaagaat acggaggtgc gtacacttct cgtaatcgag gatataacga agctccttcc   3300
gtaccagctg attatgcgtc agtctatgaa gaaaaatcgt atacagatgg acgaagagag   3360
aatccttgtg aatttaacag agggtatagg gattacacgc cactaccagt tggttatgtg   3420
acaaaagaat tagaatactt cccagaaacc gataaggtat ggattgagat tggagaaacg   3480
gaaggaacat ttatcgtgga cagcgtggaa ttacttctta tggaggaata g             3531
```

<210> SEQ ID NO 3
<211> LENGTH: 3531
<212> TYPE: DNA
<213> ORGANISM: Bacillus thuringiensis

<400> SEQUENCE: 3

```
atggagatag tgaataatca gaatcaatgc gtgccttata attgtttgaa taatcccgaa     60
atcgaaatat tagaaggcgg aagaatatca gttggtaata ccccaattga tatttctctt    120
tcgcttactc agtttctttt gagtgaattt gtcccaggtg cggggtttgt attaggatta    180
attgatttaa tatggggatt tgtaggtcct tcccaatggg acgcatttct tgctcaagtg    240
gaacagttaa ttaaccaaag aatagcagaa gctgtaagaa atacagcaat tcaggaatta    300
```

-continued

```
gagggaatgg cacgggttta tagaacctat gctactgctt ttgctgagtg ggaaaaagct    360
cctgatgacc cagagctaag agaagcacta cgtacacaat ttacagcaac tgagacttat    420
ataagtggaa gaatatccgt tttaaaaatt caaacttttg aagtacagct gttatcagtg    480
tttgcccaag ctgcaaattt acatttatct ttattaagag acgttgtgtt ttttgggcaa    540
agatggggtt tttcaacgac aaccgtaaat aattactaca atgatttaac agaagggatt    600
agtacctata cagattatgc tgtacgctgg tacaatacgg gattagaacg tgtatgggga    660
ccggattcta gagattgggt aaggtataat caatttagaa gagagctaac acttactgta    720
ttagatatcg ttgctctatt ctcaaattat gatagtagaa gatatccaat tcgaacagtt    780
tcccaattaa caagagaaat ttatacgaac ccagtattag aaaattttga tggtagtttt    840
cgtggaatgg ctcagagaat agaacagaat attaggcaac cacatcttat ggatatcctt    900
aatagtataa ccatttatac tgatgtgcat agaggcttta attattggtc agggcatcaa    960
ataacagctt ctcctgtagg gttttcagga ccagaattcg cattcccttt atttgggaat   1020
gcggggaatg cagctccacc cgtacttgtc tcattaactg gtttggggat ttttagaaca   1080
ttatcttcac ctttatatag aagaattata cttggttcag gcccaaataa tcaggaactg   1140
tttgtccttg atggaacgga gttttctttt gcctccctaa cgaccaactt gccttccact   1200
atatatagac aaaggggtac agtcgattca ctagatgtaa taccgccaca ggataatagt   1260
gtaccacctc gtgcgggatt tagccatcga ttgagtcatg ttacaatgct gagccaagca   1320
gctggagcag tttacacctt gagagcccca acgttttctt ggcagcatcg cagtgctgaa   1380
tttaataata taattccttc atcacaaatt acacaaatac ctttaacaaa atctactaat   1440
cttggctctg gaacttctgt cgttaaagga ccaggattta caggaggaga tattcttcga   1500
agaacttcac ctggccagat ttcaacctta agagtaaata ttactgcacc attatcacaa   1560
agatatcggg taagaattcg ctacgcttct actacaaatt tacaattcca tacatcaatt   1620
gacggaagac ctattaatca gggtaatttt tcagcaacta tgagtagtgg gagtaattta   1680
cagtccggaa gctttaggac tgtaggtttt actactccgt ttaacttttc aaatggatca   1740
agtgtattta cgttaagtgc tcatgtcttc aattcaggca atgaagttta tatagatcga   1800
attgaatttg ttccggcaga agtaaccttt gaggcagaat atgatttaga aagagcacaa   1860
aaggcggtga atgagctgtt tacttcttcc aatcaaatcg ggttaaaaac agatgtgacg   1920
gattatcata ttgatcaagt atccaattta gttgagtgtt tatcagatga attttgtttg   1980
gatgaaaaac aagaattgtc cgagaaagtc aaacatgcga agcgacttag tgatgagcgg   2040
aatttacttc aagatccaaa cttcagaggg atcaatagac aactagaccg tggctggaga   2100
ggaagtacgg atattaccat ccaaggaggc gatgacgtat ttaaagagaa ttacgttacg   2160
ctattgggta cctttgatga gtgctatcca acgtatttat atcaaaaaat agatgagtcg   2220
aaattaaaag cctatacccg ttatcaatta agagggtata tcgaagatag tcaagactta   2280
gaaatctatt taattcgcta caatgcaaaa catgaaacag taaatgtgcc aggtacgggt   2340
tccttatggc cgctttcagc ccaaagtcca atcggaaagt gtggagagcc gaatcgatgc   2400
gcgccacacc ttgaatggaa tcctgactta gattgttcgt gtagggatgg agaaaagtgt   2460
gcccatcatt cgcatcattt ctccttagac attgatgtag gatgtacaga cttaaatgag   2520
gacctaggtg tatgggtgat ctttaagatt aagacgcaag atgggcacgc aagactaggg   2580
aatctagagt ttctcgaaga gaaaccatta gtaggagaag cgctagctcg tgtgaaaata   2640
gcggagaaaa aatggagaga caaacgtgaa aaattggaat gggaaacaaa tatcgtttat   2700
```

```
aaagaggcaa aagaatctgt agatgcttta tttgtaaact ctcaatatga tcaattacaa   2760
gcggatacga atattgccat gattcatgcg gcggataaac gtgttcatag cattcgagaa   2820
gcttatctgc ctgagctgtc tgtgattccg ggtgtcaatg cggctatttt tgaagaatta   2880
gaagggcgta ttttcactgc attctcccta tatgatgcga gaaatgtcat taaaaatggt   2940
gattttaata atggcttatc ctgctggaac gtgaaagggc atgtagatgt agaagaacaa   3000
aacaaccaac gttcggtcct tgttgttccg gaatgggaag cagaagtgtc acaagaagtt   3060
cgtgtctgtc cgggtcgtgg ctatatcctt cgtgtcacag cgtacaagga gggatatgga   3120
gaaggttgcg taaccattca tgagatcgag aacaatacag acgaactgaa gtttagcaac   3180
tgcgtagaag aggaaatcta ttcaaataac acggtaacgt gtaatgatta tactgtaaat   3240
caagaagaat acggaggtgc gtacacttct cgtaatcgag gatataacga agctccttcc   3300
gtaccagctg attatgcgtc agtctatgaa gaaaaatcgt atacagatgg acgaagagag   3360
aatccttgtg aatttaacag agggtatagg gattacacgc cactaccagt tggttatgtg   3420
acaaaagaat tagaatactt cccagaaacc gataaggtat ggattgagat tggagaaacg   3480
gaaggaacat ttatcgtgga cagcgtggaa ttacttctta tggaggaata g            3531
```

<210> SEQ ID NO 4
<211> LENGTH: 2148
<212> TYPE: DNA
<213> ORGANISM: Bacillus thuringiensis

<400> SEQUENCE: 4

```
atgaaatcta agaatcaaaa tatgcatcaa agcttgtcta acaatgcgac agttgataaa     60
aactttacag gttcactaga aaataacaca aatacggaat tacaaaactt taatcatgaa    120
ggtatagagc cgtttgttag tgtatcaaca attcaaacgg gtattggtat tgctggtaaa    180
atccttggta acctaggcgt tccttttgct gggcaagtag ctagcctcta tagttttatc    240
ctaggtgagc tttggcccaa agggaaaagc caatgggaaa tctttatgga acatgtagaa    300
gagcttatta atcaaaagat atcgacttat gcaagaaaca aagcacttgc agatttaaaa    360
ggattaggag atgctttggc tgtctaccat gaatcgctgg aaagttggat taaaaatcgc    420
aataacacaa gaactagaag tgttgtcaag agccaataca ttaccttgga acttatgttc    480
gtacaatcat taccttcttt tgcagtgtct ggagaggaag taccactatt accaatatat    540
gctcaagctg caaatttaca cttgttgcta ttaagagatg cgtctatttt tggaaaagaa    600
tggggattat cagactcaga aatttcgaca ttctataatc gtcaagtgga aagaacatca    660
gattattccg atcattgcac gaaatggttt gatacgggct tgaatagatt aaagggctca    720
aatgctgaaa tctgggtaaa gtataatcaa ttccgtagag acatgacttt aatggtacta    780
gatttagtgg cactattcca aagctatgat acacatatgt acccaattaa aactacagcc    840
caacttacta gagaagtata tacaaacgca attgggacag tacatccgca cccaagtttt    900
acaagtacga cttggtataa taataatgca ccttcgttct ctgccataga ggctgccgtt    960
atccgaagcc cgcacctact cgattttcta gaacaagtta caatttacag cttattaagt   1020
cgatggagta acactcagta tatgaatatg tggggaggac ataaactaga attccgaaca   1080
ataggaggaa cgttaaatac ctcaacacaa ggatctacta atacttctat taatcctgta   1140
acattaccgt tcacgtctcg agacatctat aggactgaat cattggcagg gctgaatcta   1200
tttttaactc aacctgttaa tggagtacct agggttgatt ttcattggaa attcgtcaca   1260
```

```
catccgatcg catctgataa tttctattat ccagggtatg ctggaattgg gacgcaatta   1320

caggattcag aaaatgaatt accacctgaa acaacaggac agccaaatta tgaatcttat   1380

agtcatagat tatctcatat aggactcatt tcagcatcac atgtgaaagc attggtatat   1440

tcttggacgc atcgtagtgc agatcgtacg aatacaattc attcagatag tataacacaa   1500

ataccactgg taaaagcaca tacccttcag tcaggtacta ctgttgtaaa agggccaggg   1560

tttacaggtg gagatatcct ccgacgaact agtggaggac catttgcttt tagtaatgtt   1620

aatttagact ggaacttgtc acaaagatat cgtgctagaa tacgctatgc ttctactact   1680

aatctaagaa tgtacgtaac gattgcaggg gaacgaattt ttgctggtca atttaataaa   1740

acaatgaata ctggtgatcc attaacattc caatctttta gttacgcaac tattgataca   1800

gcatttacat tcccaacgaa agcgagcagc ttgactgtag gtgctgatac ttttagctca   1860

ggtaatgaag tttatgtaga tagatttgaa ttgatcccag ttactgcaac acttgaggca   1920

gtaactgatt tagaaagagc gcagaaggcg gttcatgaac tgtttacatc tacgaatccg   1980

ggaggattaa aaacggatgt agccaaagat cattacacaa ataccattag taaaagcgtt   2040

caatctgtct tcaggtgccg ctgtagtgag aggaccagga tttacaggtg gggatatcct   2100

tcgaagaaag aatactggta catttgggga tatacgagta aatattaa                2148
```

<210> SEQ ID NO 5
<211> LENGTH: 3285
<212> TYPE: DNA
<213> ORGANISM: Bacillus thuringiensis

<400> SEQUENCE: 5

```
atgtttcttg aacaaattga acaactaatt gaccagagaa tagagacagt cgaaaggaat     60

agggcaattc aaacattaat tgggttatca aatagttatg atgtatatat tgaagcgtta    120

aaagaatggg aaaataatcc tgataattca gcttcacaag aaagagtacg taatcgcttt    180

cggacaactg acgatgcttt gataactggc attcctcttt tagccattcc gaattttgaa    240

atagctactt tatcggtgta tgttcaagct gccaatctac atttatcctt attaagggat    300

gcagtgtttt tcggagaaag atggggatta acacaaataa atgtagatga cttgtacagg    360

agattaacga ataatatcag aaactattca gatcattgtg cacgatggta taatgaagga    420

ttagataata tttctggttt atctcgatct attaacttcc aaagagaagt aacaatctct    480

gtcttagata ttgttgcgct ttcccgaac tatgacatcc gaacatatcc aatttcaaca    540

acaagccaat taacaaggga gatattcaca tctccaattg ttgtccctaa tgattttagt    600

gtagcctacg agggggtaag gagagcgcca cacctatttg aatttttaga gaaacttgtt    660

atttataccg gtgatcgaag tggattcgc cattgggcgg gacatgaaat aacttctaga    720

cgtactgatt cataccacgg tataattcgt taccctcttt atggaacagc agcaaatgca    780

gaaagtccat atactcttgc ccttcaacct tctgaaagta tttatagaac gttatcagaa    840

cctatatttt cacaaactgg tgggctgtct cctcatagaa ggagagtagt agagggagta    900

gagttctcta ttgtaaataa taacgtaaat ccttcgtcat ttgtatatag aagaaagggt    960

tcgttagatt cttttactga gttaccacct gaagatgaaa gtgtaccacc ttatattggc   1020

tacagtcatc aattatgcca tgttggattt ggtcgtacaa atgtaatctt tgaaccaagt   1080

aatttcgcta gggttccagt attctcctgg acacatcgta gtgcaacccc tacaaataca   1140

attgatccag atagaattac ccaaatacct tcagtgaagg cgagttctct tcgtaattct   1200

actgttgtta gtggaccagg atttactgga ggggatattg ttcgaatggg agcagtgcac   1260
```

```
caaatatatg caacggattt aagtatgaat gttcgaccta gtgttgcatt gagcagatat   1320

cttataagac ttcgctatgc ttgtaggggg agttcaaaca tagttataca cggtccttct   1380

attagatttg tatcgctccc aagtacaatg agtaatgatg aacctttaac atatcaatca   1440

tttagatacg caagtatcac aactccaatt acccgtccaa tatataacat gtttaattta   1500

tctatatcca gaatttcagg tgtccaaaat ttgtttatag atcgaataga attcattcca   1560

gtagatgcaa acttcgaagc agaacgagat ttagagagag cgcagaaggc ggtgaatgct   1620

ctgtttactt ccacaaacca aagaggacta aaaatagatg tgactgacta tcatattgat   1680

caagtatcca atttagttga ttgcttatcg gatgaatttt gtctggatga aaagcgagaa   1740

ttgtccgaaa aatccaaaca tgcgaagcga ctcagtgatg aacgcaattt actccaagat   1800

ttaaatttca aagacattaa taggcaacca gaacgtggtt ggagcggaag tacagggatt   1860

accatccaag gaggagatga cgtattcaaa gagaattacg ttacactacc aggtaccttt   1920

gatgagtgct atccaacata tttgtatcaa aaaatcgatg aatcaaaatt aaaagcctat   1980

acccgctatc aattaagagg atacatcgaa gatagtcaag acttagaaat ctatttaatt   2040

cgctacaatg caaaacatga gacagtaaat gttcctggct ctggctcctt atggccactt   2100

tcagtcgaaa gctcagttgg aaaatgcgga gagccaaatc gatgtgcatc acggatggaa   2160

tggaatcccg acctagattg ctcgtgtagg gatggggaga agtgtgccca tcattcccat   2220

catttctctt tggacattga tgtaggatgt acagacttaa atgaggattt aggtgtatgg   2280

gtgatattca agattaagac acaagatggc catgcgaaaa taggaaatct agaatttctc   2340

aaagagaagc tgttattagg agaagcatta gcacgtgtga agaaagcgga gaaaaaatgg   2400

agagacaaac gcgacaaatt ggaatgggaa acaaatgttg tttataaaga ggcaaaagaa   2460

tctgtagatg ctttattcgt agattctcaa tatagtagat tacaagcgga tacgaacatc   2520

gcaatgattc atgcggcaga taaacgcgtt catcgaattc gagaagcgta tctcccagaa   2580

ctaactgtga ttccaggtgt caatgcatct attttcgaag aattagaggg acgtattttc   2640

acagcgtatt ccctatatgg tgcaagaaat gtcataaaaa atggcgattt caataatggt   2700

ttatcttgct ggaacgtgaa agggcatgta gaggtacaac agattcatca tcgttcggtt   2760

cttgttgttc caagttggaa aacagaagta tcacaagagg tgtgcgtctg tccaggacgt   2820

ggctatatcc ttcgtgttac agcgtacaaa gaaggatatg gagaaggcaa cgtaaccatc   2880

catgagatcg agaacaatac agatgaactg aagtttagaa actgtgaaga agaggaagtc   2940

tatccaaaca acacagtaac gtgtaatgat tatactgtaa atcaagaaga atataagggt   3000

acgtgcactt ctcgtaatcg aggatatgac gaatcctatg aaagcagctc ttccgaatca   3060

gcttattatg cttcagtcta tgaagaaaaa gggtatacag atggacgaag agagaatctt   3120

tgtgaattta ataggggggta tggggattac acgtcactac caactgctta tgtgacaaaa   3180

gaattagagt acttcccaga aaccgataag gtatggattg agattggaga aacagaagga   3240

gcattcatcc tggacagcgt ggaattactc cttatggagg aataa                    3285
```

<210> SEQ ID NO 6
<211> LENGTH: 3510
<212> TYPE: DNA
<213> ORGANISM: Bacillus thuringiensis

<400> SEQUENCE: 6

```
atggagatta ataatcagaa ccaatgtgtc ccttataatt gtttgaataa tcctgaaagc     60
```

-continued

```
gagatattaa acgttgcaat ttttagtagc gaacaggtag cagaaattca cttaaagatc    120
acgcgcttaa ttttagagaa ttttttacca ggtgggagtt ttgcattcgg cttatttgat    180
ttaatatggg ggatttttaa tgaagatcaa tggagcgcat ttcttcggca ggtagaagaa    240
ttaattaatc aaaggataac ggaattcgca agagggcaag caattcagag actagtaggg    300
tttggaagga gttatgatga atatatttta gcactaaaag aatgggaaaa cgatcctgat    360
aacccagctt caaaggaaag agtgcgcact cgatttcgga caactgatga tgccttgcta    420
accggtgttc ctcttatggc aattccaggt tttgaattag ctactttatc tgtttatgct    480
caatcagcca atctacattt agccctatta agagatgctg tatttttgg ggagagatgg     540
ggattgacac aaacaaatat aaatgattta tatagtagat taaaaaactc cattcgtgat    600
tatacaaatc attgtgttcg tttttataat ataggtttag ggaatttaaa tgttataaga    660
ccagagtatt accgtttcca aagagaatta acaatatctg tcttagatct tgtagctctt    720
tttccaaatt acgatatccg aacatatcca ataccaacta aaagtcaatt aacaagagaa    780
atttatacag atccgattat ttcacctggt gcacaggcag gttatactct tcaagatgtt    840
ttgagagaac cacaccttat ggacttttta aaccgactta ttatttatac tggtgagtat    900
cgcggaattc gtcactgggc aggacatgaa gtagaatcta gtagaacagg tatgatgact    960
aatataagat ttcctttgta tggaacagcc gcaacagcag aaccaacacg atttataact   1020
cctagtactt ttcctggtct taatttattt tatagaacat tatcagctcc tatttttaga   1080
gatgaaccgg gagctaatat tattattaga tatagaacga gtttggtgga aggagtagga   1140
tttattcaac caaataacgg tgaacagctt tacagagtga gaggaacatt agattctctt   1200
gatcaattac cacttgaggg tgagagtagt ctaactgaat atagtcatcg attatgccat   1260
gttagatttg cgcaatcatt gaggaatgca gaacctttag attatgcaag ggttccgatg   1320
ttttcttgga cacatcgtag tgcaacccct acaaatacaa ttgatccaga tgtcatcacc   1380
caaataccgt tagtaaaggc tttcaatctt cattcaggtg ccacgattgt taaaggacca   1440
ggttttacag gtggggatat ccttcgaaga acgaatgttg gtagctttgg agatatgcgt   1500
gtaaacatta ctgcaccact atcacaaaga tatcgcgtaa ggattcgtta tgcttctacg   1560
acagatttac aattctatac gaatattaat ggaactacta ttaatattgg taatttctcg   1620
agcactatgg acagtgggga tgatttacag tacggaagat tcagggttgc aggttttact   1680
actccattta ccttttcaga tgcaatgagc acattcacaa taggtgcttt tagcttctct   1740
tcaaacaacg aagtttatat agatcgaatt gaatttgtcc cggcagaagt aacatttgag   1800
gcagaatatg atttagagaa agctcagaaa gcggtgaatg cgctgtttac ttcttccaat   1860
caaatcgggt taaaaacaga tgtgacggac tatcatattg ataaagtatc caatctagtt   1920
gagtgtttat cagatgaatt ttgtctagat gaaaagcgag aattgtccga gaaagtcaaa   1980
catgcgaagc gactctgtga tgagcggaat ttacttcaag atccaaactt cagaggcatc   2040
aatagacaac cagaccgtgg ttggagagga agtacggata ttaccatcca aggaggagat   2100
gacgtattca aagagaatta cgttacgcta ccgggtacct ttgatgagtg ctatccaacg   2160
tatttatatc aaaaaataga tgagtcgaaa ttaaaagcct atacccgcta tgaattaaga   2220
gggtatatcg aggatagtca agacttagaa atctatttaa ttcgctacaa tgcaaaacat   2280
gaaacagtaa atgtgccagg tacgggttcc ttatggccgc tttcagccca aagtccaatc   2340
ggaaagtgtg gagaaccgaa tcgatgtgcg acacaccttg aatggaatcc tgacttagat   2400
tgttcgtgta gggatggaga aaagtgtgcc catcattcgc atcatttctc cttagacatt   2460
```

```
gatgtaggat gtacagacct aaatgaggac ctaggtgtat gggtgatctt taagattaag   2520
acgcaagatg gtcatgcgag actaggaaat ctagaatttc tcgaagagaa accattagta   2580
ggagaagcgc tagctcgtgt gaagagagcg gagaaaaaat ggagagacaa acgcgaaaaa   2640
ttggaattgg aaacaaatat tgtttataaa gaggcaaaaa aatctgtaga tgctttattt   2700
gtgaactctc aatatgatag attacaagcg gatacgaata tcgcgataat tcatgcggca   2760
gataaacgcg ttcatagcat tcgagaagca tatcttccag agttgtctgt aattccgggt   2820
gtaaatgcag ctatttttga agaattagag ggacgtattt tcacagccta ctctctatat   2880
gatgcgagaa atgtcattaa aaatggcgat ttcaataatg gcttatcatg ctggaacgtg   2940
aaagggcatg tagatgtaga agaacagaac aaccatcgtt cggtccttgt tgttccagaa   3000
tgggaagcag aagtgtcaca agaggttcgt gtctgtccag gtcgtggcta tatccttcgt   3060
gttacagcgt acaaagaggg atatggagag ggctgtgtaa cgattcatga gatcgaagac   3120
aatacagacg aactgaaatt cagcaactgt gtagaagagg aaatatatcc aaacaacacg   3180
gtaacgtgta atgattatac tgcgactcaa gaagaatatg agggtacgta cacttctcgt   3240
aatcgaggat atgacggagc ctatgaaagc aattcttctg taccagctga ttatgcatca   3300
gcctatgaag aaaaagcgta tacagatgga agaagagaca atacttgtga atctaacaga   3360
ggatatgggg attacacacc actaccagct ggctatgtga caaaagaatt agagtacttc   3420
ccagaaaccg ataaggtatg gattgagatt ggagaaacgg aaggaacatt tatcgtggac   3480
agcgtggaat tactccttat ggaggaatag                                    3510
```

<210> SEQ ID NO 7
<211> LENGTH: 3414
<212> TYPE: DNA
<213> ORGANISM: Bacillus thuringiensis

<400> SEQUENCE: 7

```
atggaagtaa atcatcaaaa tgaatgtgta ccctataatt gtttaaagaa tcccaagatt     60
gagatgttag atatcgaggg aataagtagt agaagtagag aacaagtagc ggaaattagc    120
ttagggctca cgcgctttct tttggagtca ctgctccctg gtgcaagttt tggatttggt    180
ttatttgata tcatttgggg agttattggt cctgatcaat ggagcctatt tcttacacaa    240
attgaacaat taattgatca acggatagag gcacatgtaa gaaatcaagc gattagtaga    300
ttagaagggc ttggagatag ttatgaagtg tatattgagt cgcttagaga atgggaggcg    360
tctcctaata atgaatcctt gcagcaggat gtgcgtaatc gatttagtaa taccgataat    420
gccttgatta ccgcgatacc tatcctgaga gaacagggct ttgaaattcc tcttttaacg    480
gtttatgttc aggctgccaa tttgcattta tccttattaa gggatgccgt atattttgga    540
cagagatggg gacttgatac agctacagta aacaatcatt ataatcgatt aattaatctt    600
attaacactt attccgatca ttgtgctcaa tggttcaata gaggtctgga taattttggt    660
gttgtaacag caagatattt agatttccaa agagaggtaa caatatctgt cttagatatc    720
gttgctcttt tcccgaatta tgatattcgg acatatccaa tccaaacact aagtcaatta    780
acaagagaaa tttatacatc tccagttgct gaacctggtg caagtttaaa tgtggatttg    840
cggaatatat tgagagaacc tcacctaatg gattttttaa ctcgccttgt tatttatacg    900
ggtgtgcagg gtggtattta tcattgggca ggacatgaga tatcttctag gactacaggt    960
aatttatcga gcaacatcca attcccacta tatggaacat ccgcaaatgc agataggcca   1020
```

-continued

```
tttaatttag ccattcacta ttctgaaaca atttatagaa cattatcagc ccctatttat   1080
tcggtttctg gtggtatttc tcctaataga acgagagcag tggaaggggt aaggttctta   1140
accgcaagag ataataatct aaattccttg ccatttttat atagaaaaga aggttcttta   1200
gattctttta ccgagttacc acctgaagat gagaatgaac caccttatat tgggtatagt   1260
catcggttat gccatgctag atttgctagg tcatccgtag ttcttgagcc aagtaatttt   1320
gcgagaattc cagtattttc atggacacat cgtagcgctg gccctactaa tgaagtaagt   1380
tcatctagaa taacacaaat cccatgggta aaagcacata cccttgattc aggagcattt   1440
gttataaagg gtcctggatt tacaggaggg gatattctta ctaggcctaa tttgggtacc   1500
ttaggagctt taagagtgac ccttacagga caattaccac aaacatataa tataagaatc   1560
cgatatgctt cgatagcaaa tagaggtggt acactgattt tttcacagcc accttcatat   1620
ggcctcacat ttccaaaaac aatggatata gatgagccct taacatctcg ttcgtttgct   1680
cgtacaactc ttttcacacc aataactttt acacaagcac aggccgaatt aaatctaaca   1740
atacaacagg gtgtttatat agatagaatt gaattcatcc cagttaatgc aacctttgag   1800
gcagaatatg atttagaaag agcacaaaag gcggtgaatg ctctgtttac ttcttccaat   1860
caactaggat taaaaacaga tttgacggat tatcatattg atcaagtttc caatttagtg   1920
gattgtttat ccgatgaatt ctgtatagat gaaaagcgag aattgtccga gaaagtcaaa   1980
catgcgaagc gactcagtga tgaacggaat ttactccaag attcaaactt tagaggcatc   2040
aatagacaac cagaccgtgg ctggagagga agtacggata ttaccatcca aggaggaaat   2100
gacgtattca aagaaaatta cgtcacacta ccgggtacct tcgatgaatg ttatccaacg   2160
tatttgtatc aaaaaataga tgagtcaaaa ttaaaagcct atacccgtta tcagttaaga   2220
gggtatatcg aagatagtca agacttagaa atctatttaa ttcgctacaa tgcaaaacac   2280
gaaacagtaa atgtgccagg tacgggttcc ttatggccgc tttcagtcga aagtccaatc   2340
ggaaagtgcg gagaaccgaa tcgatgtgtg ccacagcttg aatggaattc taatctagat   2400
tgttcctgca gagacggaga aaaatgtgca catcattccc atcatttctc cctagacatt   2460
gatgttggat gtacagactt acatgatgac ttaggtgtat gggtgatatt caagattaag   2520
acgcaagatg gccatgcaag actagggaat ttagagtttc tcgaagagaa accattagta   2580
ggagaagcgc tagctcgtgt gaaaagagcg gagaaaaaat ggagagacaa acgcgaaaca   2640
ttgcaattgg aaacgaatat cgtttacaaa gaggcaaaag aatctgtgga tgctttattt   2700
gcaaactctc aatataatag attacaagcg gatacgaaca tcgcaatgat tcatgcggca   2760
gataaacgcg ttcatcgaat ccgagaggct tatcttccgg aattatccgt tatcccaggt   2820
gtaaatgcgg ggatttttga agaattagaa ggtcgtattt tcactgcatt ctctttatat   2880
gatgcaagaa atgtcattaa aaacagtgat ttcaataatg gcttatcatg ctggaacgtg   2940
aaagggcatg tagatataga agaacagaac aaccaccgtt cggtccttgt tgttcctgaa   3000
tgggaagcag aagtatcaca aaaagttcat gtttgtccag gtcgtggtta tatccttcgt   3060
gtcacagcgt acaaggaggg atatggagaa ggttgcgtaa ccattcatga aattgaagat   3120
catacagatg aactaaagtt tagaaactgt gaagaagacg aagtctatcc aaacaacacg   3180
agaacgtgta atgcttatcc tgcagatcaa gaaggatatg agggggcgtg cacttctcgt   3240
aatcgtggat atgacgaagt ctatggaaac accccttccc taccagctga ttatgcgcca   3300
atttatgagg agaatgcata cacagatgga cgaagaggta atccttgtga atctagcaga   3360
gggtatgggg attacactcc actaccagct ggttatgaaa caaaggaatt agag         3414
```

<210> SEQ ID NO 8
<211> LENGTH: 2160
<212> TYPE: DNA
<213> ORGANISM: Bacillus thuringiensis

<400> SEQUENCE: 8
atgaaactaa agaatccaga taagcatcaa agcttgtcta gcaatgcgaa agtagataaa 60
atcgctacgg attcactaaa aaatgaaaca gatatagaat tgaaaaatat gaataatgaa 120
gattatttga gaatgtctga gcatgagagt attgatccgt ttgttagtgc atcaacaatt 180
caaacgggta ttggaattgc tggtaagatt cttggtactc taggtgttcc ttttgctgga 240
caaatagcta gcctctatag ttttatctta ggcgagcttt ggcctaaagg gaaaagtcaa 300
tgggaaatct ttatggaaca tgtagaagag attattaatc aaaaaatatt aacttatgca 360
agaaataaag cactttcaga cttgagagga ttaggggatg ctttagccgt ctaccatgaa 420
tcgcttgaaa gttgggttaa aaatcgtaat aacactcgag cgaggagtgt agtcaagaac 480
caatatatcg cattagaact gatgtttgtt caaaaactac cttcttttgc agtatctggt 540
gaggaagtac cattattacc gatatatgcc caagctgcca atttacattt gttgttatta 600
agagatgcat ctatttttgg aaaagaatgg ggattatcag cttcagaaat ttcaacattt 660
tataaccgtc aagtcgaacg aacaagagat tattccgacc attgtgtaaa atggtataat 720
acaggcctaa ataacttgag gggtacaaat gccaaaagtt gggttcgtta taatcaattt 780
cgtaaagata tgacattaat ggtattagat ttagttgcgc tattcccaag ctatgataca 840
cttgtatatc ctattaaaac cacttcacaa cttacaagag aagtatatac agacgcaatt 900
gggaccgtgc atccttcagg tgccgttgca agtacgactt ggtataataa taatgcacct 960
tcgttctcta cgatagaggc tgctgttgtt cgaaacccgc atctactcga ttttctagaa 1020
caagttacaa tttacagctt attaagtcga tggagtaaca ctcagtatat gaatatgtgg 1080
ggaggacata aactagaatt ccgaacaata ggaggaacgt taaatacctc aacacaagga 1140
tctactaata cttctattaa tcctgtaaca ttaccgttca cgtctcgaga cgtctatagg 1200
actgaatcat tggcagggct aaatctattt ttaactcaac ctgttaatgg agtacctagg 1260
gttgattttc attggaaatt cgtcacacat ccgatcgcat ctgataattt ctattatcca 1320
gggtatgctg gaattgggac gcaattacag gattcagaaa atgaattacc acctgaaaca 1380
acaggacagc caaattatga atcttatagt catagactat ctcatatagg actcatttca 1440
gcatcccatg tgaaagcgtt ggtatattct tggacgcatc gtagtgcaga tcgtacaaat 1500
accattaatt cagatagcat tacacaaata ccattagtaa aggcattcaa tcttccctca 1560
ggtgcttctg ttgttagagg accaggattt acaggtgggg atatccttcg aagaacaaat 1620
actggtacat ttggggatat acgagtaaat attaatccac catttgcaca acggtatcgc 1680
ttaagaattc gttatgcttc tactacaaat ttagaattcc atacgtcgat taacggaaaa 1740
gctattaatc aaggtaattt ttcagcaact atgaatagag gagaggactt agactataaa 1800
gcctttagaa ctgtaggctt tactactcca tttagctttt caaatgcaca aagtacattc 1860
acaataggtg cttggaactt ctctttaggt aacgaagttt atatagatag aattgaattt 1920
gttccggtag aagtaacata tgaggcagag catgattttg aaaaagcgca agaggaggtt 1980
actgcactgt ttacatctac gaatccaggt gggttaaaaa caaatgtaac ggagtatcat 2040
attgaccagg tatcaaattt agtagagtct ttatcaaatg aattctatct cgatgaaaag 2100

-continued agagaattat tcgagatagt taaatacgcg aagcaacttc atattgggcg taacatgtag 2160

<210> SEQ ID NO 9
<211> LENGTH: 3495
<212> TYPE: DNA
<213> ORGANISM: Bacillus thuringiensis

<400> SEQUENCE: 9
atggagagaa ataatcagga tcaatgcatt ccttataatt gtttgaataa tcctgaggtt 60
gggatattag atattgaaaa tttcaatctc gaacttgtat cgcaagtcag cgtggggctc 120
acacgttttc ttttggaagc atctatccct ggggcaggtt ttgcattggg tctattcgac 180
atcatttggg gtgctctagg cgtcgatcaa tggagcttat tccttgcgca aattgagcaa 240
ttaattaatg aaagaataac aacagtagaa aggaatagag cgattcaagc attaagtgga 300
ctatcgagta gttatgaagt atatattgag gcattaagag aatgggagaa tgatctggat 360
aatccagctt cacgagatag agtggttgca cgttttcgtg caacagataa ttctctaata 420
acagatatac ctctattgga aattccaggt tttgagatag ctactttatc agtctatact 480
caagcggcga atctacattt agctttgtta agagatgccg tttactttgg agaaagatgg 540
ggattaacac aaacaaatat tgaagatctg cacacaagac tcacgagata tattcaagaa 600
tactcagacc attgcgcaag atggtataat caaggtttga ataatattgg agggataaat 660
acaagatatt tggacttcca aagagaatta acaatttcgg tcttagatat tgtcgctctt 720
ttcccaaatt acgacatccg aacatatcca attccgacac aaagccaatt aacaagggaa 780
atatatacat ctcccgtcgt tgcacctggt gtaaattgga ttttaagtat atcgaatgta 840
ttgagagccc ctcatctgat ggattttttt gatcgaataa ttatttatac tggtacagtt 900
agaagtacac cacattggga agggcatgaa gtcatatcta gaagaacagg gcaaggaaat 960
gagatacgct cgcctttata tggagtggct gcaaacgcag aaccaccagt tactataaga 1020
cctacaggat ttactgatga gcaaagacaa gtgtatagag tactatcacg tgttgcttct 1080
tttagaaatt caggaaccaa ctttagtctg gtagatgcag catcattcct aactatattt 1140
agcgctagct caatctatag aaatggtttt gggtttaatg ctgatactat tgatgaaatt 1200
ccaattgagg ggactgatcc atatattgga tatagccatc gattatgcca tgttggattt 1260
actgcgtcat ctccatttat ctcccagtat gcaagggcgc ccgtattttc ttggacgcat 1320
cgtagtgcga cttttacaaa tacaattgat ccagagagga ttacgcaaat accaatggta 1380
aaagcataca atcttcatgc aggtgccact gttgttagag gacccgggtt tacaggtggt 1440
gatctcttac gaagaacgaa tactggtaca tttgcagata taagagtaaa tattactggg 1500
ccattatctc aaagatatcg tgtaagaatt cgctatgctt ctacgacaga tttacaattt 1560
ttcacgagaa tcaatggaac ttctgtaaat caaggtaatt tccaaagaac tatgaataga 1620
ggggataatt tagaatctgg aaactttagg actgcaggat ttagtacgcc ttttagtttt 1680
tcaaatgcgc aaagtacatt cacattgggt actcaggctt tttcaaatca ggaagtttat 1740
atagatcgaa ttgaatttgt cccggcagaa gtaacattcg aggcagaatc tgatttagaa 1800
agagcgcaaa aggcggtgaa tgccctgttt acttctacaa gccaactagg gctaaaaaca 1860
aatgtaacgg gttaccatat tgatcaagtg tccaatttag ttgcgtgttt atcggatgaa 1920
ttttgtctgg atgaaaagag agaattgtcc gagaaagtta aacatgcgaa gcgactcagt 1980
gataagcgga atttacttca agatccaaac ttcagaggga tcaataggca accagaccat 2040
ggctggagag gaagtacgga tattactatc caaggaggag atgacgtatt caaagagaat 2100

```
tacgttacgc taccgggtac ttttgatgag tgctatccaa cgtatttata tcaaaaaata   2160
gatgagtcga aattaaaagc ctatacccgt tatcaattaa gagggtatat cgaagatagt   2220
caagacttag aaatctattt aattcgttac aattcaaaac acgaaatagt aaatgtacca   2280
ggtacaggga gtttatggcc tctttctgta gaaaatcaaa ttggaccttg tggagaaccg   2340
aatcgatgcg cgccacacct tgaatggaat cctgatttac actgttcctg cagagacggg   2400
gaaaaatgtg tgcatcattc tcatcatttc tctttggaca ttgatgtcgg atgtacagat   2460
ttaaatgagg acctaggtgt atggttgata ttcaagatta agacgcaaga tggccacgca   2520
agactaggga atctagagtt tctcgaagag gaaccgttat taggcgaagc gttagcacgt   2580
gtgaagagag cggagaagaa gtggagagac aaacgcgaga aactgcagtt ggaaacaaat   2640
attgtctata aagaggcaaa agaatctgta gatgctttat ttgtaaactc tcaatatgat   2700
agattacaag cggatacgaa catcgcgatg attcatgcgg cagataaacg cgttcataga   2760
atccgggaag cgtatctgcc agagttgtct gtgattccag gtgtcaatgc ggccattttc   2820
gaagaattag agggacgtat ttttacagcg tattccttat atgatgcgag aaatgttatt   2880
aaaaatggca atttcaataa tggcttatta tgctggaacg tgaaagggca tgtagatgta   2940
gaagagcaaa acaaccaccg ttcggtcctt gttatcccag aatgggaagc agaagtgtca   3000
caaaaagttc gtgtctgtcc aggtcgtggt tatatccttc gtgttacagc gtacaaagag   3060
ggatatggag aaggttgcgt aacgatccat gagatcgaag acaatacaga cgaattaaag   3120
tttagcaact gtgtagaaga aggatatcca aacaacacgg taacgtgtaa tgagtatact   3180
atgaatcaag ggtaggaga gtgtacggat gcatgtaatg tccgtaatcg tggatatgag   3240
gatgcatatg gacacaatcc ttcaacgcct gttcattaca caacgccgta cgaagaagaa   3300
acgtatacag atgaacgaag agagaatcct tgtgaagcta acaaagggta tgtgaattac   3360
acgccactac cagttggtta tgtgacaaaa gaattagaat acttcccaga aaccgacaca   3420
gtatggattg aaattggaga aacggaagga acattcattg tggacagcgt ggaattactc   3480
cttatggagg aatag                                                    3495
```

<210> SEQ ID NO 10
<211> LENGTH: 3501
<212> TYPE: DNA
<213> ORGANISM: Bacillus thuringiensis

<400> SEQUENCE: 10

```
atgaagataa ataatcagaa ccaatgcata ccatataatt gcttaagtaa tcctgaggaa     60
gtacttttgg atggggagag gatattacct gatatcgatc cactcgaagt ttctatgtcg    120
cttttgcaat ttcttctaaa taactttgtt ccaggggggg gggttatttc aggattaatt    180
aataaaatat ggggggcttt gagaccatct gaatgggaat tatttcttgc acagattgaa    240
cagttgattg atcgaagaat agaagcagca gtaagagcaa aagcaatcgc tgaattagaa    300
ggtttaggga gaagttatca actatatgga gaggcattta aagagtggga aaaaactcca    360
gataacacag cggctcggtc tagagtaact gagagatttc gtataattga tgctcaaatt    420
gaagcaaata tcccttcgtt tcgggtttcc ggatttgaag tgccacttct atcggtttat    480
acccaagcag ctaatttgca tctcgctcta ttaagagatt ctgttgtttt tggagagaga    540
tggggattga cgactacaaa tgtcaatgat atctataata gacaagttaa gagaattgat    600
gaatatagcg atcattgtgt agatacgtat aaaacagaat tagaacgtct agagtttagc    660
```

-continued

```
tctatagcgc aatggagaat atataatcag tttagaaggg aattgacact aacggtatta    720
gatattgtcg ctcttttccc gaactatgat ggtagactgt atccgattcg aacaatttct    780
caattgacaa gagatattta tacatcccca gtaagcgaat tttattatgg tcccatttat    840
aattataata tagttggtcg ccttactgaa cagcagctaa ggcgaccaca tcttatggac    900
ttctttaact ccatgatcat gtatacgtca gataatagac gagaacatta ttggtcagga    960
cttgaaatga aggctactga tacttcagga aaccaagtgt cattcccttt agctgggact   1020
agagggaatt cagctccacc agtaactgtt agaaataatg gtgagggagt ttatagaata   1080
ttatcagagc cattttattc atcacctttt ctaggcacca gtgtgctagg aagtcgtggg   1140
gaagaatttg cttttgcatc taatactact acaagtctgc catctacaat atatagaaat   1200
cgtggaacag tagattcatt agtcagcata ccgccacaag attatagcgt accaccgcac   1260
agggggtata gtcatttatt aagtcacgtt acgatgcaca atagttctcc tatattccac   1320
tggacgcatc gtagtgcaac ccctagaaat acaattgatc cagatagtat cactcaaatc   1380
ccagtagtta aggcttcgca cctctctggt ggttcagtta taaaagggcc tggacataca   1440
ggtggagatt taataagcct acctgtaaat aactttactc atttccgaat cccatttcag   1500
gcaaacactc cacaaaggta tcgtattaga attcgttatg cggcagactc agatgggact   1560
ttggatagtg gagttttctt aagtgcagca gcaggggatg gttttaatac aacttcttat   1620
agggccacaa tgagccctgg aggttcctta acatctcgtg attttcaatt tttagattta   1680
aacacatcgt ttacctccga tgtagcatct aacttatggt tacattttat acgttatata   1740
cgaccaggga atttgtatat agatagagcg gaatttatcc cagtggatgc aaccttcgag   1800
gcaggttata atttagaaag ggcgcaaaag gcggtgaatg ccctgtttac ttctacaaac   1860
caaaaaggat tacaaacaga tgtgacggat tatcatattg atcaagtatc caatctagtt   1920
gattgtttat ctgatgagtt ttgcttagat gaaaagcgag aattgtccga gaaagtcaaa   1980
caggcgaagc gactcagtga tgagcggaat ttactccagg attcaaattt cagaggcatc   2040
aatagggaac aagaccgtgg atggagagga agtacgcata ttactatcca aggaggaaat   2100
gatgtattca aagaaaattt tgttacacta ccaggtgcct ttgatgcgtg ttatccaacg   2160
tatttgtatc aaaaaataga tgaatctaaa ttaaaagcct atacacgtta tgaattaaga   2220
ggatatatag aagatagtca agatttggat atttacttga tccgttacaa tacgaaacat   2280
gaaacattaa atgttccagg tactaagtct ccatggtcgc tttgtacgga gagcccactt   2340
ggaaagtgtg gggaaccaaa tcgatgcgca tcacaaatag aatggaatcc tgatctagac   2400
tgctcttgca gagacggaga aaaatgtgcg catcattcgc atcatttctc cttggacatt   2460
gatgttggat gtacagattt gaatgagaac ctaggtatat gggtgatatt caagattaag   2520
acacaggatg gtcatgcaag actaggaaat ctagaatttc tcgaagagaa accgttatta   2580
ggagaagcgt tagcccgtgt gaagagagcg gagaaaaaat ggagagacaa acgtgaaaaa   2640
ttgcaatcag aaacaaatat tgtttataaa gaagcaaaag aagctgtaga tggtttattc   2700
gtagattccc aatatgagag attacaagct gatacgaata tcgccatgat tcatgcggca   2760
gataaacacg ttcatcaaat ccgagaggtt tatttcccag agctttctgt gattccaggt   2820
gtcaatgcag cgattttcga agaattagaa ggccgtattt tcacagcgta ttccctatat   2880
gatgcgagaa atgtcattaa aaacggtgat ttcaataatg gcttatcatg ctggaacgtg   2940
aaagggcatg tagatgtaga agtacaaaac aaccaccgtt cagtcctagt tatcgcggaa   3000
tgggaagcag aagtttcaca agaagttcct gtctgtccag gtcgtggcta tatccttcgt   3060
```

```
gtcacagcgt acaaagaagg atatggagaa ggttgcgtaa ccattcatga gattgaagat   3120

catacagatg aactgaagtt tagaaactgt gaagaagagg aagtatatcc aaacaacaca   3180

gtaacgtgta atggttatac tgcgactcaa gaagaataca aggatgcata cacttctcgt   3240

aatcgaggat atgacgaagc ctatggaaat aacccttccg taccagcaga ttatgcgtca   3300

gtctatgaag aaaaagcgta tacagatgga cgaagagaga atccttgtga aatggaaaga   3360

ggttacacac ctttaccagt tggttatata acaaaagaat tagaatattt cccggaaacg   3420

gatacagtat ggattgagat tggagaaacg gaaggaacgt ttatcataga tagcgtggaa   3480

ttactcctca tggaggaata g                                             3501
```

<210> SEQ ID NO 11
<211> LENGTH: 3546
<212> TYPE: DNA
<213> ORGANISM: Artificial Sequence
<220> FEATURE:
<223> OTHER INFORMATION: Synthetic Cry coding sequence

<400> SEQUENCE: 11

```
atggacaata atccgaacat caatgagtgc atcccttaca actgcctgtc taaccctgag     60

gtggaggtgc tgggggcga gcgcatcgag acaggctaca ctccaatcga catttcgctg    120

tctctcacgc agttcctcct gtcggagttc gtgcctggcg ctgggttcgt gctgggcctc    180

gtcgatatca tttgggggat cttcggcccc tcccagtggg acgctttcct ggtccagatc    240

gagcagctca ttaaccagcg catcgaggag ttcgctagga atcaggccat ttcgcggctg    300

gagggcctct ctaacctgta ccagatctac gcggagtcct tccgcgagtg ggaggctgat    360

ccgaccaacc ccgccctgag ggaggagatg cggattcagt tcaacgacat gaattcggcg    420

ctgaccacgg ctatcccgct cttcgccgtc cagaactacc aggttcccct cctgtctgtg    480

tacgtccagg ccgcgaatct gcacctctca gtgctgcgcg acgtttccgt gttcgggcag    540

cgctggggct tcgacgctgc tactattaac tcccgctaca atgatctcac taggctgatc    600

ggcaactaca ccgactacgc cgtgcgctgg tacaataccg ggctcgagag ggtttggggc    660

ccggacagca gggattgggt caggtacaac cagttccgca gggagctgac cctcacggtt    720

ctggacatcg tggccctctt ctcgaactac gattctcggc gctacccaat taggaccgtg    780

agccagctga cgcgggagat ctacacaaat cctgtcctcg agaacttcga cgggtcgttc    840

aggggcatgg ctcagcgcat tgagcagaat atccgccagc cgcacctgat ggatatcctc    900

aattcgatca ccatttacac ggacgtgcac agggggttca actactggtc tggccatcag    960

atcaccgctt ctccagtcgg gttctcaggc ccggagttcg ctttcccact gttcgggaac   1020

gctggcaatg ctgctccacc cgtcctcgtt tcgctgacgg gcctcgggat cttccgcaca   1080

ctgtccagcc cactctacag gcggatcatt ctcggctctg ggcctaacaa tcaggagctg   1140

ttcgtgctcg acggcacgga gttctctttc gcgtcactga caactaacct cccatccact   1200

atttacaggc agaggggcac cgtggacagc ctcgatgtca tcccacctca ggacaactcg   1260

gtcccgccaa gggctggctt ctcacaccgc ctgtcccatg tcaccatgct cagccaggct   1320

gctggcgctg tttacactct gagggctccc accttctcct ggcagcaccg gagcgccgag   1380

ttcaacaata tcattgcgtc agattccatc acgcagattc cggcggtgaa ggggaacttc   1440

ctcttcaatg gctccgtcat tagcggcccc gggttcacag gcggggacct ggtgcgcctc   1500

aactcgtctg ggaacaatat ccagaatagg ggctacattg aggtcccaat ccacttccct   1560
```

-continued

```
agcacatcga ctcgctaccg cgtgagggtc cgctacgcta gcgtgactcc gattcatctg   1620

aacgtcaatt ggggcaattc atccatcttc tcgaacaccg tgcccgctac cgctacgtct   1680

ctggacaacc tccagtcctc cgatttcggc tacttcgagt ctgctaatgc cttcacgtct   1740

tcactcggga atatcgttgg cgtgcggaac ttctcaggga cagccggcgt tatcattgac   1800

cgcttcgagt tcatcccggt gacagccact ctggaggcgg agtacaacct cgagcgcgct   1860

cagaaggccg tgaatgcgct gttcacctcc acgaaccagc tgggcctcaa gacaaatgtc   1920

actgactacc acatcgatca agtcagcaac ctggttacct gcctctcgga cgagttctgc   1980

ctggatgaga agagggagct gagcgagaag gtgaagcatg ccaagaggct ctcagacgag   2040

cggaacctcc tgcaggactc caatttcaag gatatcaaca ggcagccaga gaggggggtgg   2100

ggcgggtcaa ccggcatcac gattcagggc ggggacgatg tcttcaagga gaactacgtt   2160

acactgagcg gcactttcga tgagtgctac ccccacttacc tctaccagaa gatcgacgag   2220

tcaaagctga aggcgttcac ccgctaccag ctccggggct acattgagga ctcccaggat   2280

ctggaggtgt acctcatccg ctacaacgcc aagcacgaga cgctgaatgt cccaggcaca   2340

gggtctctgt ggccactcgc ggttaagtca ccaattgggc gctgcggcga gccaaacagg   2400

tgcgctccta ggatcgagtg gaagcctgac gtggattgct cctgcaggga cggcgagaag   2460

tgcgctcacc atagccacca tttctcgctc gacatcgatg tcgggtgcac ggacctgaac   2520

gaggatctcg gcgtctgggt tatcttcaag attaagacac aggacgggca tgcgaagatc   2580

ggcaacctgg agttcctcga ggagaagctc ctgctcggcg aggctctggc tagggtgaag   2640

aaggccgaga agaagtggcg cgacaagagg gagaagctcg agtgggagac caacatcgtc   2700

tacaaggagg ccaaggagtc cgttgacgcg ctgttcgtgg atagccagta caacaggctc   2760

cagacagata ctaatatcgc catgattcac gctgccgaca agcgggtgca tcgcatccgc   2820

gaggcgtacc tgccagagct gagcgtgatt cctggcgtca acgcggctat cttcgaggag   2880

ctggagggcc tcattttcac ggctttctcc ctgtacgacg cccgcaacgt gatcaagaat   2940

ggggatttca actacggcct cagctgctgg aacgtcaagg gccacgtgga cgtcgaggag   3000

cagaacaatc ataggtccgt tctggtgatc ccggagtggg aggctgaagt cagccaggaa   3060

gtcagggttt gcccaggcag gggtacatc ctccgggtta ccgcctacaa ggagggctac   3120

ggggagggct gcgtgacgat ccacgagatt gaggacaaca cagatgagct gaagttcagc   3180

aattgcgttg aggaggaggt gtacccgaac aataccgtga cgtgcaacga ctacacagcc   3240

actcaggagg agtacgaggg cacctacacg tcgaggaacc gggggtacga tggcgcttac   3300

gagtctaatt ccagcgtccc agccgactac gcctcagcgt acgaggagaa ggcgtacacg   3360

gacggccgca gggataatcc ttgcgagtcc aaccggggct accgcgatta cactccactg   3420

cctgccggct acgtcaccaa ggagctggag tatttcccgg agacagacaa ggtttggatc   3480

gagattggcg agacggaggg gaccttcatt gtggattcgg ttgagctgct gctgatggag   3540

gagtag                                                              3546
```

<210> SEQ ID NO 12
<211> LENGTH: 3531
<212> TYPE: DNA
<213> ORGANISM: Artificial Sequence
<220> FEATURE:
<223> OTHER INFORMATION: Synthetic Cry Coding Sequence

<400> SEQUENCE: 12

```
atggagatcg tgaacaatca gaatcagtgc gtgccttaca actgcctcaa taatcccgag     60
```

atcgagatcc tggagggggg gcgcatttcg gtgggcaaca cgcctatcga catttccctc 120
agcctgacac agttcctcct gtctgagttc gttccaggcg ctgggttcgt gctcggcctg 180
atcgacctca tttggggggtt cgtgggcccg tcccagtggg atgctttcct cgcccaggtc 240
gagcagctga tcaaccagag gattgcggag gctgttcgga ataccgcgat ccaggagctg 300
gagggcatgg ctcgcgtgta caggacatac gccactgcgt tcgctgagtg ggagaaggct 360
ccagacgatc cagagctgag ggaggctctg aggacacagt tcacggcgac agagacttac 420
atctccggcc gcattagcgt cctcaagatc cagaccttcg aggttcagct cctgagcgtg 480
ttcgctcagg ctgctaacct ccacctgtcg ctcctgaggg acgtggtctt cttcgggcag 540
cgctggggct tctcgaccac gacagtgaac aattactaca acgacctcac tgagggcatc 600
tctacctaca cggattacgc cgtccgctgg tacaataccg ggctggagag ggtgtggggc 660
cccgacagca gggattgggt ccggtacaac cagttccgca gggagctgac actgactgtg 720
ctcgacatcg tcgcgctgtt ctcgaactac gattctcggc gctaccccat ccggacagtg 780
tcgcagctca ctcgcgagat ttacaccaac ccagtcctgg agaatttcga cgggtccttc 840
aggggcatgg ctcagcggat cgagcagaac attaggcagc cccacctcat ggacatcctg 900
aattccatca ccatttacac ggatgtgcac cgcgggttca actactggag cggccatcag 960
atcaccgctt ctccagtcgg gttctcaggc ccggagttcg ctttcccccct cttcgggaac 1020
gctggcaatg ctgctccacc cgtgctcgtc tccctgactg gcctcgggat cttcaggacc 1080
ctctccagcc cactgtacag gcggatcatt ctgggcagcg ggcctaacaa tcaggagctg 1140
ttcgtgctcg acggcacgga gttctcattc gcgtccctca ctaccaacct gccctccacg 1200
atctacaggc agcggggcac agtcgactct ctcgatgtta ttccacctca ggacaactca 1260
gtcccgccaa gggctggctt ctcacacagg ctctcccatg ttaccatgct gagccaggct 1320
gctggcgctg tgtacacgct gcgggctccg acattctcct ggcagcaccg cagcgcggag 1380
ttcaacaata tcattccgtc gtctcagatc acgcagattc ccctcacaaa gtccactaac 1440
ctgggcagcg ggacatcggt tgtgaagggc ccggggttca ctggcgggga catcctcagg 1500
aggacctcgc caggccagat ctctactctc cgcgttaata ttaccgctcc actgagccag 1560
cgctacaggg tccgcatccg ctacgcctca acgacaaacc tgcagttcca cacgtccatc 1620
gacgggaggc ctattaacca gggcaatttc tctgccacta tgtcatccgg gtcaaacctc 1680
cagtcgggct ctttccgcac cgtggggttc actaccccgt tcaacttctc caatggcagc 1740
tcggtgttca ccctgtcagc gcatgtcttc aactccggca atgaggttta catcgaccgg 1800
attgagttcg ttccggccga agtgactttc gaggcggagt acgatctcga gcgcgcgcag 1860
aaggctgtga acgagctgtt cacgtcttca aatcagatcg gcctgaagac cgacgtcacg 1920
gattaccaca ttgaccaggt ctccaacctc gttgagtgcc tgagcgacga gttctgcctc 1980
gatgagaagc aggagctgtc cgagaaggtg aagcatgcca agcgcctcag cgacgagagg 2040
aacctcctgc aggacccgaa cttccgcggc atcaataggc agctggacag gggtggagg 2100
ggcagcacag atatcactat tcagggcggg gacgatgtct tcaaggagaa ctacgttacc 2160
ctcctgggca cgttcgacga gtgctaccca acgtacctgt accagaagat cgatgagtca 2220
aagctcaagg cgtacacacg ctaccagctg cgcggctaca ttgaggacag ccaggatctc 2280
gagatctacc tgattaggta caacgccaag cacgagacgg ttaatgtgcc tggcacaggc 2340
tccctctggc cactctctgc tcagtcaccc atcgggaagt gcggcgagcc aaacaggtgc 2400

```
gctcctcatc tcgagtggaa tccggacctg gattgcagct gcagggacgg cgagaagtgc   2460
gctcaccata gccaccattt ctcgctcgac atcgatgtgg gctgcacgga cctcaatgag   2520
gatctggggg tctgggttat cttcaagatt aagacacagg acgggcacgc taggctgggc   2580
aacctcgagt tcctggagga gaagccactc gtgggcgagg ctctggctag ggtcaagatc   2640
gccgagaaga agtggaggga caagcgggag aagctggagt gggagacgaa catcgtgtac   2700
aaggaggcta aggagtcggt ggatgccctc ttcgtcaact ctcagtacga ccagctgcag   2760
gctgatacca atatcgccat gattcacgcc gcggacaagc gggtccattc gatccgcgag   2820
gcctacctcc cagagctgtc tgtgatccct ggcgtcaacg ctgccatttt cgaggagctg   2880
gagggcagga tcttcaccgc gttcagcctg tacgacgctc ggaacgtgat taagaatggg   2940
gatttcaaca atggcctctc gtgctggaac gtcaagggcc acgtggacgt cgaggagcag   3000
aacaatcagc gctctgtcct ggtcgttcct gagtgggagg ccgaggtttc acaggaagtt   3060
agggtgtgcc caggcagggg gtacatcctc cgcgtgaccg cgtacaagga gggctacggg   3120
gagggctgcg tcacgatcca tgagattgag aacaatacag acgagctgaa gttcagcaac   3180
tgcgtggagg aggagatcta ctcgaacaat accgttacgt gcaacgatta cactgtgaat   3240
caggaggagt acggcggggc ttacacctca aggaacaggg gctacaatga ggctccatcc   3300
gtccctgctg actacgctag cgtttacgag gagaagtcgt acacggatgg caggagggag   3360
aacccatgcg agttcaatcg cggctacagg gactacactc cactccctgt cggctacgtt   3420
accaaggagc tggagtattt cccagagacc gataaggtct ggatcgagat tggcgagact   3480
gaggggacat tcattgtgga tagcgtggag ctgctgctga tggaggagtg a            3531
```

<210> SEQ ID NO 13
<211> LENGTH: 3714
<212> TYPE: DNA
<213> ORGANISM: Artificial Sequence
<220> FEATURE:
<223> OTHER INFORMATION: Synthetic Cry coding sequence

<400> SEQUENCE: 13

```
atgaatagca acaggaagaa tgagaacgag atcattgacg cttcgttcat cccagccgtc     60
tcgaacgagt ctgttactat ttctaaggag tacgcgcaga ccaatcagct ccagaacaat    120
tcaattgagg acgggctgtg catcgctgag ggcgagtaca ttgatccttt cgtgtcagcg    180
tccaccgtcc agacggggat ctccattgct ggccgcatcc tgggggtcct gggcgttcca    240
ttcgctggcc agctcgcctc attctactcc ttcatcgtgg gggagctgtg gcctaagggc    300
agggaccagt gggagatctt catggagcac gttgagcagc tcgtgcgcca gcagattact    360
gctaatgcca ggaacacggc cctggctcgg ctccagggcc tggggaactc cttccgcgcc    420
taccagcaga gcctcgagga ctggctggag aataggaacg atgcccggac gcgcagcgtg    480
ctctacacac agtacatcgc gctggagctg gacttcctca acgcgatgcc actgttcgct    540
attcgcgagc aggaggttcc tctcctgatg gtgtacgctc aggcggccaa cctgcacctc    600
ctgctcctgc gcgatgcctc gctctacggg agggagttcg gcctgacttc tcaggagatc    660
cagcgctact acgagaggca ggtcgagagg acccgggact actcagatca ttgcgtgcag    720
tggtacaaca cggggctcaa caatctgagg ggcacaaacg cggagagctg ggtccgctac    780
aatcagttcc gcagggacct gaccctgggc gtcctggatc tcgttgccct cttcccgtca    840
tacgacacca ggacgtaccc catcaacaca tccgcgcagc tgactcggga ggtctacacc    900
gatgccattg ggcgactgg cgttaacatg gcttcgatga attggtacaa caataacgcc    960
```

-continued

```
ccaagcttct cggcgatcga gaccgctgtg attaggtctc ctcacctcct ggacttcctc   1020
gagcagctga agatcttctc ggcctccagc aggtggtcta acacccggca catgacgtac   1080
tggaggggcc atacgatcca gagcaggccc attcgcggcg ccctcatcac aagcactcac   1140
ggcaatacca acacgtcgat caacccagtc acgttccagt tcccttctcg ggacgtttac   1200
cgcacagagt catacgccgg ggtgctcctg tggggcatct acctcgagcc aatccacggc   1260
gtgccgacgg tcaggttcaa tttccggaac ccccagaata cgttcgagcg cggcacagcg   1320
aactactctc agccgtacga gtcacccggc ctgcagctca aggactccga gacggagctg   1380
ccgccggaga ccaccgagag gccaaactac gagtcttact cacaccggct gtcccatatc   1440
ggcatcattc tccagactag gctgaatgtg cctgtctact cctggaccca ccgcagcgct   1500
gacaggacaa acactatcgg cccaaatcgg atcacgcaga ttcctgccgt gaaggggaac   1560
ctcctgttca atggcagcgt catctcgggc ccggggttca caggcgggga cctcgtccgc   1620
ctgaataaca gcgggaataa catccagaac aggggctacc tcgaggtgcc cattcagttc   1680
acctccacga gcacacgcta cagggttcgg gtgcgctacg cttccgtgac cccccatccac   1740
ctgtcagtca actggggcaa ttccaacatt ttctcgtcta cagtgcccgc gactgctgcc   1800
agcctcgaca atctgcagtc gcgggatttc ggctacttcg agtctaccaa cgccttcaca   1860
tcagttactg ggaatgtggt cggcgtgcgc aacttctccg agaatgcgcg cgttatcatt   1920
gacaggttcg agttcatccc agtgactgcc accttcgagg cggagtacga tctggagagg   1980
gctcaggagg ccgtcaacgc gctcttcacg aatacaaacc cgaggaggct gaagacgggc   2040
gtgaccgact accacatcga tgaggtgtcg aacctcgtcg cctgcctgtc tgacgagttc   2100
tgcctcgatg agaagcgcga gctgctggag aaggtgaagt acgcgaagcg gctgagcgac   2160
gagcgcaacc tcctgcagga cccgaacttc acgtccatca ataagcagcc cgacttcatt   2220
agcacgaacg agcagtcgaa tttcacatct atccacgagc agtcagagca tgggtggtgg   2280
ggctccgaga acatcaccat tcaggagggc aacgatgttt tcaaggagaa ttacgtgacc   2340
ctcccaggca cgtacaacga gtgctaccct acgtacctgt accagaagat cggcgagtcg   2400
gagctgaagg cctacacacg ctaccagctg cgcggctaca tcgaggactc tcaggatctc   2460
gagatctacc tgattaggta caacgcgaag cacgagactc tggacgtgcc cggcaccgag   2520
tcggtctggc cgctgtctgt tgagtccccg atccgcaggt gcggcgagcc caacaggtgc   2580
gctccccatt tcgagtggaa tccggacctc gattgctcct gcagggacgg cgagaagtgc   2640
gcccaccatt cacaccattt ctccctggac attgatgtcg ggtgcatcga tctccacgag   2700
aacctgggcg tgtgggttgt gttcaagatc aagacgcagg aggggcatgc taggctgggc   2760
aacctggagt tcattgagga gaagcccctc ctgggcgagg ctctctccag ggtcaagcgc   2820
gcggagaaga agtggaggga caagcgggag aagctgcagc tcgagactaa gcgcgtgtac   2880
accgaggcta aggaggccgt ggatgcgctc ttcgtcgaca gccagtacga taggctgcag   2940
gccgacacga acatcggcat gattcacgcg gctgataagc tggtgcatcg catccgcgag   3000
gcgtacctct ccgagctgag cgttatcccg ggcgtgaacg ctgagatttt cgaggagctg   3060
gaggggcgga tcattaccgc gatctccctg tacgacgctc gcaacgtcgt taagaatggg   3120
gatttcaata acggcctcgc ctgctggaac gtcaagggcc acgtcgacgt tcagcagagc   3180
caccatcgct cggtgctggt catccccgag tgggaggctg aggtgagcca ggcggttagg   3240
gtgtgcccgg gcagggggta catcctccgc gtcaccgcgt acaaggaggg ctacggggag   3300
```

-continued

```
ggctgcgtga ctatccacga gattgagaat aacaccgacg agctgaagtt caagaactgc   3360

gaggaggagg aggtctaccc aactgacacc gggacgtgca atgattacac ggcccatcag   3420

ggcacagccg cgtgcaactc caggaatgct gggtacgagg acgcctacga ggtcgataca   3480

actgcgagcg ttaactacaa gcccacctac gaggaggaga catacactga cgtgcgcagg   3540

gataaccact gcgagtacga ccgcggctac gtcaattacc cacctctccc ggccggctac   3600

gtgacgaagg agctggagta cttccccgag acagacaagg tctggatcga gattggggag   3660

acagagggca ctttcatcgt ggatagcatt gagctgctgc tcatggagga gtaa         3714
```

<210> SEQ ID NO 14
<211> LENGTH: 2148
<212> TYPE: DNA
<213> ORGANISM: Artificial Sequence
<220> FEATURE:
<223> OTHER INFORMATION: Synthetic Cry coding sequence

<400> SEQUENCE: 14

```
atgaagtcta agaatcagaa catgcatcag agcctcagca acaacgctac tgtggataag     60

aatttcacgg gcagcctgga gaataacaca aatactgagc tgcagaattt caaccacgag    120

ggcatcgagc cattcgtctc agtttccaca attcagactg gcatcgggat tgcgggcaag    180

atcctgggca acctcggcgt gccgttcgct ggccaggttg cttccctcta cagcttcatc    240

ctgggcgagc tgtggcccaa ggggaagagc cagtgggaga ttttcatgga gcatgtcgag    300

gagctgatca atcagaagat ttcgacctac gcccggaaca aggctctggc tgacctcaag    360

ggcctggggg atgctctcgc tgtgtaccac gagtcgctgg agtcttggat caagaaccgc    420

aacaatacca ggacgcggtc tgtggtcaag tcacagtaca ttaccctcga gctgatgttc    480

gtccagtcac tgccgtcctt cgccgtttcc ggcgaggagg tgccgctcct gccaatctac    540

gctcaggctg cgaatctcca tctcctgctc ctgcgcgacg cctcgatctt cggcaaggag    600

tgggggctga gcgattcgga gatttctact ttctacaacc ggcaggtcga gcgcaccagc    660

gactactcgg atcactgcac aaagtggttc gacactggcc tcaataggct gaaggggtcc    720

aacgcggaga tctgggtgaa gtacaaccag ttccgcaggg acatgactct catggtcctc    780

gatctggttg ccctgttcca gagctacgat acacacatgt accccatcaa gaccacggct    840

cagctcacca gggaggttta cacgaacgcc attggcacag tgcacccaca tccttctttc    900

acctcaacaa cttggtacaa caataacgct ccgtctttct cagccatcga ggctgccgtc    960

attcggagcc cccatctcct ggacttcctg gagcaggtta ctatctactc cctcctgagc   1020

aggtggtcga atacccagta catgaacatg tggggcgggc acaagctcga gttccggaca   1080

attggcggga ctctgaacac atccactcag ggcagcacca atacgtcgat caacccagtc   1140

accctccctt tcacgtcaag ggacatctac cggacggagt ccctggccgg cctcaatctg   1200

ttcctcacac agccagttaa cggggtgccc agggtcgact tccactggaa gttcgtgacg   1260

catccaatcg cgtccgataa cttctactac cctggctacg ctggcattgg cacccagctc   1320

caggacagcg agaatgagct gccaccagag accacgggcc agccaaacta cgagtcctac   1380

agccacaggc tctcccatat cggcctgatt tcggcgtctc acgtgaaggc tctcgtctac   1440

tcttggaccc atcgctcagc ggacaggaca aacactatcc actcagattc catcacgcag   1500

attcctctcg tcaaggccca cacactgcag agcggcacaa ctgttgtgaa gggcccaggg   1560

ttcacgggcg gggacatcct gaggcgcaca tccggcgggc ctttcgcgtt cagcaatgtt   1620

aacctcgatt ggaatctgag ccagcgctac cgcgcccgca tccgctacgc gtcgaccacg   1680
```

-continued

```
aacctccgga tgtatgtgac gatcgcgggc gagcgcattt tcgctgggca gttcaataag   1740

accatgaaca cgggcgaccc actgaccttc cagagcttct cgtacgctac aatcgatact   1800

gccttcacct tccctacgaa ggcctccagc ctcactgtgg gcgctgacac cttctcgtct   1860

gggaacgagg tctacgtgga tcgcttcgag ctgatcccag tgaccgctac gctcgaggct   1920

gtcacggacc tggagagggc tcagaaggcc gtgcatgagc tgttcacctc cactaatcca   1980

ggcgggctga agaccgacgt cgctaaggat cactacacca acacgatctc taagtcagtt   2040

cagtcggtgt tcaggtgccg gtgctctgag cgcacgagga tctaccgctg ggctacccg    2100

tctaagaagg agtactggta catttggggc tacacctcaa agtactga                2148
```

<210> SEQ ID NO 15
<211> LENGTH: 3285
<212> TYPE: DNA
<213> ORGANISM: Artificial Sequence
<220> FEATURE:
<223> OTHER INFORMATION: Synthetic Cry coding sequence

<400> SEQUENCE: 15

```
atgttcctcg agcagattga gcagctgatc gaccagcgca ttgagaccgt cgagaggaat     60

cgggcgatcc agacgctcat tggcctgtcg aactcttacg atgtgtacat cgaggcgctc    120

aaggagtggg agaacaatcc ggacaattca gcttcccagg agcgcgtcag gaaccggttc    180

cgcaccacgg acgatgcgct catcacaggc attccgctcc tggctattcc caatttcgag    240

atcgccactc tgtcagtcta cgttcaggcg gccaacctcc acctgtccct cctgagggac    300

gctgttttct tcggcgagcg ctgggggctg acccagatca atgtggacga tctctaccgc    360

aggctgacga acaatatccg gaactactcc gatcattgcg cgcgctggta caatgagggc    420

ctcgacaaca ttagcgggct gagccggtcg atcaatttcc agcgcgaggt cacaatttcg    480

gttctcgata tcgtggccct gttcccgaac tacgacattc gcacttaccc catcagcaca    540

acttcgcagc tcaccaggga gattttcacg tcgccgatcg tggtccccaa cgacttctcc    600

gttgcctacg agggcgtgcg gcgcgctccc cacctgttcg agttcctcga gaagctcgtg    660

atctacacgg gcgatcgcag cgggatcagg cactgggccg gccatgagat tacgtctagg    720

cggacagact cataccacgg catcatccgc tacccgctct acgggacagc tgccaacgcc    780

gagtccccat acactctcgc gctgcagcct tctgagtcaa tctaccgcac cctctccgag    840

cctattttca gccagacggg cggctgtct ccgcacagga ggagggttgt ggagggcgtc     900

gagttctcaa tcgtcaacaa taacgttaac ccgtccagct tcgtgtaccg caggaagggc    960

tctctcgatt cattcacaga gctgccgccc gaggacgagt ctgtcccacc ttacatcggc   1020

tactcacacc agctctgcca tgtgggcttc gggaggacga atgtcatctt cgagccgtcg   1080

aacttcgcca gggtgcccgt cttctcgtgg acacaccggt ctgcgacacc aactaatacc   1140

atcgaccctg atcggatcac tcagattcct tccgtgaagg cgtcgtctct gcgcaactcg   1200

acagtcgttt ctggcccggg gttcactggc ggggatatcg tccgcatggg cgctgttcac   1260

cagatctacg ccaccgacct cagcatgaac gtgaggccgt cagtcgctct gtcccgctac   1320

ctcatcaggc tgcggtacgc ctgcaggggc tcatccaata tcgttattca tgggccatcc   1380

atccggttcg tgtccctccc tagcaccatg tcgaacgacg agccgctgac gtaccagtca   1440

ttccgctacg cctccatcac cacgccaatt accaggccta tctacaatat gttcaacctc   1500

tccatcagcc ggattagcgg cgtccagaat ctgttcatcg accgcattga gttcatcccc   1560
```

-continued gtggatgcga acttcgaggc tgagagggac ctggagcgcg ctcagaaggc tgtcaatgcg 1620
ctcttcacgt ccacaaacca gaggggcctg aagattgacg tgacggatta ccacatcgat 1680
caggttagca acctcgtgga ctgcctgtcg gatgagttct gcctcgacga gaagcgcgag 1740
ctgtctgaga agtcaaagca tgccaagagg ctcagcgacg agcggaacct cctgcaggac 1800
ctgaatttca aggatatcaa ccgccagccg gagagggggt ggtccggctc tactgggatc 1860
accattcagg gcggggacga tgttttcaag gagaactacg tgactctccc cggcaccttc 1920
gatgagtgct acccaaccta cctgtaccag aagatcgacg agtccaagct caaggcttac 1980
acgcgctacc agctgagggg ctacatcgag gacagccagg atctcgagat ctacctcatc 2040
aggtacaatg ccaagcacga gaccgttaac gtgccaggct caggctccct ctggcctctg 2100
tccgtcgagt cctccgttgg caagtgcggg gagccaaata ggtgcgccag ccgcatggag 2160
tggaacccag acctcgattg ctcctgcagg gacggcgaga agtgcgctca ccatagccac 2220
catttctcgc tggacatcga tgtcggctgc accgacctca acgaggatct gggggtctgg 2280
gttattttca agatcaagac gcaggacggc cacgccaaga tcgggaacct cgagttcctg 2340
aaggagaagc tgctgctggg cgaggctctg gccagggtga agaaggcgga gaagaagtgg 2400
agggacaagc gggataagct ggagtgggag accaacgtgg tctacaagga ggcgaaggag 2460
agcgtggacg ctctcttcgt cgattcccag tacagccgcc tgcaggccga tacgaacatt 2520
gcgatgatcc acgcggctga caagagggtg catcgcatca gggaggctta cctcccggag 2580
ctgaccgtga ttcccggcgt caacgcctcg atcttcgagg agctggaggg caggatcttc 2640
acggcctact ctctgtacgg cgccaggaat gtcatcaaga acggcgactt caataacggg 2700
ctctcctgct ggaacgtgaa gggccacgtg gaggtccagc agatccacca taggtctgtc 2760
ctggttgtgc cctcatggaa gacagaggtt tcccaggagg tttgcgtgtg cccaggcagg 2820
gggtacatcc tcagggtgac tgcctacaag gagggctacg gggagggcaa tgtcacaatt 2880
cacgagatcg agaataacac tgacgagctg aagttccgca attgcgagga ggaggaggtc 2940
tacccgaata acactgttac ctgcaatgac tacaccgtca accaggagga gtacaagggc 3000
acgtgcacat cccggaaccg cgggtacgac gagagctacg agtcttcatc cagcgagagc 3060
gcttactacg cctcggtgta cgaggagaag ggctacacgg atgggcggcg cgagaatctc 3120
tgcgagttca acagggggta cggcgactac accagcctcc ctacagccta cgtgactaag 3180
gagctggagt acttcccgga gacagataaa gtgtggatcg agattggcga gactgagggg 3240
gccttcatcc tggactccgt ggagctgctc ctgatggagg agtaa 3285

<210> SEQ ID NO 16
<211> LENGTH: 3510
<212> TYPE: DNA
<213> ORGANISM: Artificial Sequence
<220> FEATURE:
<223> OTHER INFORMATION: Synthetic Cry coding sequence

<400> SEQUENCE: 16
atggagatca acaatcagaa ccagtgcgtc ccgtacaatt gcctcaacaa tcccgagtcc 60
gagatcctga acgtggccat tttctccagc gagcaggtcg cggagattca cctcaagatc 120
acccgcctga ttctcgagaa cttcctgccg ggcgggtctt tcgctttcgg cctgttcgac 180
ctcatttggg ggatcttcaa tgaggatcag tggtcagcgt tcctcaggca ggtggaggag 240
ctgatcaacc agaggattac ggagttcgct aggggccagg ctatccagag gctggtgggc 300
ttcgggaggt cctacgacga gtacattctg gctctcaagg agtgggagaa cgacccggat 360

-continued

```
aatcccgcca gcaaggagag ggttcggaca cgcttcagga ccacggacga tgccctcctg    420
actggcgtgc cactcatggc tatccctggg ttcgagctgg ctaccctctc ggtctacgct    480
cagtcggcca acctgcacct cgccctcctg agggacgctg tgttcttcgg ggagaggtgg    540
ggcctcaccc agacgaacat caatgacctc tactcgcggc tgaagaactc tattcgcgat    600
tacaccaatc attgcgttag gttctacaac atcggcctgg ggaacctcaa tgtgattcgg    660
ccagagtact accggttcca gcgcgagctg acgatcagcg ttctggacct cgtggcgctg    720
ttccctaact acgatatccg gacttacccg attcccacca agtcccagct cacgcgcgag    780
atctacacag acccaatcat ttcgccgggg gcccaggccg gctacacact ccaggacgtc    840
ctgagggagc cgcacctgat ggatttcctg aaccggctca tcatctacac tggggagtac    900
cggggcatcc ggcactgggc tggccatgag gtggagtcgt ctcgcactgg catgatgacc    960
aacatccgct tccccctcta cggcacggcg gccacagccg agccaacacg cttcattact   1020
ccgtcgacct tccccggcct gaatctcttc taccggactc tgtcggcccc catcttccgc   1080
gacgagccgg gcgctaacat cattatccgc taccgcacct ccctggtgga gggcgttggg   1140
ttcatccagc cgaacaatgg cgagcagctg tacagggtgc ggggcaccct cgactccctg   1200
gatcagctgc cctcgagggg cgagtcatcc ctcacggagt actcacacag gctgtgccat   1260
gtccggttcg ctcagtccct ccggaacgcg gagccactgg actacgcccg ggtgcctatg   1320
ttctcatgga cacaccgctc cgccacacca actaatacca tcgaccctga tgttattact   1380
cagatcccac tcgtgaaggc gttcaacctg cattcgggcg ctactatcgt caagggccct   1440
gggttcaccg gcggggacat tctgcgcagg acgaatgttg ggtctttcgg cgatatgcgc   1500
gtgaacatca cggcgcccct cagccagcgc tacagggtgc ggattcgcta cgcttcgaca   1560
actgacctgc agttctacac caacatcaat gggaccacga ttaacatcgg caatttcagc   1620
tcgacgatgg attccgggga cgatctccag tacggcaggt tccgggtggc ggggttcaca   1680
actccgttca cgttcagcga cgctatgtcg acgttcacaa tcggcgcctt cagcttctct   1740
tcaaacaatg aggtgtacat tgaccgcatc gagttcgtcc ccgctgaggt taccttcgag   1800
gccgagtacg atctggagaa ggctcagaag gccgtcaatg cgctcttcac gtccagcaac   1860
cagatcggcc tgaagacgga cgtgacagat taccacattg acaaggtgag caacctcgtc   1920
gagtgcctgt cggacgagtt ctgcctcgat gagaagaggg agctgtccga gaaggtcaag   1980
catgcgaagc gcctctgcga cgagaggaac ctcctccagg acccgaactt ccgcggcatc   2040
aatcggcagc ctgaccgcgg gtggaggggc tccactgata ttaccatcca gggcggggac   2100
gatgtgttca aggagaacta cgtcacgctc ccgggcacat tcgacgagtg ctaccccaca   2160
tacctgtacc agaagatcga tgagtcaaag ctcaaggcct acactcggta cgagctgcgc   2220
ggctacatcg aggactccca ggatctcgag atctacctca tccgctacaa tgcgaagcac   2280
gagactgtta acgtgccagg caccgggtcg ctgtggcccc tctcggcgca gtccccaatc   2340
gggaagtgcg gcgagccaaa tcgctgcgcg acccatctcg agtggaaccc tgacctggat   2400
tgcagctgca gggacggcga gaagtgcgct caccattctc accatttctc actggacatc   2460
gatgtgggct gcaccgacct caacgaggat ctgggcgtct gggttatttt caagatcaag   2520
acccaggacg ggcacgctag gctgggcaac ctcgagttcc tcgaggagaa gccgctggtg   2580
ggcgaggctc tggctagggt taagagggcg gagaagaagt ggagggacaa gcgggagaag   2640
ctggagctgg agacaaacat cgtctacaag gaggcgaaga agtctgtcga tgctctcttc   2700
```

```
gttaattcac agtacgacag gctgcaggcc gatacgaaca tcgcgattat ccacgctgcc   2760

gacaagcggg tgcattccat tcgcgaggcc tacctcccag agctgagcgt tatccctggc   2820

gtgaacgcgg ctattttcga ggagctggag ggccgcatct tcaccgccta cagcctgtac   2880

gacgcgagga acgttattaa gaatggggat ttcaacaatg gcctctcgtg ctggaacgtg   2940

aagggccacg tggacgtcga ggagcagaac aatcatcgct ctgtcctcgt ggtcccggag   3000

tgggaggctg aggtttcaca ggaggttagg gtgtgcccgg gcagggggta catcctccgc   3060

gtcacggcgt acaaggaggg ctacggggag ggctgcgtta caattcacga gatcgaggac   3120

aatactgatg agctgaagtt ctccaactgc gtggaggagg agatctaccc aaacaatact   3180

gtcacctgca acgactacac ggccacacag gaggagtacg agggcactta caccagccgc   3240

aataggggt acgacggcgc ctacgagtcg aactcgtctg tgcctgcgga ttacgcgtct   3300

gcttacgagg agaaggctta caccgacggc aggcgcgata acacatgcga gagcaatagg   3360

gggtacggcg actacacccc actccctgcg ggctacgtga cgaaggagct ggagtacttc   3420

ccggagaccg acaaggtctg gattgagatc ggggagacgg agggcacatt catcgtggat   3480

tccgtcgagc tgctgctcat ggaggagtaa                                    3510
```

<210> SEQ ID NO 17
<211> LENGTH: 3510
<212> TYPE: DNA
<213> ORGANISM: Artificial Sequence
<220> FEATURE:
<223> OTHER INFORMATION: Synthetic Cry coding sequence

<400> SEQUENCE: 17

```
atggaggtca accaccagaa tgagtgcgtt ccatacaact gcctgaagaa tcctaagatc     60

gagatgctcg acatcgaggg catttcgtcc aggtcgaggg agcaggtggc cgagatctcc    120

ctgggcctca caaggttcct cctggagtct ctcctgccgg gcgcttcatt cggcttcggg    180

ctgttcgata tcatttgggg cgtgatcggc ccggaccagt ggtcgctgtt cctcacccag    240

attgagcagc tcatcgacca gcgcattgag gcgcacgtga ggaaccaggc tatttcgagg    300

ctggagggcc tgggggactc ctacgaggtc tacatcgaga gcctgaggga gtgggaggct    360

tccccgaaca atgagtctct ccagcaggat gtgaggaacc ggttcagcaa caccgacaat    420

gctctgatta cggccatccc gattctccgc gagcagggct tcgagatccc gctcctgacc    480

gtctacgtgc aggctgccaa cctgcacctc agcctcctgc gggatgcggt gtacttcggg    540

cagaggtggg gcctcgacac ggccacggtc aacaatcact acaaccggct gatcaacctc    600

attaatacct actccgatca ttgcgctcag tggttcaacc gcgggctgga caatttcggc    660

gtggtcactg cccgctacct cgatttccag agggaggtga ccatctcagt cctggatatt    720

gttgcgctct tcccaaacta cgacatcagg acataccta ttcagactct gtcccagctc    780

acccgggaga tctacacgtc tccagtcgcg gagcctggcg cttcactcaa cgttgacctg    840

aggaatatcc tccgggagcc acacctgatg gatttcctga cacgcctcgt gatctacact    900

ggcgtccagg gcgggatcta ccactgggct gggcatgaga tctcgtctag gaccacgggc    960

aacctgtcat ccaatatcca gttcccactg tacggcacgt ccgccaacgc tgaccggcct   1020

ttcaatctgg cgatccatta ctccgagacc atctaccgca cgctcagcgc tccaatctac   1080

tccgtcagcg gcgggatttc gccgaacagg accagggccg ttgagggcgt gcgcttcctc   1140

acagctaggg acaacaatct gaactcgctc ccgttcctgt accggaagga gggctcactg   1200

gattccttca ccgagctgcc gccggaggac gagaacgagc caccttacat cggctactcc   1260
```

cacaggctgt gccatgccag gttcgctcgc agctcggttg tgctcgagcc gtctaacttc 1320
gctcgcatcc cggtgttctc atggacccac cgctccgccg gcccgacaaa tgaggtctct 1380
tcatccagga tcactcagat tccttgggtt aaggctcata ccctggatag cggcgccttc 1440
gtgattaagg gcccggggtt caccggcggg gacatcctca ccaggccaaa cctcgggaca 1500
ctgggcgcgc tcagggtcac actgactggc cagctcccgc agacttacaa catccggatt 1560
cgctacgcct ccattgcgaa tcgcggcggc accctcatct tctctcagcc gccatcatac 1620
ggcctcacat tcccgaagac tatggacatc gatgagcccc tgacgtcgcg ctctttcgcc 1680
aggacaactc tcttcacacc aattaccttc acgcaggccc aggcggagct gaacctcact 1740
atccagcagg gcgtgtacat cgataggatt gagttcatcc ctgtcaatgc cacgttcgag 1800
gcggagtacg acctggagcg ggctcagaag gccgtgaacg cgctcttcac cagctcgaat 1860
cagctgggcc tcaagacaga cctgactgat taccacattg atcaggtgtc gaacctggtc 1920
gactgcctct ctgatgagtt ctgcatcgac gagaagcgcg agctgagcga gaaggtcaag 1980
catgccaagc ggctctcaga cgagcgcaac ctcctgcagg attccaactt caggggcatc 2040
aataggcagc cggacagggg gtggaggggc tccaccgata tcacgattca gggcgggaac 2100
gacgttttca aggagaatta cgtgaccctg ccaggcacgt tcgacgagtg ctaccctacg 2160
tacctctacc agaagatcga tgagtccaag ctgaaggcgt acacacgcta ccagctccgg 2220
ggctacatcg aggacagcca ggatctggag atctacctca tcaggtacaa cgccaagcac 2280
gagactgtta atgtgccggg caccgggagc ctgtggccac tcagcgtgga gtcgcctatc 2340
gggaagtgcg gcgagcccaa ccgctgcgtc ccacagctgg agtggaacag caatctcgac 2400
tgctcctgca gggatggcga gaagtgcgcc caccattccc accatttcag cctcgacatc 2460
gatgtggggt gcacggacct gcacgacgat ctcggcgtct gggttatttt caagatcaag 2520
acgcaggacg ggcatgctag gctgggcaac ctcgagttcc tcgaggagaa gccgctggtg 2580
ggcgaggctc tggctagggt caagagggcg gagaagaagt ggcgggacaa gcgcgagaca 2640
ctgcagctcg agactaacat cgtttacaag gaggccaagg agtcggtgga cgctctgttc 2700
gccaactctc agtacaatcg cctccaggct gatacgaaca ttgccatgat ccacgctgcc 2760
gacaagaggg tgcatcgcat ccgcgaggct tacctccccg agctgtctgt tatccccggg 2820
gtgaacgcgg gcattttcga ggagctggag ggccggattt tcaccgcctt cagcctctac 2880
gatgcgcgca acgtcatcaa gaattcagac ttcaacaatg ggctgtcctg ctggaacgtc 2940
aagggccacg ttgacatcga ggagcagaac aatcatagga gcgttctcgt cgttccggag 3000
tgggaggcgg aggtgtcgca gaaggtgcac gtctgcccgg gcagggggta catcctgcgg 3060
gtcaccgcct acaaggaggg ctacggggag ggctgcgtta ctattcacga gatcgaggac 3120
cataccgatg agctgaagtt ccgcaactgc gaggaggatg aggtgtaccc gaacaataca 3180
aggacttgca atgcgtaccc ggctgaccag gaggggtacg agggcgcctg cacttctcgc 3240
aacagggggt acgacgaggt ctacggcaat accccgtcac tccccgccga ttacgcgcca 3300
atctacgagg agaacgccta cacggacggg aggaggggca atccttgcga gtcttcacgc 3360
gggtacggcg actacacgcc actgcctgcc ggctacgaga caaaggagct ggagtacttc 3420
ccggagaccg atacggtgtg gatcaagatt ggggagacag agggcacttt catcgtcgac 3480
tccgttgagc tgctgctcat ggaggagtaa 3510

<210> SEQ ID NO 18

<211> LENGTH: 2160
<212> TYPE: DNA
<213> ORGANISM: Artificial Sequence
<220> FEATURE:
<223> OTHER INFORMATION: Synthetic Cry coding sequence

<400> SEQUENCE: 18
atgaagctca agaatccaga caagcaccag agcctgtcca gcaacgctaa ggtggacaag 60
atcgccacag attcgctcaa gaatgagact gacattgagc tgaagaacat gaacaatgag 120
gattacctcc gcatgtcgga gcatgagtct atcgaccctt tcgtttcggc ctctactatt 180
cagaccggca tcgggattgc cggcaagatc ctcggcaccc tcggcgtgcc gttcgctggc 240
cagatcgctt ctctctactc attcattctg ggcgagctgt ggcctaaggg gaagagccag 300
tgggagatct tcatggagca cgtggaggag atcattaatc agaagattct gacctacgcg 360
aggaacaagg ctctgtcgga cctcaggggc ctgggggatg ccctcgctgt ctaccatgag 420
tccctggaga gctgggttaa gaatcgcaac aatacgcggg ctcgctccgt ggtcaagaac 480
cagtacatcg ccctcgagct gatgttcgtc cagaagctgc catcgttcgc cgtgtccggc 540
gaggaggtcc cgctcctgcc aatctacgcc caggctgcca acctccacct cctgctcctg 600
cgcgacgctt ctatcttcgg caaggagtgg gggctgtcag cgtccgagat tagcacattc 660
tacaacaggc aggttgagag gactcgggac tactcggatc attgcgtgaa gtggtacaac 720
accggcctca acaatctgag gggacgaat gccaagagct gggtccggta caaccagttc 780
cgcaaggaca tgacactcat ggtgctcgat ctggtcgcgc tcttcccatc atacgacact 840
ctggtctacc ctatcaagac cacgtcccag ctgactaggg aggtttacac cgatgccatt 900
ggcacggttc accccctcagg ggcggtggcc tccacaactt ggtacaacaa taacgcgccg 960
agcttctcga ccatcgaggc tgccgttgtg cggaaccccc acctcctgga cttcctcgag 1020
caggtgacca tctactcgct cctgtctagg tggtcaaata cgcagtacat gaacatgtgg 1080
ggcgggcata agctcgagtt ccggactatc ggcggcaccc tcaacacaag cactcagggc 1140
tcgaccaata cgtctattaa cccagtgacg ctccctttca catctaggga cgtctaccgg 1200
acagagtcac tggccggcct caatctgttc ctcacgcagc ccgtgaacgg cgtccccagg 1260
gttgacttcc actggaagtt cgtcacccat ccaatcgcgt ccgataactt ctactaccct 1320
ggctacgctg gcattgggac gcagctccag gactccgaga atgagctgcc gcccgagacc 1380
accggccagc ccaactacga gtcttactca cacaggctct cccatatcgg cctgatttcc 1440
gccagccacg ttaaggcgct cgtgtacagc tggacacatc gctcggccga caggacaaat 1500
actatcaact cggattctat cacgcagatt ccgctcgtga aggccttcaa cctgccgtcg 1560
ggcgcctcgg tcgttcgggg ccccgggttc accggcgggg acatcctgcg caggaccaac 1620
acgggcacat tcggggatat ccgcgtcaat attaacccac ctttcgccca gcgctacagg 1680
ctccgcatcc gctacgcgtc cacaactaat ctggagttcc acaccagcat caacggcaag 1740
gctattaatc aggggaactt ctcggctacc atgaaccgcg gcgaggacct cgattacaag 1800
gccttcagga cggtgggctt caccacgccc ttctcattct ccaacgcgca gtcgactttc 1860
accatcggcg cttggaattt ctctctgggg aacgaggtct acatcgacag gattgagttc 1920
gtgccggtcg aggttaccta cgaggcggag cacgatttcg agaaggcgca ggaggaggtg 1980
acggctctct tcacgagcac aaatccaggc ggcctgaaga cgaacgtcac agagtaccat 2040
atcgaccagg tctcgaatct cgttgagagc ctgtcgaacg agttctacct cgatgagaag 2100
cgggagctgt tcgagatcgt gaagtacgcc aagcagctgc acattggccg caacatgtaa 2160

<210> SEQ ID NO 19
<211> LENGTH: 3495
<212> TYPE: DNA
<213> ORGANISM: Artificial Sequnece
<220> FEATURE:
<223> OTHER INFORMATION: Synthetic Cry coding sequence

<400> SEQUENCE: 19
atggagcgca acaatcagga ccagtgcatc ccgtacaact gcctcaacaa tcccgaggtt 60
ggcattctgg atatcgagaa cttcaatctg gagctggtgt cccaggtgtc agtcggcctc 120
accaggttcc tcctggaggc ctccatccca ggcgccgggt tcgctctggg cctcttcgac 180
atcatttggg gcgccctcgg cgtggatcag tggtccctgt tcctcgctca gattgagcag 240
ctgatcaatg agcgcattac caccgtggag aggaaccgcg ctatccaggc cctgtcgggc 300
ctctccagct cgtacgaggt ctacattgag gctctcaggg agtgggagaa cgacctggat 360
aatccggctt ctagggacag ggtggtggct aggttccggg ctaccgacaa ctcactcatt 420
acggatatcc cgctcctgga gatccccggc ttcgagattg ccacactgtc cgtgtacacg 480
caggcggcca acctgcacct cgccctcctg agggacgctg tctacttcgg ggagcgctgg 540
ggcctgacac agactaacat cgaggacctc cacacacggc tgactcgcta cattcaggag 600
tactccgatc attgcgcgcg ctggtacaac cagggcctca acaatattgg cgggatcaat 660
acccgctacc tcgacttcca gcgggagctg acgatcagcg tcctcgacat tgttgccctg 720
ttcccgaact acgatatccg gacctaccca attcctacgc agagccagct cacacgcgag 780
atctacactt cgccggttgt ggcccccggc gtgaattgga ttctgtcgat ctctaacgtc 840
ctcagggcgc cacacctgat ggacttcttc gatcggatca ttatctacac gggcacggtg 900
cgctcaaccc ctcactggga ggggcatgag gtcatctcca ggaggacggg ccaggggaac 960
gagattagga gcccgctcta cggcgtggct gctaatgccg agccgccagt tacgatcagg 1020
ccaacgggct tcacggacga gcagcggcag gtctaccgcg ttctgtccag ggtcgccagc 1080
ttccggaact cgggcacaaa tttctcactc gttgacgcgg cttccttcct gactatcttc 1140
agcgcgtctt caatctaccg caacggcttc gggttcaatg ctgacaccat cgatgagatt 1200
ccaatcgagg ggacggaccc ttacattggc tactcccacc gcctctgcca tgtgggcttc 1260
accgcctcca gcccgttcat cagccagtac gcgagggctc ccgtcttctc ctggacacac 1320
cggagcgcta cattcactaa caccatcgac ccagagcgca ttacgcagat ccctatggtg 1380
aaggcctaca acctgcatgc gggcgccaca gtcgttaggg gcccggggtt cactggcggg 1440
gacctcctgc ggcgcacgaa cacaggcact ttcgcggata tcagggtcaa tattaccggc 1500
cccctctccc agcgctaccg cgtgcgcatc cgctacgctt ctacaactga cctgcagttc 1560
ttcaccagga tcaacgggac gagcgtgaac cagggcaatt tccagcggac gatgaaccgc 1620
ggggacaatc tcgagtctgg caacttccgg acagccgggt tctcaactcc attctcattc 1680
tccaatgctc agtccacctt cacgctgggc acccaggcct tcagcaacca ggaggtctac 1740
attgacagga tcgagttcgt gcctgctgag gtcacgttcg aggccgagtc cgatctcgag 1800
cgggctcaga aggccgtgaa cgcgctgttc acaagcactt cgcagctggg cctcaagaca 1860
aacgtcactg gctaccacat cgaccaggtt tcgaatctcg tggcgtgcct gtctgacgag 1920
ttctgcctcg atgagaagcg cgagctgtcg gagaaggtga agcacgccaa gcggctctct 1980
gacaagcgca acctcctgca ggacccgaac ttcaggggca tcaataggca gcctgaccac 2040

-continued

```
ggctggaggg gctcgaccga tattacgatc cagggcgggg acgatgtttt caaggagaac   2100
tacgtgaccc tcccaggcac gttcgacgag tgctacccta catacctgta ccagaagatc   2160
gatgagtcca agctcaaggc gtacactcgc taccagctga ggggctacat cgaggactca   2220
caggatctcg agatctacct catccgctac aattccaagc acgagatcgt taacgtgccc   2280
ggcaccgggt cgctgtggcc actctctgtg gagaatcaga tcgggccatg cggcgagcct   2340
aaccggtgcg ccccgcacct cgagtggaat ccagacctgc attgctcctg ccgggatggc   2400
gagaagtgcg tccaccattc tcaccatttc tcactcgaca tcgatgttgg ctgcaccgac   2460
ctcaacgagg atctgggggt gtggctcatt ttcaagatca agacccagga cgggcacgcc   2520
aggctgggca acctcgagtt cctcgaggag gagcccctcc tgggcgaggc tctggctagg   2580
gtgaagaggg ccgagaagaa gtggcgcgac aagagggaga agctgcagct cgagaccaac   2640
atcgtctaca aggaggcgaa ggagtcagtg gatgctctct tcgtcaactc ccagtacgac   2700
cgcctgcagg ccgatacgaa tattgcgatg atccacgccg cggacaagag ggtgcatcgc   2760
atccgcgagg cctacctccc agagctgtcg gtcatccctg gcgttaacgc tgccattttc   2820
gaggagctgg agggccgcat cttcaccgcc tactctctgt acgacgcgag gaacgtgatt   2880
aagaacggga atttcaacaa tggcctcctg tgctggaacg tcaagggcca cgtcgatgtt   2940
gaggagcaga acaatcatcg cagcgtgctc gtcatccccg agtgggaggc cgaggtctcg   3000
cagaaggtta gggtgtgccc gggcaggggg tacatcctgc gcgtgaccgc ttacaaggag   3060
ggctacgggg agggctgcgt caccattcac gagatcgagg acaatacgga tgagctgaag   3120
ttctccaact gcgttgagga gggctacccg aacaataccg tgacgtgcaa cgagtacacc   3180
atgaaccagg gggtgggcga gtgcactgac gcttgcaacg ttcgcaatag gggctacgag   3240
gatgcgtacg ggcacaaccc aagcacccct gtgcattaca ccacgccata cgaggaggag   3300
acatacactg acgagaggcg ggagaaccct tgcgaggcca ataagggcta cgtgaactac   3360
acaccgctcc ccgtgggcta cgtgactaag gagctggagt acttccccga gaccgacacg   3420
gtctggattg agatcgggga gacagagggc actttcatcg ttgatagcgt ggagctgctg   3480
ctcatggagg agtaa                                                    3495
```

<210> SEQ ID NO 20
<211> LENGTH: 3501
<212> TYPE: DNA
<213> ORGANISM: Artificial Sequence
<220> FEATURE:
<223> OTHER INFORMATION: Synthetic Cry coding sequence

<400> SEQUENCE: 20

```
atgaagatca acaatcagaa ccagtgcatt ccgtacaact gcctgagcaa tccggaggag     60
gtgctcctgg acggcgagcg cattctgccg gacatcgatc ccctcgaggt cagcatgtcg    120
ctcctgcagt tcctcctgaa caatttcgtg ccgggcgggg gcgtcatctc gggcctgatc    180
aacaagattt ggggcgccct ccggccgtcc gagtgggagc tgttcctcgc ccagattgag    240
cagctgatcg acaggaggat tgaggcggcg gtcagggcta aggccatcgc tgagctggag    300
gggctgggcc ggtcttacca gctctacggc gaggcgttca aggagtggga gaagacaccc    360
gataacaccg cggcgcgctc cagggtgacc gagcgcttca ggatcattga cgcgcagatc    420
gaggctaaca ttccatcttt ccgcgtttca ggcttcgagg tgcctctcct gtctgtctac    480
acccaggcgg ctaacctgca tctcgccctc ctgcgggatt cagtggtgtt cggcgagagg    540
tgggggctga ccaccacaaa cgtgaatgac atctacaacc gccaggtcaa gaggattgac    600
```

-continued

```
gagtacagcg atcactgcgt cgacacctac aagacggagc tggagcgcct cgagttctcc    660
agcatcgcgc agtggaggat ctacaaccag ttccggaggg agctgaccct caccgtcctc    720
gatatcgttg ccctgttccc gaattacgac ggccgcctgt accccatcag gaccatttcc    780
cagctcacgc gggacatcta cacatctcca gtttcagagt tctactacgg ccctatctac    840
aactacaata ttgtggggag gctcactgag cagcagctga ggcggccaca tctcatggat    900
ttcttcaact ccatgatcat gtacaccagc gacaatcgca gggagcacta ctggtccggc    960
ctggagatga aggccacaga cactagcggg aaccaggtgt cgttccccct ggctggcacg   1020
agggggaatt ccgccccgcc agtcacagtt aggaacaatg gggagggcgt ctaccgcatc   1080
ctctctgagc cattctactc gtctcctttc ctgggcacct ccgtgctggg ctcccgcggc   1140
gaggagttcg ccttcgcgag caacactacc acgtccctgc cgagcactat ctacaggaat   1200
cgcggcaccg tggattcgct cgtctctatt ccacctcagg actactcggt cccgccccac   1260
aggggctact cccacctcct gtctcatgtt acgatgcaca actcatcccc gatcttccac   1320
tggacacatc gctccgccac cccacgcaat acgattgacc ctgatagcat cacgcagatt   1380
cccgttgtga aggcctcaca tctgtccggg ggcagcgtta tcaaggggcc gggccacaca   1440
gggggcgacc tgatttccct ccccgtcaac aatttcactc acttccgcat cccgttccag   1500
gccaacaccc cgcagcgcta ccgcatccgc atccgctacg ctgccgactc ggatggcacc   1560
ctggattcgg gggtgttcct ctcagctgcg gccggggacg gcttcaacac aacttcgtac   1620
agggctacca tgtctccggg cggctccctc acatctaggg atttccagtt cctggacctc   1680
aacacatcat tcacttccga cgtcgcgtcc aatctgtggc tccatttcat caggtacatt   1740
cggccaggca acctgtacat cgatagggcc gagttcattc ctgtggacgc caccttcgag   1800
gcgggctaca atctcgagcg ggcgcagaag gctgtgaacg ccctgttcac ctccacgaat   1860
cagaagggcc tccagaccga cgtcacggat taccacatcg atcaggtttc aaacctcgtg   1920
gattgcctgt ccgacgagtt ctgcctggac gagaagcgcg agctgagcga gaaggtcaag   1980
caggcgaaga ggctgtctga tgagcggaac ctcctgcagg actcaaactt ccggggcatc   2040
aatagggagc aggatagggg ctggaggggg tcgacacata tcactattca gggcggcaac   2100
gacgtcttca aggagaattt cgttactctg ccgggcgcgt tcgatgcttg ctaccccacc   2160
tacctctacc agaagatcga cgagtccaag ctgaaggcct acacccgcta cgagctgcgg   2220
ggctacatcg aggacagcca ggacctcgat atctacctga ttcgctacaa cacaaagcac   2280
gagactctca atgtgccggg cactaagtcc ccctggtccc tgtgcacgga gtccccactc   2340
ggcaagtgcg gggagcctaa caggtgcgcc tcccagatcg agtggaatcc ggacctggat   2400
tgctcctgca gggacggcga gaagtgcgct caccattcac accatttctc cctcgacatc   2460
gatgtgggct gcacggacct caacgagaat ctggggatct gggtcatttt caagatcaag   2520
acgcaggacg gccacgccag gctggggaac ctcgagttcc tcgaggagaa gccgctcctg   2580
ggcgaggctc tggctagggt caagcgcgcc gagaagaagt ggagggacaa gcgggagaag   2640
ctccagagcg agacgaacat cgtgtacaag gaggccaagg aggcggttga tggcctgttc   2700
gtggactcgc agtacgagcg cctccaggcg gataccaaca ttgctatgat ccacgctgcc   2760
gacaagcacg tgcatcagat cagggaggtc tacttcccag agctgtccgt catccctggc   2820
gttaacgcgg ctattttcga ggagctggag ggccggatct tcacggccta ctcactctac   2880
gatgcgcgca acgtcattaa gaatggcgac ttcaacaatg ggctgtcctg ctggaacgtt   2940
```

aagggccatg tggacgtcga ggttcagaac aatcaccgct cagtgctcgt catcgctgag 3000
tgggaggcgg aggtgtccca ggaggttccg gtgtgcccgg ggaggggcta catcctgagg 3060
gttaccgcct acaaggaggg gtacggcgag ggtgcgtga cgattcatga gatcgaggac 3120
cacacagatg agctgaagtt caggaactgc gaggaggagg aggtttaccc gaacaataca 3180
gtgacttgca atggctacac cgcgacgcag gaggagtaca aggatgctta cacctcgagg 3240
aacaggggct acgacgaggc ctacgggaac aatccaagcg tccctgctga ttacgcctcg 3300
gtttacgagg agaaggctta cacggacggc aggagggaga acccatgcga gatggagagg 3360
ggctacactc cactgcctgt ggggtacatc accaaggagc tggagtactt ccctgagaca 3420
gatactgtct ggatcgagat tggcgagacc gaggggacgt tcatcattga cagcgtggag 3480
ctgctgctca tggaggagta a 3501

<210> SEQ ID NO 21
<211> LENGTH: 3546
<212> TYPE: DNA
<213> ORGANISM: Artificial Sequence
<220> FEATURE:
<223> OTHER INFORMATION: Synthetic mutant BT-0001 coding sequence

<400> SEQUENCE: 21
atggacaata atccgaacat caacgagtgc atcccttaca actgcctgtc taaccctgag 60
gtggaggtgc tgggggcga gcgcatcgag acaggctaca ctccaatcga catttcgctg 120
tctctcacgc agttcctcct gtcggagttc gtgcctggcg ctgggttcgt gctgggcctc 180
gtcgatatca tttgggggat cttcggcccc tcccagtggg acgctttcct ggtccagatc 240
gagcagctca ttaaccagcg catcgaggag ttcgctagga atcaggccat ttcgcggctg 300
gagggcctct ctaacctgta ccagatctac gcggagtcct tccgcgagtg ggaggctgat 360
ccgaccaacc ccgccctgag ggaggagatg cggattcagt tcaacgacat gaattcggcg 420
ctgaccacgg ctatcccgct cttcgccgtc cagaactacc aggttcccct cctgtctgtg 480
tacgtccagg ccgcgaatct gcacctctca gtgctgcgcg acgtttccgt gttcgggcag 540
cgctggggct tcgacgctgc tactattaac tcccgctaca atgatctcac taggctgatc 600
ggcaactaca ccgactacgc cgtgcgctgg tacaataccg ggctcgagag ggtttggggc 660
ccggacagca gggattgggt caggtacaac cagttccgca gggagctgac cctcacggtt 720
ctggacatcg tggccctctt ctcgaactac gattctcggc gctacccaat taggaccgtg 780
agccagctga cgcgggagat ctacacaaat cctgtcctcg agaacttcga cgggtcgttc 840
aggggcatgg ctcagcgcat tgagcagaat atccgccagc cgcacctgat ggatatcctc 900
aattcgatca ccatttacac ggacgtgcac agggggttca actactggtc tggccatcag 960
atcaccgctt ctccagtcgg gttctcaggc ccggagttcg ctttcccact gttcgggaac 1020
gctggcaatg ctgctccacc cgtcctagtt tcgctgacgg gcctcgggat cttccgcaca 1080
ctgtccagcc cactctacag gcggatcatt ctcggctctg ggcctaacaa tcaggagctg 1140
ttcgtgctcg acggcacgga gttctctttc gcgtcactga caactaacct cccatccact 1200
atttacaggc agaggggcac cgtggacagc ctcgatgtaa tcccacctca ggacaactcg 1260
gtcccgccaa gggctggctt ctcacaccgc ctgtcccatg taaccatgct cagccaggct 1320
gctggcgctg tttacactct gagggctccc accttctcct ggcagcaccg gagcgccgag 1380
ttcaacaata tcattgcgtc agattccatc acgcagattc cggcggtgaa ggggaacttc 1440
ctcttcaatg gctccgtaat tagcggcccc gggttcacag gcggggacct ggtgcgcctc 1500

```
aactcgtctg ggaacaatat ccagaatagg ggatacatcg aggtcccaat ccacttccct   1560

agcacatcga ctcgctaccg cgtgagggtc cgctacgcta gcgtgactcc gattcatctg   1620

aacgtcaatt ggggcaattc atccatcttc tcgaacaccg tgcccgctac cgctacgtct   1680

ctggacaacc tccagtcctc cgatttcggc tacttcgagt ctgctaatgc cttcacgtct   1740

tcactaggga atatcgttgg cgtgcggaac ttctcaggga cagccggcgt tatcattgac   1800

cgcttcgagt tcatcccggt gacagccact ctggaggcgg agtacaacct cgagcgcgct   1860

cagaaggccg tgaacgcgct gttcacctcc acgaaccagc tgggcctcaa gacaaatgta   1920

actgactacc acatcgatca agtcagcaac ctggttacct gcctctcgga cgagttctgc   1980

ctggatgaga agagggagct gagcgagaag gtgaagcacg ccaagaggct ctcagacgag   2040

cggaacctcc tgcaggactc caatttcaag gatatcaaca ggcagccaga gagggggtgg   2100

ggcgggtcaa ccggcatcac gattcagggc ggggacgatg tcttcaagga gaactacgta   2160

acactgagcg gcactttcga cgagtgctac cccacttacc tctaccagaa gatcgacgag   2220

tcaaagctga aggcgttcac ccgctaccag ctccggggat acatcgagga ctcccaggat   2280

ctggaggtgt acctcatccg ctacaacgcc aagcacgaga cgctgaacgt cccaggcaca   2340

gggtctctgt ggccactcgc ggttaagtca ccaattgggc gctgcggcga gccaaacagg   2400

tgcgctccta ggatcgagtg gaagcctgac gtggattgct cctgcaggga cggcgagaag   2460

tgcgctcacc atagccacca tttctcgctc gacatcgatg tcgggtgcac ggacctgaac   2520

gaggatctcg gcgtctgggt tatcttcaag attaagacac aggacgggca tgcgaagata   2580

ggcaacctgg agttcctcga ggagaagctc ctgctcggcg aggctctggc tagggtgaag   2640

aaggccgaga agaagtggcg cgacaagagg gagaagctcg agtgggagac caacatcgtc   2700

tacaaggagg ccaaggagtc cgttgacgcg ctgttcgtgg atagccaata caacaggctc   2760

cagacagata ctaatatcgc catgattcac gctgccgaca agcgggtgca tcgcatccgc   2820

gaggcgtacc tgccagagct gagcgtgatt cctggcgtca acgcggctat cttcgaggag   2880

ctggagggcc tcattttcac ggctttctcc ctgtacgacg cccgcaacgt gatcaagaat   2940

ggggatttca actacggcct aagctgctgg aacgtcaagg gccacgtgga cgtcgaggag   3000

cagaacaatc ataggtccgt tctggtgatc ccggagtggg aggctgaagt cagccaggaa   3060

gtcagggttt gcccaggcag gggatacatc ctccgggtta ccgcctacaa ggagggctac   3120

ggggagggct gcgtgacgat ccacgagatt gaggacaaca cagatgagct gaagttcagc   3180

aattgcgttg aggaggaggt gtacccgaac aataccgtga cgtgcaacga ctacacagcc   3240

actcaggagg agtacgaggg cacctacacg tcgaggaacc gggggtacga cggcgcttac   3300

gagtctaatt ccagcgtccc agccgactac gcctcagcgt acgaggagaa ggcgtacacg   3360

gacggccgca gggataatcc ttgcgagtcc aaccggggct accgcgatta cactccactg   3420

cctgccggct acgtcaccaa ggagctggag tatttcccgg agacagacaa ggtttggatc   3480

gagcttggcg agacggaggg gaccttcctt gtggattcgg ttgagctgct gctgatggag   3540

gagtag                                                              3546
```

<210> SEQ ID NO 22
<211> LENGTH: 3531
<212> TYPE: DNA
<213> ORGANISM: Artificial Sequence
<220> FEATURE:
<223> OTHER INFORMATION: Synthetic mutant BT-0003 coding sequence

<400> SEQUENCE: 22

```
atggagatcg tgaacaatca gaatcagtgc gtgccttaca actgcctcaa taatcccgag     60
atcgagatcc tggagggggg gcgcatttcg gtgggcaaca cgcctatcga catttccctc    120
agcctgacac agttcctcct gtctgagttc gttccaggcg ctgggttcgt gctcggcctg    180
atcgacctca tttgggggtt cgtgggcccg tcccagtggg atgctttcct cgcccaggta    240
gagcagctga tcaaccagag gattgcggag gctgttcgga ataccgcgat ccaggagctg    300
gagggcatgg ctcgcgtgta caggacatac gccactgcgt tcgctgagtg ggagaaggct    360
ccagacgatc cagagctgag ggaggctctg aggacacagt tcacggcgac agagacttac    420
atctccggcc gcattagcgt cctcaagatc cagaccttcg aggttcagct cctgagcgtg    480
ttcgctcagg ctgctaacct ccacctgtcg ctcctgaggg acgtggtctt cttcgggcag    540
cgctggggct tctcgaccac gacagtgaac aattactaca acgacctcac tgagggcatc    600
tctacctaca cggattacgc cgtccgctgg tacaataccg ggctggagag ggtgtggggc    660
cccgacagca gggattgggt ccggtacaac cagttccgca gggagctgac actgactgtg    720
ctcgacatcg tcgcgctgtt ctcgaactac gattctcggc gctaccccat ccggacagtg    780
tcgcagctca ctcgcgagat ttacaccaac ccagtcctgg agaatttcga cgggtccttc    840
aggggcatgg ctcagcggat cgagcagaac attaggcagc cccacctcat ggacatcctg    900
aattccatca ccatttacac ggacgtgcac cgcgggttca actactggag cggccatcag    960
atcaccgctt ctccagtcgg gttctcaggc ccggagttcg ctttccccct cttcgggaac   1020
gctggcaatg ctgctccacc cgtgctagtc tccctgactg gcctcgggat cttcaggacc   1080
ctctccagcc cactgtacag gcggatcatt ctgggcagcg ggcctaacaa tcaggagctg   1140
ttcgtgctcg acggcacgga gttctcattc gcgtccctca ctaccaacct gccctccacg   1200
atctacaggc agcggggcac agtcgactct ctcgatgtaa ttccacctca ggacaactca   1260
gtcccgccaa gggctggctt ctcacacagg ctctcccatg ttaccatgct gagccaggct   1320
gctggcgctg tgtacacgct gcgggctccg acattctcct ggcagcaccg cagcgcggag   1380
ttcaacaata tcattccgtc gtctcagatc acgcagattc ccctcacaaa gtccactaac   1440
ctgggcagcg ggacatcggt tgtgaagggc ccggggttca ctggcgggga catcctcagg   1500
aggacctcgc caggccagat ctctactctc cgcgttaata ttaccgctcc actgagccag   1560
cgctacaggg tccgcatccg ctacgcctca acgacaaacc tgcagttcca cacgtccatc   1620
gacgggaggc ctattaacca gggcaatttc tctgccacta tgtcatccgg gtcaaacctc   1680
cagtcgggct ctttccgcac cgtggggttc actaccccgt tcaacttctc caacggcagc   1740
tcggtgttca ccctgtcagc gcacgtcttc aactccggca atgaggttta catagaccgg   1800
attgagttcg ttccggccga agtgactttc gaggcggagt acgatctcga gcgcgcgcag   1860
aaggctgtga acgagctgtt cacgtcttca aatcagatcg gcctgaagac cgacgtcacg   1920
gattaccaca ttgaccaggt ctccaacctc gttgagtgcc tgagcgacga gttctgcctc   1980
gacgagaagc aggagctgtc cgagaaggtg aagcatgcca agcgcctgag cgacgagagg   2040
aacctcctgc aggacccgaa cttccgcgga atcaacaggc agctggacag ggggtggagg   2100
ggcagcacag atatcactat tcagggcggg gacgacgtct tcaaggagaa ctacgttacc   2160
ctcctgggca cgttcgacga gtgctaccca acgtacctgt accagaagat cgacgagtca   2220
aagctcaagg cgtacacacg ctaccagctg cgcggataca tcgaggacag ccaggatctc   2280
gagatctacc tgattaggta caacgccaag cacgagacgg ttaacgtgcc tggcacaggc   2340
```

tccctctggc cactctctgc tcagtcaccc atcgggaagt gcggcgagcc aaacaggtgc 2400
gctcctcatc tcgagtggaa tccggacctg gattgcagct gcagggacgg cgagaagtgc 2460
gctcaccata gccaccattt ctcgctcgac atcgatgtag gctgcacgga cctcaatgag 2520
gatctagggg tctgggttat cttcaagatt aagacacagg acgggcacgc taggctgggc 2580
aacctcgagt tcctggagga gaagccactc gtgggcgagg ctctggctag ggtcaagatc 2640
gccgagaaga agtggaggga caagcgggag aagctggagt gggagacgaa catcgtgtac 2700
aaggaggcta aggagtcggt ggatgccctc ttcgtaaact ctcagtacga ccagctgcag 2760
gctgatacca atatcgccat gattcacgcc gcggacaagc gggtccattc gatccgcgag 2820
gcctacctcc cagagctgtc tgtgatccct ggcgtcaacg ctgccatttt cgaggagctg 2880
gagggcagga tcttcaccgc gttcagcctg tacgacgctc ggaacgtgat taagaacggg 2940
gatttcaaca atggcctctc gtgctggaac gtaaagggcc acgtggacgt cgaggagcag 3000
aacaatcagc gctctgtcct ggtcgttcct gagtgggagg ccgaggtttc acaggaagtt 3060
agggtgtgcc caggcagggg atacatcctc cgcgtgaccg cgtacaagga gggctacggg 3120
gagggctgcg tcacgatcca tgagatagag aacaatacag acgagctgaa gttcagcaac 3180
tgcgtggagg aggagatcta ctcgaacaat accgttacgt gcaacgatta cactgtgaat 3240
caggaggagt acggcggggc ttacacctca aggaacaggg gctacaacga ggctccatcc 3300
gtccctgctg actacgctag cgtttacgag gagaagtcgt acacggacgg caggagggag 3360
aacccatgtg agttcaatcg cggctacagg gactacactc cactccctgt cggctacgtt 3420
accaaggagc tggagtattt cccagagacc gataaggtct ggctcgagat tggcgagact 3480
gaggggacat tcattgtgga tagcctggag ctgctgctga tggaggagtg a 3531

<210> SEQ ID NO 23
<211> LENGTH: 3714
<212> TYPE: DNA
<213> ORGANISM: Artificial Sequence
<220> FEATURE:
<223> OTHER INFORMATION: Synthetic mutant BT-0020 coding sequence

<400> SEQUENCE: 23
atgaatagca acaggaagaa tgagaacgag atcattgacg cttcgttcat cccagccgtc 60
tcgaacgagt ctgttactat ttctaaggag tacgcgcaga ccaatcagct ccagaacaat 120
tcaattgagg acgggctgtg catcgctgag ggcgagtaca ttgatccttt cgtgtcagcg 180
tccaccgtcc agacggggat ctccattgct ggccgcatcc tgggggtcct gggcgttcca 240
ttcgctggcc agctcgcctc attctactcc ttcatcgtgg gggagctgtg gcctaagggc 300
agggaccagt gggagatctt catggagcac gttgagcagc tcgtgcgcca gcagattact 360
gctaatgcca ggaacacggc cctggctcgg ctccagggcc tggggaactc cttccgcgcc 420
taccagcaga gcctcgagga ctggctggag aataggaacg atgcccggac gcgcagcgtg 480
ctctacacac agtacatcgc gctggagctg gacttcctca acgcgatgcc actgttcgct 540
attcgcgagc aggaggttcc tctcctgatg gtgtacgctc aggcggccaa cctgcacctc 600
ctgctcctgc gcgatgcctc gctctacggg agggagttcg gcctgacttc tcaggagatc 660
cagcgctact acgagaggca ggtcgagagg acccgggact actcagatca ttgcgtgcag 720
tggtacaaca cggggctcaa caatctgagg ggaaccaacg cggagagctg ggtccgctac 780
aatcagttcc gcagggacct gaccctgggc gtcctggatc tcgttgccct cttcccgtca 840

-continued

```
tacgacacca ggacgtaccc aatcaacaca tccgcgcagc tgactcggga ggtctacacc    900
gatgccattg gggcgactgg cgttaacatg gcttcgatga attggtacaa caataacgcc    960
ccaagcttct cggcgatcga gaccgctgtg attaggtctc ctcacctcct ggacttcctc   1020
gagcagctga agatcttctc ggcctccagc aggtggtcta acacccggca catgacgtac   1080
tggaggggcc atacgatcca gagcaggccc attcgcggcg ccctcatcac aagcactcac   1140
ggcaatacca acacgtcgat caacccagtc acgttccagt tcccttctcg ggacgtttac   1200
cgcacagagt catacgccgg ggtgctcctg tggggcatct acctcgagcc aatccacggc   1260
gtgccgacgg tcaggttcaa tttccggaac ccccagaata cgttcgagcg cggcacagcg   1320
aactactctc agccgtacga gtcacccggc ctgcagctca aggactccga gacggagctg   1380
ccgccggaga ccaccgagag gccaaactac gagtcttact cacaccggct gtcccatatc   1440
ggcatcattc tccagactag gctgaatgtg cctgtctact cctggaccca ccgcagcgct   1500
gacaggacaa acactatcgg cccaaatcgg atcacgcaga ttcctgccgt gaaggggaac   1560
ctcctgttca atggcagcgt catctcgggc ccggggttca caggcgggga cctcgtccgc   1620
ctgaataaca gcgggaataa catccagaac aggggctacc tcgaggtgcc cattcagttc   1680
acctccacga gcacacgcta cagggttcgg gtgcgctacg cttccgtgac cccccatccac   1740
ctgtcagtca actggggcaa ttccaacatt ttctcgtcta cagtgcccgc gactgctgcc   1800
agcctcgaca atctgcagtc gcgggatttc ggctacttcg agtctaccaa cgccttcaca   1860
tcagttactg ggaatgtggt cggcgtgcgc aacttctccg agaatgcgcg cgttatcatt   1920
gacaggttcg agttcatccc agtgactgcc accttcgagg cggagtacga tctggagagg   1980
gctcaggagg ccgtcaacgc gctcttcacg aatacaaacc cgaggaggct gaagacgggc   2040
gtgaccgact accacatcga tgaggtgtcg aacctcgtcg cctgcctgtc tgacgagttc   2100
tgcctcgatg agaagcgcga gctgctggag aaggtgaagt acgcgaagcg gctgagcgac   2160
gagcgcaacc tcctgcagga cccgaacttc acgtccatca ataagcagcc cgacttcatt   2220
agcacgaacg agcagtcgaa tttcacatct atccacgagc agtcagagca tgggtggtgg   2280
ggctccgaga acatcaccat tcaggagggc aacgatgttt tcaaggagaa ttacgtgacc   2340
ctcccaggca cgtacaacga gtgctaccct acgtacctgt accagaagat cggcgagtcg   2400
gagctgaagg cctacacacg ctaccagctg cgcggataca tcgaggactc tcaggatctc   2460
gagatctacc tgattaggta caacgcgaag cacgagactc tggacgtgcc cggcaccgag   2520
tcggtctggc cgctgtctgt tgagtccccg atccgcaggt gcggcgagcc caacaggtgc   2580
gctccccatt tcgagtggaa tccggacctc gattgctcct gcagggacgg cgagaagtgc   2640
gcccaccatt cacaccattt ctccctggac attgatgtcg ggtgcatcga tctccacgag   2700
aacctgggcg tgtgggttgt gttcaagatc aagacgcagg aggggcatgc taggctgggc   2760
aacctggagt tcattgagga gaagcccctc ctgggcgagg ctctctccag ggtcaagcgc   2820
gcggagaaga agtggaggga caagcgggag aagctgcagc tcgagactaa gcgcgtgtac   2880
accgaggcta aggaggccgt ggatgcgctc ttcgtcgaca gccagtacga taggctgcag   2940
gccgacacga acatcggcat gattcacgcg gctgataagc tggtgcatcg catccgcgag   3000
gcgtacctct ccgagctgag cgttatcccg ggcgtgaacg ctgagatttt cgaggagctg   3060
gaggggcgga tcattaccgc gatctccctg tacgacgctc gcaacgtcgt taagaatggg   3120
gatttcaata acggcctcgc ctgctggaac gtcaagggcc acgtcgacgt tcagcagagc   3180
caccatcgct cggtgctggt catccccgag tgggaggctg aggtgagcca ggcggttagg   3240
```

gtgtgcccgg gcaggggata catcctccgc gtcaccgcgt acaaggaggg ctacggggag 3300
ggctgcgtga ctatccacga gattgagaat aacaccgacg agctgaagtt caagaactgc 3360
gaggaggagg aggtctaccc aactgacacc gggacgtgca atgattacac ggcccatcag 3420
ggcacagccg cgtgcaactc caggaatgct gggtacgagg acgcctacga ggtcgataca 3480
actgcgagcg ttaactacaa gcccacctac gaggaggaga catacactga cgtgcgcagg 3540
gataaccact gcgagtacga ccgcggctac gtcaattacc cacctctccc ggccggctac 3600
gtgacgaagg agctggagta cttccccgag acagacaagg tctggatcga gcttggggag 3660
acagagggca ctttcctcgt ggatagcatt gagctgctgc tcatggagga gtaa 3714

<210> SEQ ID NO 24
<211> LENGTH: 2148
<212> TYPE: DNA
<213> ORGANISM: Artificial Sequence
<220> FEATURE:
<223> OTHER INFORMATION: Synthetic mutant BT-0022 coding sequence

<400> SEQUENCE: 24
atgaagtcta agaatcagaa catgcatcag agcctcagca acaacgctac tgtggataag 60
aatttcacgg gcagcctgga gaataacaca aatactgagc tgcagaattt caaccacgag 120
ggcatcgagc cattcgtctc agtttccaca attcagactg gcatcgggat tgcgggcaag 180
atcctgggca acctcggcgt gccgttcgct ggccaggttg cttccctcta cagcttcatc 240
ctgggcgagc tgtggcccaa ggggaagagc cagtgggaga ttttcatgga gcatgtcgag 300
gagctgatca atcagaagat ttcgacctac gcccggaaca aggctctggc tgacctcaag 360
ggcctggggg atgctctcgc tgtgtaccac gagtcgctgg agtcttggat caagaaccgc 420
aacaatacca ggacgcggtc tgtggtcaag tcacaataca ttaccctcga gctgatgttc 480
gtccagtcac tgccgtcctt cgccgtttcc ggcgaggagg tgccgctcct gccaatctac 540
gctcaggctg cgaatctcca tctcctgctc ctgcgcgacg cctcgatctt cggcaaggag 600
tgggggctga gcgattcgga gatttctact ttctacaacc ggcaggtcga gcgcaccagc 660
gactactcgg atcactgcac aaagtggttc gacactggcc tcaataggct gaaggggtcc 720
aacgcggaga tctgggtgaa atacaaccag ttccgcaggg acatgactct catggtcctc 780
gatctggttg ccctgttcca gagctacgat acacacatgt acccaatcaa gaccacggct 840
cagctcacca gggaggttta cacgaacgcc attggcacag tgcacccaca tccttctttc 900
acctcaacaa cttggtacaa caataacgct ccgtctttct cagccatcga ggctgccgtc 960
attcggagcc cccatctcct ggacttcctg gagcaggtta ctatctactc cctcctgagc 1020
aggtggtcga atacccaata catgaacatg tggggcgggc acaagctcga gttccggaca 1080
attggcggga ctctgaacac atccactcag ggcagcacca atacgtcgat caacccagtc 1140
accctccctt tcacgtcaag ggacatctac cggacggagt ccctggccgg cctcaatctg 1200
ttcctcacac agccagttaa cggggtgccc agggtcgact tccactggaa gttcgtgacg 1260
catccaatcg cgtccgataa cttctactac cctggctacg ctggcattgg cacccagctc 1320
caggacagcg agaatgagct gccaccagag accacgggcc agccaaacta cgagtcctac 1380
agccacaggc tctcccatat cggcctgatt tcggcgtctc acgtgaaggc tctcgtctac 1440
tcttggaccc atcgctcagc ggacaggaca aacactatcc actcagattc catcacgcag 1500
attcctctcg tcaaggccca cacactgcag agcggcacaa ctgttgtgaa gggcccaggg 1560

```
ttcacgggcg gggacatcct gaggcgcaca tccggcgggc ctttcgcgtt cagcaatgtt   1620
aacctcgatt ggaatctgag ccagcgctac cgcgcccgca tccgctacgc gtcgaccacg   1680
aacctccgga tgtatgtgac gatcgcgggc gagcgcattt tcgctgggca gttcaataag   1740
accatgaaca cgggcgaccc actgaccttc cagagcttct cgtacgctac aatcgatact   1800
gccttcacct tccctacgaa ggcctccagc ctcactgtgg gcgctgacac cttctcgtct   1860
gggaacgagg tctacgtgga tcgcttcgag ctgatcccag tgaccgctac gctcgaggct   1920
gtcacggacc tggagagggc tcagaaggcc gtgcatgagc tgttcacctc cactaatcca   1980
ggcgggctga agaccgacgt cgctaaggat cactacacca acacgctctc taagtcagtt   2040
cagtcggtgt tcaggtgccg gtgctctgag cgcacgaggc tctaccgctg gggctacccg   2100
tctaagaagg agtactggta catttggggc tacacctcaa agtactga               2148
```

<210> SEQ ID NO 25
<211> LENGTH: 3285
<212> TYPE: DNA
<213> ORGANISM: Artificial Sequence
<220> FEATURE:
<223> OTHER INFORMATION: Synthetic mutant BT-0027 coding sequence

<400> SEQUENCE: 25

```
atgttcctcg agcagattga gcagctgatc gaccagcgca ttgagaccgt cgagaggaat     60
cgggcgatcc agacgctcat tggcctgtcg aactcttacg atgtgtacat cgaggcgctc    120
aaggagtggg agaacaatcc ggacaattca gcttcccagg agcgcgtcag gaaccggttc    180
cgcaccacgg acgatgcgct catcacaggc attccgctcc tggctattcc caatttcgag    240
atcgccactc tgtcagtcta cgttcaggcg gccaacctcc acctgtccct cctgagggac    300
gctgttttct tcggcgagcg ctgggggctg acccagatca atgtggacga tctctaccgc    360
aggctgacga acaatatccg gaactactcc gatcattgcg cgcgctggta caatgagggc    420
ctcgacaaca ttagcgggct gagccggtcg atcaatttcc agcgcgaggt cacaatttcg    480
gttctcgata tcgtggccct gttcccgaac tacgacattc gcacttaccc catcagcaca    540
acttcgcagc tcaccaggga gattttcacg tcgccgatcg tggtccccaa cgacttctcc    600
gttgcctacg agggcgtgcg gcgcgctccc cacctgttcg agttcctcga gaagctcgtg    660
atctacacgg gcgatcgcag cgggatcagg cactgggccg gccatgagat tacgtctagg    720
cggacagact cataccacgg catcatccgc tacccgctct acgggacagc tgccaacgcc    780
gagtccccat acactctcgc gctgcagcct tctgagtcaa tctaccgcac cctctccgag    840
cctattttca gccagacggg cgggctgtct ccgcacagga ggagggttgt ggagggcgtc    900
gagttctcaa tcgtcaacaa taacgttaac ccgtccagct tcgtgtaccg caggaagggc    960
tctctcgatt cattcacaga gctgccgccc gaggacgagt ctgtcccacc atacatcggc   1020
tactcacacc agctctgcca tgtgggcttc gggaggacga atgtcatctt cgagccgtcg   1080
aacttcgcca gggtgcccgt cttctcgtgg acacaccggt ctgcgacacc aactaatacc   1140
atcgaccctg atcggatcac tcagattcct tccgtgaagg cgtcgtctct gcgcaactcg   1200
acagtcgttt ctggcccggg gttcactggc ggggatatcg tccgcatggg cgctgttcac   1260
cagatctacg ccaccgacct cagcatgaac gtgaggccgt cagtcgctct gtcccgctac   1320
ctcatcaggc tgcggtacgc ctgcaggggc tcatccaata tcgttattca tgggccatcc   1380
atccggttcg tgtccctccc tagcaccatg tcgaacgacg agccgctgac gtaccagtca   1440
ttccgctacg cctccatcac cacgccaatt accaggccta tctacaatat gttcaacctc   1500
```

-continued tccatcagcc ggattagcgg cgtccagaat ctgttcatcg accgcattga gttcatcccc 1560
gtggatgcga acttcgaggc tgagagggac ctggagcgcg ctcagaaggc tgtcaatgcg 1620
ctcttcacgt ccacaaacca gaggggcctg aagattgacg tgacggatta ccacatcgat 1680
caggttagca acctcgtgga ctgcctgtcg gatgagttct gcctcgacga gaagcgcgag 1740
ctgtctgaga agtcaaagca tgccaagagg ctcagcgacg agcggaacct cctgcaggac 1800
ctgaatttca aggatatcaa ccgccagccg gagagggggt ggtccggctc tactgggatc 1860
accattcagg gcggggacga tgttttcaag gagaactacg tgactctccc cggcaccttc 1920
gatgagtgct acccaaccta cctgtaccag aagatcgacg agtccaagct caaggcttac 1980
acgcgctacc agctgagggg atacatcgag gacagccagg atctcgagat ctacctcatc 2040
aggtacaatg ccaagcacga gaccgttaac gtgccaggct caggctccct ctggcctctg 2100
tccgtcgagt cctccgttgg caagtgcggg gagccaaata ggtgcgccag ccgcatggag 2160
tggaacccag acctcgattg ctcctgcagg gacggcgaga agtgcgctca ccatagccac 2220
catttctcgc tggacatcga tgtcggctgc accgacctca acgaggatct gggggtctgg 2280
gttattttca agatcaagac gcaggacggc cacgccaaga tcgggaacct cgagttcctg 2340
aaggagaagc tgctgctggg cgaggctctg gccagggtga agaaggcgga gaagaagtgg 2400
agggacaagc gggataagct ggagtgggag accaacgtgg tctacaagga ggcgaaggag 2460
agcgtggacg ctctcttcgt cgattcccag tacagccgcc tgcaggccga tacgaacatt 2520
gcgatgatcc acgcggctga caagagggtg catcgcatca gggaggctta cctcccggag 2580
ctgaccgtga ttcccggcgt caacgcctcg atcttcgagg agctggaggg caggatcttc 2640
acggcctact ctctgtacgg cgccaggaat gtcatcaaga acggcgactt caataacggg 2700
ctctcctgct ggaacgtgaa gggccacgtg gaggtccagc agatccacca taggtctgtc 2760
ctggttgtgc cctcatggaa gacagaggtt tcccaggagg tttgcgtgtg cccaggcagg 2820
ggatacatcc tcagggtgac tgcctacaag gagggctacg ggagggcaa tgtcacaatt 2880 cacgagatcg agaataacac tgacgagctg aagttccgca attgcgagga ggaggaggtc 2940
tacccgaata acactgttac ctgcaatgac tacaccgtca accaggagga gtacaagggc 3000
acgtgcacat cccggaaccg cgggtacgac gagagctacg agtcttcatc cagcgagagc 3060
gcatactacg cctcggtgta cgaggagaag ggctacacgg atgggcggcg cgagaatctc 3120
tgcgagttca acagggggta cggcgactac accagcatcc ctacagccta cgtgactaag 3180
gagctggagt acttcccgga gacagataaa gtgtggatcg agcttggcga gactgagggg 3240
gccttcatcc tggactccgt ggagctgctc ctgatggagg agtaa 3285

<210> SEQ ID NO 26
<211> LENGTH: 3509
<212> TYPE: DNA
<213> ORGANISM: Artificial Sequence
<220> FEATURE:
<223> OTHER INFORMATION: Synthetic mutant BT-0029 coding sequnce

<400> SEQUENCE: 26
atggagatca acaatcagaa ccagtgcgtc ccgtacaatt gcctcaacaa tcccgagtcc 60
gagatcctga acgtggccat tttctccagc gagcaggtcg cggagattca cctcaagatc 120
acccgcctga ttctcgagaa cttcctgccg ggcgggtctt tcgctttcgg cctgttcgac 180
ctcatttggg ggatcttcaa tgaggatcag tggtcagcgt tcctcaggca ggtggaggag 240

-continued

```
ctgatcaacc agaggattac ggagttcgct aggggccagg ctatccagag gctggtgggc    300
ttcgggaggt cctacgacga gtacattctg gctctcaagg agtgggagaa cgacccggat    360
aatcccgcca gcaaggagag ggttcggaca cgcttcagga ccacggacga tgccctcctg    420
actggcgtgc cactcatggc tatccctggg ttcgagctgg ctaccctctc ggtctacgct    480
cagtcggcca acctgcacct cgccctcctg agggacgctg tgttcttcgg ggagaggtgg    540
ggcctcaccc agacgaacat caatgacctc tactcgcggc tgaagaactc tattcgcgat    600
tacaccaatc attgcgttag gttctacaac atcggcctgg ggaacctcaa tgtgattcgg    660
ccagagtact accggttcca gcgcgagctg acgatcagcg ttctggacct cgtggcgctg    720
ttccctaact acgatatccg gacttacccg attcccacca agtcccagct cacgcgcgag    780
atctacacag acccaatcat ttcgccgggg gcccaggccg gctacacact ccaggacgtc    840
ctgagggagc cgcacctgat ggatttcctg aaccggctca tcatctacac tggggagtac    900
cggggcatcc ggcactgggc tggccatgag gtggagtcgt ctcgcactgg catgatgacc    960
aacatccgct tccccctcta cggcacggcg gccacagccg agccaacacg cttcattact   1020
ccgtcgacct tccccggcct gaatctcttc taccggactc tgtcggcccc catcttccgc   1080
gacgagccgg gcgctaacat cattatccgc taccgcacct ccctggtgga gggcgttggg   1140
ttcatccagc cgaacaatgg cgagcagctg tacagggtgc ggggcaccct cgactccctg   1200
gatcagctgc ccctcgaggg cgagtcatcc ctcacggagt actcacacag gctgtgccat   1260
gtccggttcg ctcagtccct ccggaacgcg gagccactgg actacgcccg ggtgcctatg   1320
ttctcatgga cacaccgctc cgccacacca actaatacca tcgaccctga tgttattact   1380
cagatcccac tcgtgaaggc gttcaacctg cattcgggcg ctactatcgt caagggccct   1440
gggttcaccg gcggggacat tctgcgcagg acgaatgttg ggtctttcgg cgatatgcgc   1500
gtgaacatca cggcgcccct cagccagcgc tacagggtgc ggattcgcta cgcttcgaca   1560
actgacctgc agttctacac caacatcaat gggaccacga ttaacatcgg caatttcagc   1620
tcgacgatgg attccgggga cgatctccag tacggcaggt tccgggtggc ggggttcaca   1680
actccgttca cgttcagcga cgctatgtcg acgttcacaa tcggcgcctt cagcttctct   1740
tcaaacaatg aggtgtacat tgaccgcatc gagttcgtcc ccgctgaggt taccttcgag   1800
gccgagtacg atctggagaa ggctcagaag gccgtcaatg cgctcttcac gtccagcaac   1860
cagatcggcc tgaagacgga cgtgacagat taccacattg acaaggtgag caacctcgtc   1920
gagtgcctgt cggacgagtt ctgcctcgat gagaagaggg agctgtccga gaaggtcaag   1980
catgcgaagc gcctctgcga cgagaggaac ctcctccagg acccgaactt ccgcggaatc   2040
aaccggcagc ctgaccgcgg gtggaggggc tccactgata ttaccatcca gggcggggac   2100
gatgtgttca aggagaacta cgtcacgctc ccgggcacat tcgacgagtg ctaccccaca   2160
tacctgtacc agaagatcga tgagtcaaag ctcaaggcct acactcggta cgagctgcgc   2220
ggatacatcg aggactccca ggatctcgag atctacctca tccgctacaa tgcgaagcac   2280
gagactgtta acgtgccagg caccgggtcg ctgtggcccc tctcggcgca gtccccaatc   2340
gggaagtgcg gcgagccaaa tcgctgcgcg acccatctcg agtggaaccc tgacctggat   2400
tgcagctgca gggacggcga gaagtgcgct caccattctc accatttctc actggacatc   2460
gatgtgggct gcaccgacct caacgaggat ctgggcgtct gggttatttt caaaatcaag   2520
acccaggacg ggcacgctag gctgggcaac ctcgagttcc tcgaggagaa gccgctggtg   2580
ggcgaggctc tggctagggt taagagggcg gagaagaagt ggagggacaa gcgggagaag   2640
```

ctggagctgg agacaaacat cgtctacaag gaggcgaaga agtctgtcga tgctctcttc 2700
gttaattcac agtacgacag gctgcaggcc gatacgaaca tcgcgattat ccacgctgcc 2760
gacaagcggg tgcattccat tcgcgaggcc tacctcccag agctgagcgt tatccctggc 2820
gtgaacgcgg ctattttcga ggagctggag ggccgcatct tcaccgccta cagcctgtac 2880
gacgcgagga acgttattaa gaatggggat ttcaacaatg gcctctcgtg ctggaacgtg 2940
aagggccacg tggacgtcga ggagcagaac aatcatcgct ctgtcctcgt ggtcccggag 3000
tgggaggctg aggtttcaca ggaggttagg gtgtgcccgg gcaggggata catcctccgc 3060
gtcacggcgt acaaggaggg ctacggggag ggctgcgtta caattcacga gatcgaggac 3120
aatactgatg agctgaagtt ctccaactgc gtggaggagg agatctaccc aaacaatact 3180
gtcacctgca acgactacac ggccacacag gaggagtacg agggcactta caccagccgc 3240
aatagggggt acgacggcgc ctacgagtcg aactcgtctg tgcctgcgga ttacgcgtct 3300
gcttacgagg agaaggctta caccgacggc aggcgcgata acacatgcga gagcaatagg 3360
gggtacggcg actacacccc actccctgcg ggctacgtga cgaaggagct ggagtacttc 3420
ccggagaccg acaaggtctg gcttgagatc ggggagacgg agggcacatt catcgtggat 3480
tccgtcgagc tgctgatcat ggaggagta 3509

<210> SEQ ID NO 27
<211> LENGTH: 3510
<212> TYPE: DNA
<213> ORGANISM: Artificial Sequence
<220> FEATURE:
<223> OTHER INFORMATION: Synthetic mutant BT-0030 coding sequence

<400> SEQUENCE: 27
atggaggtca accaccagaa tgagtgcgtt ccatacaact gcctgaagaa tcctaagatc 60
gagatgctcg acatcgaggg catttcgtcc aggtcgaggg agcaggtggc cgagatctcc 120
ctgggcctca caaggttcct cctggagtct ctcctgccgg gcgcttcatt cggcttcggg 180
ctgttcgata tcatttgggg cgtgatcggc ccggaccagt ggtcgctgtt cctcacccag 240
attgagcagc tcatcgacca gcgcattgag gcgcacgtga ggaaccaggc tatttcgagg 300
ctggagggcc tgggggactc ctacgaggtc tacatcgaga gcctgaggga gtgggaggct 360
tccccgaaca atgagtctct ccagcaggat gtgaggaacc ggttcagcaa caccgacaat 420
gctctgatta cggccatccc gattctccgc gagcagggct tcgagatccc gctcctgacc 480
gtctacgtgc aggctgccaa cctgcacctc agcctcctgc gggatgcggt gtacttcggg 540
cagaggtggg gcctcgacac ggccacggtc aacaatcact acaaccggct gatcaacctc 600
attaatacct actccgatca ttgcgctcag tggttcaacc gcgggctgga caatttcggc 660
gtggtcactg cccgctacct cgatttccag agggaggtga ccatctcagt cctggatatt 720
gttgcgctct tcccaaacta cgacatcagg acatacccta ttcagactct gtcccagctc 780
acccgggaga tctacacgtc tccagtcgcg gagcctggcg cttcactcaa cgttgacctg 840
aggaatatcc tccgggagcc acacctgatg gatttcctga cacgcctcgt gatctacact 900
ggcgtccagg gcgggatcta ccactgggct gggcatgaga tctcgtctag gaccacgggc 960
aacctgtcat ccaatatcca gttcccactg tacggcacgt ccgccaacgc tgaccggcct 1020
ttcaatctgg cgatccatta ctccgagacc atctaccgca cgctcagcgc tccaatctac 1080
tccgtcagcg gcgggatttc gccgaacagg accagggccg ttgagggcgt gcgcttcctc 1140

-continued

```
acagctaggg acaacaatct gaactcgctc ccgttcctgt accggaagga gggctcactg   1200
gattccttca ccgagctgcc gccggaggac gagaacgagc caccttacat cggctactcc   1260
cacaggctgt gccatgccag gttcgctcgc agctcggttg tgctcgagcc gtctaacttc   1320
gctcgcatcc cggtgttctc atggacccac cgctccgccg gcccgacaaa tgaggtctct   1380
tcatccagga tcactcagat tccttgggtt aaggctcata ccctggatag cggcgccttc   1440
gtgattaagg gcccggggtt caccggcggg gacatcctca ccaggccaaa cctcgggaca   1500
ctgggcgcgc tcagggtcac actgactggc cagctcccgc agacttacaa catccggatt   1560
cgctacgcct ccattgcgaa tcgcggcggc accctcatct tctctcagcc gccatcatac   1620
ggcctcacat tcccgaagac tatggacatc gatgagcccc tgacgtcgcg ctctttcgcc   1680
aggacaactc tcttcacacc aattaccttc acgcaggccc aggcggagct gaacctcact   1740
atccagcagg gcgtgtacat cgataggatt gagttcatcc ctgtcaatgc cacgttcgag   1800
gcggagtacg acctggagcg ggctcagaag gccgtgaacg cgctcttcac cagctcgaat   1860
cagctgggcc tcaagacaga cctgactgat taccacattg atcaggtgtc gaacctggtc   1920
gactgcctct ctgatgagtt ctgcatcgac gagaagcgcg agctgagcga gaaggtcaag   1980
catgccaagc ggctctcaga cgagcgcaac ctcctgcagg attccaactt caggggcatc   2040
aataggcagc cggacagggg gtggaggggc tccaccgata tcacgattca gggcgggaac   2100
gacgttttca aggagaatta cgtgaccctg ccaggcacgt tcgacgagtg ctaccctacg   2160
tacctctacc agaagatcga tgagtccaag ctgaaggcgt acacacgcta ccagctccgg   2220
ggatacatcg aggacagcca ggatctggag atctacctca tcaggtacaa cgccaagcac   2280
gagactgtta atgtgccggg caccgggagc ctgtggccac tcagcgtgga gtcgcctatc   2340
gggaagtgcg gcgagcccaa ccgctgcgtc ccacagctgg agtggaacag caatctcgac   2400
tgctcctgca gggatggcga gaagtgcgcc caccattccc accatttcag cctcgacatc   2460
gatgtggggt gcacggacct gcacgacgat ctcggcgtct gggttatttt caagatcaag   2520
acgcaggacg ggcatgctag gctgggcaac ctcgagttcc tcgaggagaa gccgctggtg   2580
ggcgaggctc tggctagggt caagagggcg gagaagaagt ggcgggacaa gcgcgagaca   2640
ctgcagctcg agactaacat cgtttacaag gaggccaagg agtcggtgga cgctctgttc   2700
gccaactctc agtacaatcg cctccaggct gatacgaaca ttgccatgat ccacgctgcc   2760
gacaagaggg tgcatcgcat ccgcgaggct tacctccccg agctgtctgt tatccccggg   2820
gtgaacgcgg gcattttcga ggagctggag ggccggattt tcaccgcctt cagcctctac   2880
gatgcgcgca acgtcatcaa gaattcagac ttcaacaatg ggctgtcctg ctggaacgtc   2940
aagggccacg ttgacatcga ggagcagaac aatcatagga gcgttctcgt cgttccggag   3000
tgggaggcgg aggtgtcgca gaaggtgcac gtctgcccgg gcaggggata catcctgcgg   3060
gtcaccgcct acaaggaggg ctacggggag ggctgcgtta ctattcacga gatcgaggac   3120
cataccgatg agctgaagtt ccgcaactgc gaggaggatg aggtgtaccc gaacaataca   3180
aggacttgca atgcgtaccc ggctgaccag gaggggtacg agggcgcctg cacttctcgc   3240
aacagggggt acgacgaggt ctacggcaat accccgtcac tccccgccga ttacgcgcca   3300
atctacgagg agaacgccta cacggacggg aggaggggca atccttgcga gtcttcacgc   3360
gggtacggcg actacacgcc actgcctgcc ggctacgaga caaaggagct ggagtacttc   3420
ccggagaccg atacggtgtg gatcaagctt ggggagacag agggcacttt catcgtcgac   3480
tccgttgagc tgctgatcat ggaggagtaa                                    3510
```

<210> SEQ ID NO 28
<211> LENGTH: 2160
<212> TYPE: DNA
<213> ORGANISM: Artificial Sequence
<220> FEATURE:
<223> OTHER INFORMATION: Synthetic mutant BT-0031 coding sequence

<400> SEQUENCE: 28
atgaagctca agaatccaga caagcaccag agcctgtcca gcaacgctaa ggtggacaag 60
atcgccacag attcgctcaa gaatgagact gacattgagc tgaagaacat gaacaatgag 120
gattacctcc gcatgtcgga gcatgagtct atcgaccctt tcgtttcggc ctctactatt 180
cagaccggca tcgggattgc cggcaagatc ctcggcaccc tcggcgtgcc gttcgctggc 240
cagatcgctt ctctctactc attcattctg ggcgagctgt ggcctaaggg gaagagccag 300
tgggagatct tcatggagca cgtggaggag atcattaatc agaagattct gacctacgcg 360
aggaacaagg ctctgtcgga cctcaggggc ctgggggatg ccctcgctgt ctaccatgag 420
tccctggaga gctgggttaa gaatcgcaac aatacgcggg ctcgctccgt ggtcaagaac 480
cagtacatcg ccctcgagct gatgttcgtc cagaagctgc catcgttcgc cgtgtccggc 540
gaggaggtcc cgctcctgcc aatctacgcc caggctgcca acctccacct cctgctcctg 600
cgcgacgctt ctatcttcgg caaggagtgg gggctgtcag cgtccgagat tagcacattc 660
tacaacaggc aggttgagag gactcgggac tactcggatc attgcgtgaa gtggtacaac 720
accggcctca acaatctgag gggaaccaac gccaagagct gggtccggta caaccagttc 780
cgcaaggaca tgacactcat ggtgctcgat ctggtcgcgc tcttcccatc atacgacact 840
ctggtctacc caatcaagac cacgtcccag ctgactaggg aggtttacac cgatgccatt 900
ggcacggttc accccctcagg ggcggtggcc tccacaactt ggtacaacaa taacgcgccg 960
agcttctcga ccatcgaggc tgccgttgtg cggaaccccc acctcctgga cttcctcgag 1020
caggtgacca tctactcgct cctgtctagg tggtcaaata cgcagtacat gaacatgtgg 1080
ggcgggcata agctcgagtt ccggactatc ggcggcaccc tcaacacaag cactcagggc 1140
tcgaccaata cgtctattaa cccagtgacg ctccctttca catctaggga cgtctaccgg 1200
acagagtcac tggccggcct caatctgttc ctcacgcagc ccgtgaacgg cgtccccagg 1260
gttgacttcc actggaagtt cgtcacccat ccaatcgcgt ccgataactt ctactaccct 1320
ggctacgctg gcattgggac gcagctccag gactccgaga atgagctgcc gcccgagacc 1380
accggccagc ccaactacga gtcttactca cacaggctct cccatatcgg cctgatttcc 1440
gccagccacg ttaaggcgct cgtgtacagc tggacacatc gctcggccga caggacaaat 1500
actatcaact cggattctat cacgcagatt ccgctcgtga aggccttcaa cctgccgtcg 1560
ggcgcctcgg tcgttcgggg ccccgggttc accggcgggg acatcctgcg caggaccaac 1620
acgggcacat tcggggatat ccgcgtcaat attaacccac ctttcgccca gcgctacagg 1680
ctccgcatcc gctacgcgtc cacaactaat ctggagttcc acaccagcat caacggcaag 1740
gctattaatc aggggaactt ctcggctacc atgaaccgcg gcgaggacct cgattacaag 1800
gccttcagga cggtgggctt caccacgccc ttctcattct ccaacgcgca gtcgactttc 1860
accatcggcg cttggaattt ctctctgggg aacgaggtct acatcgacag gattgagttc 1920
gtgccggtcg aggttaccta cgaggcggag cacgatttcg agaaggcgca ggaggaggtg 1980
acggctctct tcacgagcac aaatccaggc ggcctgaaga cgaacgtcac agagtaccat 2040
atcgaccagg tctcgaatct cgttgagagc ctgtcgaacg agttctacct cgatgagaag 2100
cgggagctgt tcgagctcgt gaagtacgcc aagcagctgc accttggccg caacatgtaa 2160

<210> SEQ ID NO 29
<211> LENGTH: 3495
<212> TYPE: DNA
<213> ORGANISM: Artificial Sequence
<220> FEATURE:
<223> OTHER INFORMATION: Synthetic mutant BT-0201 coding sequence

<400> SEQUENCE: 29
atggagcgca acaatcagga ccagtgcatc ccgtacaact gcctcaacaa tcccgaggtt 60
ggcattctgg atatcgagaa cttcaatctg gagctggtgt cccaggtgtc agtcggcctc 120
accaggttcc tcctggaggc ctccatccca ggcgccgggt tcgctctggg cctcttcgac 180
atcatttggg gcgccctcgg cgtggatcag tggtccctgt tcctcgctca gattgagcag 240
ctgatcaatg agcgcattac caccgtggag aggaaccgcg ctatccaggc cctgtcgggc 300
ctctccagct cgtacgaggt ctacattgag gctctcaggg agtgggagaa cgacctggat 360
aatccggctt ctagggacag ggtggtggct aggttccggg ctaccgacaa ctcactcatt 420
acggatatcc cgctcctgga gatccccggc ttcgagattg ccacactgtc cgtgtacacg 480
caggcggcca acctgcacct cgccctcctg agggacgctg tctacttcgg ggagcgctgg 540
ggcctgacac agactaacat cgaggacctc cacacacggc tgactcgcta cattcaggag 600
tactccgatc attgcgcgcg ctggtacaac cagggcctca acaatattgg cggaatcaac 660
acccgctacc tcgacttcca gcgggagctg acgatcagcg tcctcgacat tgttgccctg 720
ttcccgaact acgatatccg gacctaccca attcctacgc agagccagct cacacgcgag 780
atctacactt cgccggttgt ggcccccggc gtgaattgga ttctgtcgat ctctaacgtc 840
ctcagggcgc cacacctgat ggacttcttc gatcggatca ttatctacac gggcacggtg 900
cgctcaaccc ctcactggga ggggcatgag gtcatctcca ggaggacggg ccaggggaac 960
gagattagga gcccgctcta cggcgtggct gctaatgccg agccgccagt tacgatcagg 1020
ccaacgggct tcacggacga gcagcggcag gtctaccgcg ttctgtccag ggtcgccagc 1080
ttccggaact cgggcacaaa tttctcactc gttgacgcgg cttccttcct gactatcttc 1140
agcgcgtctt caatctaccg caacggcttc gggttcaatg ctgacaccat cgatgagatt 1200
ccaatcgagg ggacggaccc atacatcggc tactcccacc gcctctgcca tgtgggcttc 1260
accgcctcca gcccgttcat cagccagtac gcgagggctc ccgtcttctc ctggacacac 1320
cggagcgcta cattcactaa caccatcgac ccagagcgca ttacgcagat ccctatggtg 1380
aaggcctaca acctgcatgc gggcgccaca gtcgttaggg gcccggggtt cactggcggg 1440
gacctcctgc ggcgcacgaa cacaggcact ttcgcggata tcagggtcaa tattaccggc 1500
cccctctccc agcgctaccg cgtgcgcatc cgctacgctt ctacaactga cctgcagttc 1560
ttcaccagga tcaacgggac gagcgtgaac cagggcaatt tccagcggac gatgaaccgc 1620
ggggacaatc tcgagtctgg caacttccgg acagccgggt tctcaactcc attctcattc 1680
tccaatgctc agtccacctt cacgctgggc acccaggcct tcagcaacca ggaggtctac 1740
attgacagga tcgagttcgt gcctgctgag gtcacgttcg aggccgagtc cgatctcgag 1800
cgggctcaga aggccgtgaa cgcgctgttc acaagcactt cgcagctggg cctcaagaca 1860
aacgtcactg gctaccacat cgaccaggtt tcgaatctcg tggcgtgcct gtctgacgag 1920
ttctgcctcg atgagaagcg cgagctgtcg gagaaggtga agcacgccaa gcggctctct 1980
gacaagcgca acctcctgca ggacccgaac ttcaggggaa tcaacaggca gcctgaccac 2040
ggctggaggg gctcgaccga tattacgatc cagggcgggg acgatgtttt caaggagaac 2100
tacgtgaccc tcccaggcac gttcgacgag tgctacccta catacctgta ccagaagatc 2160
gatgagtcca agctcaaggc gtacactcgc taccagctga ggggatacat cgaggactca 2220
caggatctcg agatctacct catccgctac aattccaagc acgagatcgt taacgtgccc 2280
ggcaccgggt cgctgtggcc actctctgtg gagaatcaga tcgggccatg cggcgagcct 2340
aaccggtgcg ccccgcacct cgagtggaat ccagacctgc attgctcctg ccgggatggc 2400
gagaagtgcg tccaccattc tcaccatttc tcactcgaca tcgatgttgg ctgcaccgac 2460
ctcaacgagg atctgggggt gtggctcatt ttcaagatca agacccagga cgggcacgcc 2520
aggctgggca acctcgagtt cctcgaggag gagcccctcc tgggcgaggc tctggctagg 2580
gtgaagaggg ccgagaagaa gtggcgcgac aagagggaga agctgcagct cgagaccaac 2640
atcgtctaca aggaggcgaa ggagtcagtg gatgctctct tcgtcaactc ccagtacgac 2700
cgcctgcagg ccgatacgaa tattgcgatg atccacgccg cggacaagag ggtgcatcgc 2760
atccgcgagg cctacctccc agagctgtcg gtcatccctg gcgttaacgc tgccattttc 2820
gaggagctgg agggccgcat cttcaccgcc tactctctgt acgacgcgag gaacgtgatt 2880
aagaacggga atttcaacaa tggcctcctg tgctggaacg tcaagggcca cgtcgatgtt 2940
gaggagcaga acaatcatcg cagcgtgctc gtcatccccg agtgggaggc cgaggtctcg 3000
cagaaggtta gggtgtgccc gggcagggga tacatcctgc gcgtgaccgc ttacaaggag 3060
ggctacgggg agggctgcgt caccattcac gagatcgagg acaatacgga tgagctgaag 3120
ttctccaact gcgttgagga gggctacccg aacaataccg tgacgtgcaa cgagtacacc 3180
atgaaccagg gggtgggcga gtgcactgac gcttgcaacg ttcgcaatag gggctacgag 3240
gatgcgtacg ggcacaaccc aagcacccct gtgcattaca ccacgccata cgaggaggag 3300
acatacactg acgagaggcg ggagaaccct tgcgaggcca ataagggcta cgtgaactac 3360
acaccgctcc ccgtgggcta cgtgactaag gagctggagt acttccccga gaccgacacg 3420
gtctggattg agatcgggga gacagagggc actttcctcg ttgatagcgt ggagctgctg 3480
atcatggagg agtaa 3495

<210> SEQ ID NO 30
<211> LENGTH: 3501
<212> TYPE: DNA
<213> ORGANISM: Artificial Sequence
<220> FEATURE:
<223> OTHER INFORMATION: Synthetic mutant BT-0202 coding sequence

<400> SEQUENCE: 30
atgaagatca acaatcagaa ccagtgcatt ccgtacaact gcctgagcaa tccggaggag 60
gtgctcctgg acggcgagcg cattctgccg gacatcgatc ccctcgaggt cagcatgtcg 120
ctcctgcagt tcctcctgaa caatttcgtg ccgggcgggg gcgtcatctc gggcctgatc 180
aacaagattt ggggcgccct ccggccgtcc gagtgggagc tgttcctcgc ccagattgag 240
cagctgatcg acaggaggat tgaggcggcg gtcagggcta aggccatcgc tgagctggag 300
gggctgggcc ggtcttacca gctctacggc gaggcgttca aggagtggga gaagacaccc 360
gataacaccg cggcgcgctc cagggtgacc gagcgcttca ggatcattga cgcgcagatc 420
gaggctaaca ttccatcttt ccgcgtttca ggcttcgagg tgcctctcct gtctgtctac 480

-continued

```
acccaggcgg ctaacctgca tctcgccctc ctgcgggatt cagtggtgtt cggcgagagg    540
tgggggctga ccaccacaaa cgtgaatgac atctacaacc gccaggtcaa gaggattgac    600
gagtacagcg atcactgcgt cgacacctac aagacggagc tggagcgcct cgagttctcc    660
agcatcgcgc agtggaggat ctacaaccag ttccggaggg agctgaccct caccgtcctc    720
gatatcgttg ccctgttccc gaattacgac ggccgcctgt accccatcag gaccatttcc    780
cagctcacgc gggacatcta cacatctcca gtttcagagt tctactacgg ccctatctac    840
aactacaata ttgtggggag gctcactgag cagcagctga ggcggccaca tctcatggat    900
ttcttcaact ccatgatcat gtacaccagc gacaatcgca gggagcacta ctggtccggc    960
ctggagatga aggccacaga cactagcggg aaccaggtgt cgttccccct ggctggcacg   1020
agggggaatt ccgccccgcc agtcacagtt aggaacaatg ggagagggcgt ctaccgcatc   1080
ctctctgagc cattctactc gtctcctttc ctgggcacct ccgtgctggg ctcccgcggc   1140
gaggagttcg ccttcgcgag caacactacc acgtccctgc cgagcactat ctacaggaat   1200
cgcggcaccg tggattcgct cgtctctatt ccacctcagg actactcggt cccgccccac   1260
aggggctact cccacctcct gtctcatgtt acgatgcaca actcatcccc gatcttccac   1320
tggacacatc gctccgccac cccacgcaat acgattgacc ctgatagcat cacgcagatt   1380
cccgttgtga aggcctcaca tctgtccggg ggcagcgtta tcaaggggcc gggccacaca   1440
gggggcgacc tgatttccct ccccgtcaac aatttcactc acttccgcat cccgttccag   1500
gccaacaccc cgcagcgcta ccgcatccgc atccgctacg ctgccgactc ggatggcacc   1560
ctggattcgg gggtgttcct ctcagctgcg gccggggacg gcttcaacac aacttcgtac   1620
agggctacca tgtctccggg cggctccctc acatctaggg atttccagtt cctggacctc   1680
aacacatcat tcacttccga cgtcgcgtcc aatctgtggc tccatttcat caggtacatt   1740
cggccaggca acctgtacat cgatagggcc gagttcattc ctgtggacgc caccttcgag   1800
gcgggctaca atctcgagcg ggcgcagaag gctgtgaacg ccctgttcac ctccacgaat   1860
cagaagggcc tccagaccga cgtcacggat taccacatcg atcaggtttc aaacctcgtg   1920
gattgcctgt ccgacgagtt ctgcctggac gagaagcgcg agctgagcga gaaggtcaag   1980
caggcgaaga ggctgtctga tgagcggaac ctcctgcagg actcaaactt ccggggaatc   2040
aacagggagc aggatagggg ctggaggggg tcgacacata tcactattca gggcggcaac   2100
gacgtcttca aggagaattt cgttactctg ccgggcgcgt tcgatgcttg ctaccccacc   2160
tacctctacc agaagatcga cgagtccaag ctgaaggcct acacccgcta cgagctgcgg   2220
ggatacatcg aggacagcca ggacctcgat atctacctga ttcgctacaa cacaaagcac   2280
gagactctca atgtgccggg cactaagtcc ccctggtccc tgtgcacgga gtccccactc   2340
ggcaagtgcg gggagcctaa caggtgcgcc tcccagatcg agtggaatcc ggacctggat   2400
tgctcctgca gggacggcga gaagtgcgct caccattcac accatttctc cctcgacatc   2460
gatgtgggct gcacggacct caacgagaat ctggggatct gggtcatttt caagatcaag   2520
acgcaggacg gccacgccag gctggggaac ctcgagttcc tcgaggagaa gccgctcctg   2580
ggcgaggctc tggctagggt caagcgcgcc gagaagaagt ggagggacaa gcgggagaag   2640
ctccagagcg agacgaacat cgtgtacaag gaggccaagg aggcggttga tggcctgttc   2700
gtggactcgc agtacgagcg cctccaggcg gataccaaca ttgctatgat ccacgctgcc   2760
gacaagcacg tgcatcagat cagggaggtc tacttcccag agctgtccgt catccctggc   2820
gttaacgcgg ctattttcga ggagctggag ggccggatct tcacggccta ctcactctac   2880
```

-continued

```
gatgcgcgca acgtcattaa gaatggcgac ttcaacaatg ggctgtcctg ctggaacgtt   2940

aagggccatg tggacgtcga ggttcagaac aatcaccgct cagtgctcgt catcgctgag   3000

tgggaggcgg aggtgtccca ggaggttccg gtgtgcccgg ggaggggata catcctgagg   3060

gttaccgcct acaaggaggg gtacggcgag gggtgcgtga cgattcatga gatcgaggac   3120

cacacagatg agctgaagtt caggaactgc gaggaggagg aggtttaccc gaacaataca   3180

gtgacttgca atggctacac cgcgacgcag gaggagtaca aggatgctta cacctcgagg   3240

aacaggggct acgacgaggc ctacgggaac aatccaagcg tccctgctga ttacgcctcg   3300

gtttacgagg agaaggctta cacggacggc aggagggaga acccatgcga gatggagagg   3360

ggctacactc cactgcctgt gggatacatc accaaggagc tggagtactt ccctgagaca   3420

gatactgtct ggatcgagct tggcgagacc gaggggacgt tcctcattga cagcgtggag   3480

ctgctgctca tggaggagta a                                              3501


<210> SEQ ID NO 31
<211> LENGTH: 1181
<212> TYPE: PRT
<213> ORGANISM: Bacillus thuringiensis

<400> SEQUENCE: 31

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255
```

-continued

```
Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
```

```
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Val Tyr Leu Ile Arg Tyr
        755                 760                 765

Asn Ala Lys His Glu Thr Leu Asn Val Pro Gly Thr Gly Ser Leu Trp
    770                 775                 780

Pro Leu Ala Val Lys Ser Pro Ile Gly Arg Cys Gly Glu Pro Asn Arg
785                 790                 795                 800

Cys Ala Pro Arg Ile Glu Trp Lys Pro Asp Val Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Lys Ile Gly Asn Leu Glu
    850                 855                 860

Phe Leu Glu Glu Lys Leu Leu Leu Gly Glu Ala Leu Ala Arg Val Lys
865                 870                 875                 880

Lys Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asp Ser Gln Tyr Asn Arg Leu Gln Thr Asp Thr Asn Ile Ala Met
        915                 920                 925

Ile His Ala Ala Asp Lys Arg Val His Arg Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Leu Ile Phe Thr Ala Phe Ser Leu Tyr Asp Ala Arg Asn
                965                 970                 975

Val Ile Lys Asn Gly Asp Phe Asn Tyr Gly Leu Ser Cys Trp Asn Val
            980                 985                 990

Lys Gly His Val Asp Val Glu Glu  Gln Asn Asn His Arg  Ser Val Leu
        995                 1000                1005

Val Ile  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035

Gly Tyr  Gly Glu Gly Cys Val  Thr Ile His Glu Ile  Glu Asp Asn
    1040                1045                1050

Thr Asp  Glu Leu Lys Phe Ser  Asn Cys Val Glu Glu  Glu Val Tyr
    1055                1060                1065

Pro Asn  Asn Thr Val Thr Cys  Asn Asp Tyr Thr Ala  Thr Gln Glu
    1070                1075                1080

Glu Tyr  Glu Gly Thr Tyr Thr  Ser Arg Asn Arg Gly  Tyr Asp Gly
    1085                1090                1095
```

```
Ala Tyr  Glu Ser Asn Ser Ser  Val Pro Ala Asp Tyr  Ala Ser Ala
    1100                 1105                 1110

Tyr Glu  Glu Lys Ala Tyr Thr  Asp Gly Arg Arg Asp  Asn Pro Cys
    1115                 1120                 1125

Glu Ser  Asn Arg Gly Tyr Arg  Asp Tyr Thr Pro Leu  Pro Ala Gly
    1130                 1135                 1140

Tyr Val  Thr Lys Glu Leu Glu  Tyr Phe Pro Glu Thr  Asp Lys Val
    1145                 1150                 1155

Trp Ile  Glu Ile Gly Glu Thr  Glu Gly Thr Phe Ile  Val Asp Ser
    1160                 1165                 1170

Val Glu  Leu Leu Leu Met Glu  Glu
    1175                 1180


<210> SEQ ID NO 32
<211> LENGTH: 1176
<212> TYPE: PRT
<213> ORGANISM: Bacillus thuringiensis

<400> SEQUENCE: 32

Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
```

```
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700
```

```
Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
    850                 855                 860

Leu Glu Glu Lys Pro Leu Val Gly Glu Ala Leu Ala Arg Val Lys Ile
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln  Asn Asn Gln Arg Ser  Val Leu Val
        995                 1000                1005

Val Pro  Glu Trp Glu Ala Glu  Val Ser Gln Glu Val  Arg Val Cys
    1010                1015                1020

Pro Gly  Arg Gly Tyr Ile Leu  Arg Val Thr Ala Tyr  Lys Glu Gly
    1025                1030                1035

Tyr Gly  Glu Gly Cys Val Thr  Ile His Glu Ile Glu  Asn Asn Thr
    1040                1045                1050

Asp Glu  Leu Lys Phe Ser Asn  Cys Val Glu Glu Glu  Ile Tyr Ser
    1055                1060                1065

Asn Asn  Thr Val Thr Cys Asn  Asp Tyr Thr Val Asn  Gln Glu Glu
    1070                1075                1080

Tyr Gly  Gly Ala Tyr Thr Ser  Arg Asn Arg Gly Tyr  Asn Glu Ala
    1085                1090                1095

Pro Ser  Val Pro Ala Asp Tyr  Ala Ser Val Tyr Glu  Glu Lys Ser
    1100                1105                1110
```

```
Tyr Thr  Asp Gly Arg Arg Glu  Asn Pro Cys Glu Phe  Asn Arg Gly
    1115                 1120                 1125

Tyr Arg  Asp Tyr Thr Pro Leu  Pro Val Gly Tyr Val  Thr Lys Glu
    1130                 1135                 1140

Leu Glu  Tyr Phe Pro Glu Thr  Asp Lys Val Trp Ile  Glu Ile Gly
    1145                 1150                 1155

Glu Thr  Glu Gly Thr Phe Ile  Val Asp Ser Val Glu  Leu Leu Leu
    1160                 1165                 1170

Met Glu  Glu
    1175


<210> SEQ ID NO 33
<211> LENGTH: 1176
<212> TYPE: PRT
<213> ORGANISM: Bacillus thuringiensis

<400> SEQUENCE: 33

Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300
```

-continued

```
Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720
```

-continued

```
Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
    850                 855                 860

Leu Glu Glu Lys Pro Leu Val Gly Glu Ala Leu Ala Arg Val Lys Ile
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln  Asn Asn Gln Arg Ser  Val Leu Val
        995                 1000                1005

Val Pro  Glu Trp Glu Ala Glu  Val Ser Gln Glu Val  Arg Val Cys
    1010                1015                1020

Pro Gly  Arg Gly Tyr Ile Leu  Arg Val Thr Ala Tyr  Lys Glu Gly
    1025                1030                1035

Tyr Gly  Glu Gly Cys Val Thr  Ile His Glu Ile Glu  Asn Asn Thr
    1040                1045                1050

Asp Glu  Leu Lys Phe Ser Asn  Cys Val Glu Glu Glu  Ile Tyr Ser
    1055                1060                1065

Asn Asn  Thr Val Thr Cys Asn  Asp Tyr Thr Val Asn  Gln Glu Glu
    1070                1075                1080

Tyr Gly  Gly Ala Tyr Thr Ser  Arg Asn Arg Gly Tyr  Asn Glu Ala
    1085                1090                1095

Pro Ser  Val Pro Ala Asp Tyr  Ala Ser Val Tyr Glu  Glu Lys Ser
    1100                1105                1110

Tyr Thr  Asp Gly Arg Arg Glu  Asn Pro Cys Glu Phe  Asn Arg Gly
    1115                1120                1125

Tyr Arg  Asp Tyr Thr Pro Leu  Pro Val Gly Tyr Val  Thr Lys Glu
```

```
    1130                1135                1140

Leu Glu  Tyr Phe Pro Glu Thr  Asp Lys Val Trp Ile  Glu Ile Gly
    1145                1150                1155

Glu Thr  Glu Gly Thr Phe Ile  Val Asp Ser Val Glu  Leu Leu Leu
    1160                1165                1170

Met Glu  Glu
    1175


<210> SEQ ID NO 34
<211> LENGTH: 715
<212> TYPE: PRT
<213> ORGANISM: Bacillus thuringiensis

<400> SEQUENCE: 34

Met Lys Ser Lys Asn Gln Asn Met His Gln Ser Leu Ser Asn Asn Ala
1               5                   10                  15

Thr Val Asp Lys Asn Phe Thr Gly Ser Leu Glu Asn Asn Thr Asn Thr
            20                  25                  30

Glu Leu Gln Asn Phe Asn His Glu Gly Ile Glu Pro Phe Val Ser Val
        35                  40                  45

Ser Thr Ile Gln Thr Gly Ile Gly Ile Ala Gly Lys Ile Leu Gly Asn
    50                  55                  60

Leu Gly Val Pro Phe Ala Gly Gln Val Ala Ser Leu Tyr Ser Phe Ile
65                  70                  75                  80

Leu Gly Glu Leu Trp Pro Lys Gly Lys Ser Gln Trp Glu Ile Phe Met
                85                  90                  95

Glu His Val Glu Glu Leu Ile Asn Gln Lys Ile Ser Thr Tyr Ala Arg
            100                 105                 110

Asn Lys Ala Leu Ala Asp Leu Lys Gly Leu Gly Asp Ala Leu Ala Val
        115                 120                 125

Tyr His Glu Ser Leu Glu Ser Trp Ile Lys Asn Arg Asn Asn Thr Arg
    130                 135                 140

Thr Arg Ser Val Val Lys Ser Gln Tyr Ile Thr Leu Glu Leu Met Phe
145                 150                 155                 160

Val Gln Ser Leu Pro Ser Phe Ala Val Ser Gly Glu Glu Val Pro Leu
                165                 170                 175

Leu Pro Ile Tyr Ala Gln Ala Ala Asn Leu His Leu Leu Leu Leu Arg
            180                 185                 190

Asp Ala Ser Ile Phe Gly Lys Glu Trp Gly Leu Ser Asp Ser Glu Ile
        195                 200                 205

Ser Thr Phe Tyr Asn Arg Gln Val Glu Arg Thr Ser Asp Tyr Ser Asp
    210                 215                 220

His Cys Thr Lys Trp Phe Asp Thr Gly Leu Asn Arg Leu Lys Gly Ser
225                 230                 235                 240

Asn Ala Glu Ile Trp Val Lys Tyr Asn Gln Phe Arg Arg Asp Met Thr
                245                 250                 255

Leu Met Val Leu Asp Leu Val Ala Leu Phe Gln Ser Tyr Asp Thr His
            260                 265                 270

Met Tyr Pro Ile Lys Thr Thr Ala Gln Leu Thr Arg Glu Val Tyr Thr
        275                 280                 285

Asn Ala Ile Gly Thr Val His Pro His Pro Ser Phe Thr Ser Thr Thr
    290                 295                 300

Trp Tyr Asn Asn Asn Ala Pro Ser Phe Ser Ala Ile Glu Ala Ala Val
305                 310                 315                 320
```

-continued

```
Ile Arg Ser Pro His Leu Leu Asp Phe Leu Glu Gln Val Thr Ile Tyr
                325                 330                 335

Ser Leu Leu Ser Arg Trp Ser Asn Thr Gln Tyr Met Asn Met Trp Gly
            340                 345                 350

Gly His Lys Leu Glu Phe Arg Thr Ile Gly Gly Thr Leu Asn Thr Ser
        355                 360                 365

Thr Gln Gly Ser Thr Asn Thr Ser Ile Asn Pro Val Thr Leu Pro Phe
    370                 375                 380

Thr Ser Arg Asp Ile Tyr Arg Thr Glu Ser Leu Ala Gly Leu Asn Leu
385                 390                 395                 400

Phe Leu Thr Gln Pro Val Asn Gly Val Pro Arg Val Asp Phe His Trp
                405                 410                 415

Lys Phe Val Thr His Pro Ile Ala Ser Asp Asn Phe Tyr Tyr Pro Gly
            420                 425                 430

Tyr Ala Gly Ile Gly Thr Gln Leu Gln Asp Ser Glu Asn Glu Leu Pro
        435                 440                 445

Pro Glu Thr Thr Gly Gln Pro Asn Tyr Glu Ser Tyr Ser His Arg Leu
    450                 455                 460

Ser His Ile Gly Leu Ile Ser Ala Ser His Val Lys Ala Leu Val Tyr
465                 470                 475                 480

Ser Trp Thr His Arg Ser Ala Asp Arg Thr Asn Thr Ile His Ser Asp
                485                 490                 495

Ser Ile Thr Gln Ile Pro Leu Val Lys Ala His Thr Leu Gln Ser Gly
            500                 505                 510

Thr Thr Val Val Lys Gly Pro Gly Phe Thr Gly Gly Asp Ile Leu Arg
        515                 520                 525

Arg Thr Ser Gly Gly Pro Phe Ala Phe Ser Asn Val Asn Leu Asp Trp
    530                 535                 540

Asn Leu Ser Gln Arg Tyr Arg Ala Arg Ile Arg Tyr Ala Ser Thr Thr
545                 550                 555                 560

Asn Leu Arg Met Tyr Val Thr Ile Ala Gly Glu Arg Ile Phe Ala Gly
                565                 570                 575

Gln Phe Asn Lys Thr Met Asn Thr Gly Asp Pro Leu Thr Phe Gln Ser
            580                 585                 590

Phe Ser Tyr Ala Thr Ile Asp Thr Ala Phe Thr Phe Pro Thr Lys Ala
        595                 600                 605

Ser Ser Leu Thr Val Gly Ala Asp Thr Phe Ser Ser Gly Asn Glu Val
    610                 615                 620

Tyr Val Asp Arg Phe Glu Leu Ile Pro Val Thr Ala Thr Leu Glu Ala
625                 630                 635                 640

Val Thr Asp Leu Glu Arg Ala Gln Lys Ala Val His Glu Leu Phe Thr
                645                 650                 655

Ser Thr Asn Pro Gly Gly Leu Lys Thr Asp Val Ala Lys Asp His Tyr
            660                 665                 670

Thr Asn Thr Ile Ser Lys Ser Val Gln Ser Val Phe Arg Cys Arg Cys
        675                 680                 685

Ser Glu Arg Thr Arg Ile Tyr Arg Trp Gly Tyr Pro Ser Lys Lys Glu
    690                 695                 700

Tyr Trp Tyr Ile Trp Gly Tyr Thr Ser Lys Tyr
705                 710                 715
```

<210> SEQ ID NO 35
<211> LENGTH: 1094
<212> TYPE: PRT

<213> ORGANISM: Bacillus thuringiensis

<400> SEQUENCE: 35

```
Met Phe Leu Glu Gln Ile Glu Gln Leu Ile Asp Gln Arg Ile Glu Thr
1               5                   10                  15

Val Glu Arg Asn Arg Ala Ile Gln Thr Leu Ile Gly Leu Ser Asn Ser
            20                  25                  30

Tyr Asp Val Tyr Ile Glu Ala Leu Lys Glu Trp Glu Asn Asn Pro Asp
        35                  40                  45

Asn Ser Ala Ser Gln Glu Arg Val Arg Asn Arg Phe Arg Thr Thr Asp
    50                  55                  60

Asp Ala Leu Ile Thr Gly Ile Pro Leu Leu Ala Ile Pro Asn Phe Glu
65                  70                  75                  80

Ile Ala Thr Leu Ser Val Tyr Val Gln Ala Ala Asn Leu His Leu Ser
                85                  90                  95

Leu Leu Arg Asp Ala Val Phe Phe Gly Glu Arg Trp Gly Leu Thr Gln
            100                 105                 110

Ile Asn Val Asp Asp Leu Tyr Arg Arg Leu Thr Asn Asn Ile Arg Asn
        115                 120                 125

Tyr Ser Asp His Cys Ala Arg Trp Tyr Asn Glu Gly Leu Asp Asn Ile
    130                 135                 140

Ser Gly Leu Ser Arg Ser Ile Asn Phe Gln Arg Glu Val Thr Ile Ser
145                 150                 155                 160

Val Leu Asp Ile Val Ala Leu Phe Pro Asn Tyr Asp Ile Arg Thr Tyr
                165                 170                 175

Pro Ile Ser Thr Thr Ser Gln Leu Thr Arg Glu Ile Phe Thr Ser Pro
            180                 185                 190

Ile Val Val Pro Asn Asp Phe Ser Val Ala Tyr Glu Gly Val Arg Arg
        195                 200                 205

Ala Pro His Leu Phe Glu Phe Leu Glu Lys Leu Val Ile Tyr Thr Gly
    210                 215                 220

Asp Arg Ser Gly Ile Arg His Trp Ala Gly His Glu Ile Thr Ser Arg
225                 230                 235                 240

Arg Thr Asp Ser Tyr His Gly Ile Ile Arg Tyr Pro Leu Tyr Gly Thr
                245                 250                 255

Ala Ala Asn Ala Glu Ser Pro Tyr Thr Leu Ala Leu Gln Pro Ser Glu
            260                 265                 270

Ser Ile Tyr Arg Thr Leu Ser Glu Pro Ile Phe Ser Gln Thr Gly Gly
        275                 280                 285

Leu Ser Pro His Arg Arg Arg Val Val Glu Gly Val Glu Phe Ser Ile
    290                 295                 300

Val Asn Asn Asn Val Asn Pro Ser Ser Phe Val Tyr Arg Arg Lys Gly
305                 310                 315                 320

Ser Leu Asp Ser Phe Thr Glu Leu Pro Pro Glu Asp Glu Ser Val Pro
                325                 330                 335

Pro Tyr Ile Gly Tyr Ser His Gln Leu Cys His Val Gly Phe Gly Arg
            340                 345                 350

Thr Asn Val Ile Phe Glu Pro Ser Asn Phe Ala Arg Val Pro Val Phe
        355                 360                 365

Ser Trp Thr His Arg Ser Ala Thr Pro Thr Asn Thr Ile Asp Pro Asp
    370                 375                 380

Arg Ile Thr Gln Ile Pro Ser Val Lys Ala Ser Ser Leu Arg Asn Ser
385                 390                 395                 400
```

```
Thr Val Val Ser Gly Pro Gly Phe Thr Gly Gly Asp Ile Val Arg Met
                405                 410                 415

Gly Ala Val His Gln Ile Tyr Ala Thr Asp Leu Ser Met Asn Val Arg
            420                 425                 430

Pro Ser Val Ala Leu Ser Arg Tyr Leu Ile Arg Leu Arg Tyr Ala Cys
        435                 440                 445

Arg Gly Ser Ser Asn Ile Val Ile His Gly Pro Ser Ile Arg Phe Val
    450                 455                 460

Ser Leu Pro Ser Thr Met Ser Asn Asp Glu Pro Leu Thr Tyr Gln Ser
465                 470                 475                 480

Phe Arg Tyr Ala Ser Ile Thr Thr Pro Ile Thr Arg Pro Ile Tyr Asn
                485                 490                 495

Met Phe Asn Leu Ser Ile Ser Arg Ile Ser Gly Val Gln Asn Leu Phe
            500                 505                 510

Ile Asp Arg Ile Glu Phe Ile Pro Val Asp Ala Asn Phe Glu Ala Glu
        515                 520                 525

Arg Asp Leu Glu Arg Ala Gln Lys Ala Val Asn Ala Leu Phe Thr Ser
    530                 535                 540

Thr Asn Gln Arg Gly Leu Lys Ile Asp Val Thr Asp Tyr His Ile Asp
545                 550                 555                 560

Gln Val Ser Asn Leu Val Asp Cys Leu Ser Asp Glu Phe Cys Leu Asp
                565                 570                 575

Glu Lys Arg Glu Leu Ser Glu Lys Ser Lys His Ala Lys Arg Leu Ser
            580                 585                 590

Asp Glu Arg Asn Leu Leu Gln Asp Leu Asn Phe Lys Asp Ile Asn Arg
        595                 600                 605

Gln Pro Glu Arg Gly Trp Ser Gly Ser Thr Gly Ile Thr Ile Gln Gly
    610                 615                 620

Gly Asp Asp Val Phe Lys Glu Asn Tyr Val Thr Leu Pro Gly Thr Phe
625                 630                 635                 640

Asp Glu Cys Tyr Pro Thr Tyr Leu Tyr Gln Lys Ile Asp Glu Ser Lys
                645                 650                 655

Leu Lys Ala Tyr Thr Arg Tyr Gln Leu Arg Gly Tyr Ile Glu Asp Ser
            660                 665                 670

Gln Asp Leu Glu Ile Tyr Leu Ile Arg Tyr Asn Ala Lys His Glu Thr
        675                 680                 685

Val Asn Val Pro Gly Ser Gly Ser Leu Trp Pro Leu Ser Val Glu Ser
    690                 695                 700

Ser Val Gly Lys Cys Gly Glu Pro Asn Arg Cys Ala Ser Arg Met Glu
705                 710                 715                 720

Trp Asn Pro Asp Leu Asp Cys Ser Cys Arg Asp Gly Glu Lys Cys Ala
                725                 730                 735

His His Ser His His Phe Ser Leu Asp Ile Asp Val Gly Cys Thr Asp
            740                 745                 750

Leu Asn Glu Asp Leu Gly Val Trp Val Ile Phe Lys Ile Lys Thr Gln
        755                 760                 765

Asp Gly His Ala Lys Ile Gly Asn Leu Glu Phe Leu Lys Glu Lys Leu
    770                 775                 780

Leu Leu Gly Glu Ala Leu Ala Arg Val Lys Lys Ala Glu Lys Lys Trp
785                 790                 795                 800

Arg Asp Lys Arg Asp Lys Leu Glu Trp Glu Thr Asn Val Val Tyr Lys
                805                 810                 815

Glu Ala Lys Glu Ser Val Asp Ala Leu Phe Val Asp Ser Gln Tyr Ser
```

```
            820                 825                 830

Arg Leu Gln Ala Asp Thr Asn Ile Ala Met Ile His Ala Ala Asp Lys
        835                 840                 845

Arg Val His Arg Ile Arg Glu Ala Tyr Leu Pro Glu Leu Thr Val Ile
    850                 855                 860

Pro Gly Val Asn Ala Ser Ile Phe Glu Glu Leu Glu Gly Arg Ile Phe
865                 870                 875                 880

Thr Ala Tyr Ser Leu Tyr Gly Ala Arg Asn Val Ile Lys Asn Gly Asp
                885                 890                 895

Phe Asn Asn Gly Leu Ser Cys Trp Asn Val Lys Gly His Val Glu Val
            900                 905                 910

Gln Gln Ile His His Arg Ser Val Leu Val Val Pro Ser Trp Lys Thr
        915                 920                 925

Glu Val Ser Gln Glu Val Cys Val Cys Pro Gly Arg Gly Tyr Ile Leu
    930                 935                 940

Arg Val Thr Ala Tyr Lys Glu Gly Tyr Gly Glu Gly Asn Val Thr Ile
945                 950                 955                 960

His Glu Ile Glu Asn Asn Thr Asp Glu Leu Lys Phe Arg Asn Cys Glu
                965                 970                 975

Glu Glu Glu Val Tyr Pro Asn Asn Thr Val Thr Cys Asn Asp Tyr Thr
            980                 985                 990

Val Asn Gln Glu Glu Tyr Lys Gly  Thr Cys Thr Ser Arg  Asn Arg Gly
        995                 1000                1005

Tyr Asp  Glu Ser Tyr Glu Ser  Ser Ser Ser Glu Ser  Ala Tyr Tyr
    1010                 1015                 1020

Ala Ser  Val Tyr Glu Glu Lys  Gly Tyr Thr Asp Gly  Arg Arg Glu
    1025                 1030                 1035

Asn Leu  Cys Glu Phe Asn Arg  Gly Tyr Gly Asp Tyr  Thr Ser Leu
    1040                 1045                 1050

Pro Thr  Ala Tyr Val Thr Lys  Glu Leu Glu Tyr Phe  Pro Glu Thr
    1055                 1060                 1065

Asp Lys  Val Trp Ile Glu Ile  Gly Glu Thr Glu Gly  Ala Phe Ile
    1070                 1075                 1080

Leu Asp  Ser Val Glu Leu Leu  Leu Met Glu Glu
    1085                 1090


<210> SEQ ID NO 36
<211> LENGTH: 1169
<212> TYPE: PRT
<213> ORGANISM: Bacillus thuringiensis

<400> SEQUENCE: 36

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95
```

-continued

```
Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala Phe Asn Leu His Ser Gly Ala Thr Ile Val Lys Gly Pro
465                 470                 475                 480

Gly Phe Thr Gly Gly Asp Ile Leu Arg Arg Thr Asn Val Gly Ser Phe
                485                 490                 495

Gly Asp Met Arg Val Asn Ile Thr Ala Pro Leu Ser Gln Arg Tyr Arg
            500                 505                 510

Val Arg Ile Arg Tyr Ala Ser Thr Thr Asp Leu Gln Phe Tyr Thr Asn
```

```
        515                 520                 525

Ile Asn Gly Thr Thr Ile Asn Ile Gly Asn Phe Ser Ser Thr Met Asp
    530                 535                 540

Ser Gly Asp Asp Leu Gln Tyr Gly Arg Phe Arg Val Ala Gly Phe Thr
545                 550                 555                 560

Thr Pro Phe Thr Phe Ser Asp Ala Met Ser Thr Phe Thr Ile Gly Ala
                565                 570                 575

Phe Ser Phe Ser Ser Asn Asn Glu Val Tyr Ile Asp Arg Ile Glu Phe
            580                 585                 590

Val Pro Ala Glu Val Thr Phe Glu Ala Glu Tyr Asp Leu Glu Lys Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
            660                 665                 670

Gln Asp Pro Asn Phe Arg Gly Ile Asn Arg Gln Pro Asp Arg Gly Trp
        675                 680                 685

Arg Gly Ser Thr Asp Ile Thr Ile Gln Gly Gly Asp Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Gln Ser Pro Ile Gly Lys Cys Gly
    770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
    850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Glu Ala Lys Lys Ser Val
                885                 890                 895

Asp Ala Leu Phe Val Asn Ser Gln Tyr Asp Arg Leu Gln Ala Asp Thr
            900                 905                 910

Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
    930                 935                 940
```

```
Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                 1005

Val Arg  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  Asn Thr Asp Glu Leu  Lys Phe Ser Asn Cys  Val Glu Glu
    1040                 1045                 1050

Glu Ile  Tyr Pro Asn Asn Thr  Val Thr Cys Asn Asp  Tyr Thr Ala
    1055                 1060                 1065

Thr Gln  Glu Glu Tyr Glu Gly  Thr Tyr Thr Ser Arg  Asn Arg Gly
    1070                 1075                 1080

Tyr Asp  Gly Ala Tyr Glu Ser  Asn Ser Ser Val Pro  Ala Asp Tyr
    1085                 1090                 1095

Ala Ser  Ala Tyr Glu Glu Lys  Ala Tyr Thr Asp Gly  Arg Arg Asp
    1100                 1105                 1110

Asn Thr  Cys Glu Ser Asn Arg  Gly Tyr Gly Asp Tyr  Thr Pro Leu
    1115                 1120                 1125

Pro Ala  Gly Tyr Val Thr Lys  Glu Leu Glu Tyr Phe  Pro Glu Thr
    1130                 1135                 1140

Asp Lys  Val Trp Ile Glu Ile  Gly Glu Thr Glu Gly  Thr Phe Ile
    1145                 1150                 1155

Val Asp  Ser Val Glu Leu Leu  Leu Met Glu Glu
    1160                 1165


<210> SEQ ID NO 37
<211> LENGTH: 1138
<212> TYPE: PRT
<213> ORGANISM: Bacillus thuringiensis

<400> SEQUENCE: 37

Met Glu Val Asn His Gln Asn Glu Cys Val Pro Tyr Asn Cys Leu Lys
1               5                   10                  15

Asn Pro Lys Ile Glu Met Leu Asp Ile Glu Gly Ile Ser Ser Arg Ser
            20                  25                  30

Arg Glu Gln Val Ala Glu Ile Ser Leu Gly Leu Thr Arg Phe Leu Leu
        35                  40                  45

Glu Ser Leu Leu Pro Gly Ala Ser Phe Gly Phe Gly Leu Phe Asp Ile
    50                  55                  60

Ile Trp Gly Val Ile Gly Pro Asp Gln Trp Ser Leu Phe Leu Thr Gln
65                  70                  75                  80

Ile Glu Gln Leu Ile Asp Gln Arg Ile Glu Ala His Val Arg Asn Gln
                85                  90                  95

Ala Ile Ser Arg Leu Glu Gly Leu Gly Asp Ser Tyr Glu Val Tyr Ile
            100                 105                 110

Glu Ser Leu Arg Glu Trp Glu Ala Ser Pro Asn Asn Glu Ser Leu Gln
        115                 120                 125

Gln Asp Val Arg Asn Arg Phe Ser Asn Thr Asp Asn Ala Leu Ile Thr
```

-continued

```
    130                 135                 140

Ala Ile Pro Ile Leu Arg Glu Gln Gly Phe Glu Ile Pro Leu Leu Thr
145                 150                 155                 160

Val Tyr Val Gln Ala Ala Asn Leu His Leu Ser Leu Leu Arg Asp Ala
                165                 170                 175

Val Tyr Phe Gly Gln Arg Trp Gly Leu Asp Thr Ala Thr Val Asn Asn
            180                 185                 190

His Tyr Asn Arg Leu Ile Asn Leu Ile Asn Thr Tyr Ser Asp His Cys
        195                 200                 205

Ala Gln Trp Phe Asn Arg Gly Leu Asp Asn Phe Gly Val Val Thr Ala
    210                 215                 220

Arg Tyr Leu Asp Phe Gln Arg Glu Val Thr Ile Ser Val Leu Asp Ile
225                 230                 235                 240

Val Ala Leu Phe Pro Asn Tyr Asp Ile Arg Thr Tyr Pro Ile Gln Thr
                245                 250                 255

Leu Ser Gln Leu Thr Arg Glu Ile Tyr Thr Ser Pro Val Ala Glu Pro
            260                 265                 270

Gly Ala Ser Leu Asn Val Asp Leu Arg Asn Ile Leu Arg Glu Pro His
        275                 280                 285

Leu Met Asp Phe Leu Thr Arg Leu Val Ile Tyr Thr Gly Val Gln Gly
    290                 295                 300

Gly Ile Tyr His Trp Ala Gly His Glu Ile Ser Ser Arg Thr Thr Gly
305                 310                 315                 320

Asn Leu Ser Ser Asn Ile Gln Phe Pro Leu Tyr Gly Thr Ser Ala Asn
                325                 330                 335

Ala Asp Arg Pro Phe Asn Leu Ala Ile His Tyr Ser Glu Thr Ile Tyr
            340                 345                 350

Arg Thr Leu Ser Ala Pro Ile Tyr Ser Val Ser Gly Gly Ile Ser Pro
        355                 360                 365

Asn Arg Thr Arg Ala Val Glu Gly Val Arg Phe Leu Thr Ala Arg Asp
    370                 375                 380

Asn Asn Leu Asn Ser Leu Pro Phe Leu Tyr Arg Lys Glu Gly Ser Leu
385                 390                 395                 400

Asp Ser Phe Thr Glu Leu Pro Pro Glu Asp Glu Asn Glu Pro Pro Tyr
                405                 410                 415

Ile Gly Tyr Ser His Arg Leu Cys His Ala Arg Phe Ala Arg Ser Ser
            420                 425                 430

Val Val Leu Glu Pro Ser Asn Phe Ala Arg Ile Pro Val Phe Ser Trp
        435                 440                 445

Thr His Arg Ser Ala Gly Pro Thr Asn Glu Val Ser Ser Ser Arg Ile
    450                 455                 460

Thr Gln Ile Pro Trp Val Lys Ala His Thr Leu Asp Ser Gly Ala Phe
465                 470                 475                 480

Val Ile Lys Gly Pro Gly Phe Thr Gly Gly Asp Ile Leu Thr Arg Pro
                485                 490                 495

Asn Leu Gly Thr Leu Gly Ala Leu Arg Val Thr Leu Thr Gly Gln Leu
            500                 505                 510

Pro Gln Thr Tyr Asn Ile Arg Ile Arg Tyr Ala Ser Ile Ala Asn Arg
        515                 520                 525

Gly Gly Thr Leu Ile Phe Ser Gln Pro Pro Ser Tyr Gly Leu Thr Phe
    530                 535                 540

Pro Lys Thr Met Asp Ile Asp Glu Pro Leu Thr Ser Arg Ser Phe Ala
545                 550                 555                 560
```

-continued

```
Arg Thr Thr Leu Phe Thr Pro Ile Thr Phe Thr Gln Ala Gln Ala Glu
                565                 570                 575

Leu Asn Leu Thr Ile Gln Gln Gly Val Tyr Ile Asp Arg Ile Glu Phe
            580                 585                 590

Ile Pro Val Asn Ala Thr Phe Glu Ala Glu Tyr Asp Leu Glu Arg Ala
        595                 600                 605

Gln Lys Ala Val Asn Ala Leu Phe Thr Ser Ser Asn Gln Leu Gly Leu
    610                 615                 620

Lys Thr Asp Leu Thr Asp Tyr His Ile Asp Gln Val Ser Asn Leu Val
625                 630                 635                 640

Asp Cys Leu Ser Asp Glu Phe Cys Ile Asp Glu Lys Arg Glu Leu Ser
                645                 650                 655

Glu Lys Val Lys His Ala Lys Arg Leu Ser Asp Glu Arg Asn Leu Leu
            660                 665                 670

Gln Asp Ser Asn Phe Arg Gly Ile Asn Arg Gln Pro Asp Arg Gly Trp
        675                 680                 685

Arg Gly Ser Thr Asp Ile Thr Ile Gln Gly Gly Asn Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Gln Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Val Glu Ser Pro Ile Gly Lys Cys Gly
    770                 775                 780

Glu Pro Asn Arg Cys Val Pro Gln Leu Glu Trp Asn Ser Asn Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu His Asp Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
    850                 855                 860

Ala Arg Val Lys Arg Ala Glu Lys Lys Trp Arg Asp Lys Arg Glu Thr
865                 870                 875                 880

Leu Gln Leu Glu Thr Asn Ile Val Tyr Lys Glu Ala Lys Glu Ser Val
                885                 890                 895

Asp Ala Leu Phe Ala Asn Ser Gln Tyr Asn Arg Leu Gln Ala Asp Thr
            900                 905                 910

Asn Ile Ala Met Ile His Ala Ala Asp Lys Arg Val His Arg Ile Arg
        915                 920                 925

Glu Ala Tyr Leu Pro Glu Leu Ser Val Ile Pro Gly Val Asn Ala Gly
    930                 935                 940

Ile Phe Glu Glu Leu Glu Gly Arg Ile Phe Thr Ala Phe Ser Leu Tyr
945                 950                 955                 960

Asp Ala Arg Asn Val Ile Lys Asn Ser Asp Phe Asn Asn Gly Leu Ser
                965                 970                 975
```

-continued

```
Cys Trp Asn Val Lys Gly His Val Asp Ile Glu Glu Gln Asn Asn His
            980                 985                 990

Arg Ser Val Leu Val Val Pro Glu  Trp Glu Ala Glu Val  Ser Gln Lys
        995                 1000                 1005

Val His  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  His Thr Asp Glu Leu  Lys Phe Arg Asn Cys  Glu Glu Asp
    1040                 1045                 1050

Glu Val  Tyr Pro Asn Asn Thr  Arg Thr Cys Asn Ala  Tyr Pro Ala
    1055                 1060                 1065

Asp Gln  Glu Gly Tyr Glu Gly  Ala Cys Thr Ser Arg  Asn Arg Gly
    1070                 1075                 1080

Tyr Asp  Glu Val Tyr Gly Asn  Thr Pro Ser Leu Pro  Ala Asp Tyr
    1085                 1090                 1095

Ala Pro  Ile Tyr Glu Glu Asn  Ala Tyr Thr Asp Gly  Arg Arg Gly
    1100                 1105                 1110

Asn Pro  Cys Glu Ser Ser Arg  Gly Tyr Gly Asp Tyr  Thr Pro Leu
    1115                 1120                 1125

Pro Ala  Gly Tyr Glu Thr Lys  Glu Leu Glu
    1130                 1135


<210> SEQ ID NO 38
<211> LENGTH: 719
<212> TYPE: PRT
<213> ORGANISM: Bacillus thuringiensis

<400> SEQUENCE: 38

Met Lys Leu Lys Asn Pro Asp Lys His Gln Ser Leu Ser Ser Asn Ala
1               5                   10                  15

Lys Val Asp Lys Ile Ala Thr Asp Ser Leu Lys Asn Glu Thr Asp Ile
            20                  25                  30

Glu Leu Lys Asn Met Asn Asn Glu Asp Tyr Leu Arg Met Ser Glu His
        35                  40                  45

Glu Ser Ile Asp Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Ile Ala Ser Leu Tyr Ser Phe Ile Leu Gly Glu Leu Trp Pro Lys
                85                  90                  95

Gly Lys Ser Gln Trp Glu Ile Phe Met Glu His Val Glu Glu Ile Ile
            100                 105                 110

Asn Gln Lys Ile Leu Thr Tyr Ala Arg Asn Lys Ala Leu Ser Asp Leu
        115                 120                 125

Arg Gly Leu Gly Asp Ala Leu Ala Val Tyr His Glu Ser Leu Glu Ser
    130                 135                 140

Trp Val Lys Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205
```

-continued

```
Glu Trp Gly Leu Ser Ala Ser Glu Ile Ser Thr Phe Tyr Asn Arg Gln
    210                 215                 220

Val Glu Arg Thr Arg Asp Tyr Ser Asp His Cys Val Lys Trp Tyr Asn
225                 230                 235                 240

Thr Gly Leu Asn Asn Leu Arg Gly Thr Asn Ala Lys Ser Trp Val Arg
                245                 250                 255

Tyr Asn Gln Phe Arg Lys Asp Met Thr Leu Met Val Leu Asp Leu Val
            260                 265                 270

Ala Leu Phe Pro Ser Tyr Asp Thr Leu Val Tyr Pro Ile Lys Thr Thr
        275                 280                 285

Ser Gln Leu Thr Arg Glu Val Tyr Thr Asp Ala Ile Gly Thr Val His
    290                 295                 300

Pro Ser Gly Ala Val Ala Ser Thr Thr Trp Tyr Asn Asn Asn Ala Pro
305                 310                 315                 320

Ser Phe Ser Thr Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Thr Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Asn Ser Asp Ser Ile Thr Gln Ile Pro Leu
            500                 505                 510

Val Lys Ala Phe Asn Leu Pro Ser Gly Ala Ser Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Leu Arg Ile Arg Tyr Ala Ser Thr Thr Asn Leu Glu Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Ala Phe Arg Thr Val Gly Phe Thr
        595                 600                 605

Thr Pro Phe Ser Phe Ser Asn Ala Gln Ser Thr Phe Thr Ile Gly Ala
    610                 615                 620
```

-continued

Trp Asn Phe Ser Leu Gly Asn Glu Val Tyr Ile Asp Arg Ile Glu Phe
625 630 635 640

Val Pro Val Glu Val Thr Tyr Glu Ala Glu His Asp Phe Glu Lys Ala
645 650 655

Gln Glu Glu Val Thr Ala Leu Phe Thr Ser Thr Asn Pro Gly Gly Leu
660 665 670

Lys Thr Asn Val Thr Glu Tyr His Ile Asp Gln Val Ser Asn Leu Val
675 680 685

Glu Ser Leu Ser Asn Glu Phe Tyr Leu Asp Glu Lys Arg Glu Leu Phe
690 695 700

Glu Ile Val Lys Tyr Ala Lys Gln Leu His Ile Gly Arg Asn Met
705 710 715

<210> SEQ ID NO 39
<211> LENGTH: 1164
<212> TYPE: PRT
<213> ORGANISM: Bacillus thuringiensis

<400> SEQUENCE: 39

Met Glu Arg Asn Asn Gln Asp Gln Cys Ile Pro Tyr Asn Cys Leu Asn
1 5 10 15

Asn Pro Glu Val Gly Ile Leu Asp Ile Glu Asn Phe Asn Leu Glu Leu
20 25 30

Val Ser Gln Val Ser Val Gly Leu Thr Arg Phe Leu Leu Glu Ala Ser
35 40 45

Ile Pro Gly Ala Gly Phe Ala Leu Gly Leu Phe Asp Ile Ile Trp Gly
50 55 60

Ala Leu Gly Val Asp Gln Trp Ser Leu Phe Leu Ala Gln Ile Glu Gln
65 70 75 80

Leu Ile Asn Glu Arg Ile Thr Thr Val Glu Arg Asn Arg Ala Ile Gln
85 90 95

Ala Leu Ser Gly Leu Ser Ser Ser Tyr Glu Val Tyr Ile Glu Ala Leu
100 105 110

Arg Glu Trp Glu Asn Asp Leu Asp Asn Pro Ala Ser Arg Asp Arg Val
115 120 125

Val Ala Arg Phe Arg Ala Thr Asp Asn Ser Leu Ile Thr Asp Ile Pro
130 135 140

Leu Leu Glu Ile Pro Gly Phe Glu Ile Ala Thr Leu Ser Val Tyr Thr
145 150 155 160

Gln Ala Ala Asn Leu His Leu Ala Leu Leu Arg Asp Ala Val Tyr Phe
165 170 175

Gly Glu Arg Trp Gly Leu Thr Gln Thr Asn Ile Glu Asp Leu His Thr
180 185 190

Arg Leu Thr Arg Tyr Ile Gln Glu Tyr Ser Asp His Cys Ala Arg Trp
195 200 205

Tyr Asn Gln Gly Leu Asn Asn Ile Gly Gly Ile Asn Thr Arg Tyr Leu
210 215 220

Asp Phe Gln Arg Glu Leu Thr Ile Ser Val Leu Asp Ile Val Ala Leu
225 230 235 240

Phe Pro Asn Tyr Asp Ile Arg Thr Tyr Pro Ile Pro Thr Gln Ser Gln
245 250 255

Leu Thr Arg Glu Ile Tyr Thr Ser Pro Val Val Ala Pro Gly Val Asn
260 265 270

Trp Ile Leu Ser Ile Ser Asn Val Leu Arg Ala Pro His Leu Met Asp
275 280 285

```
Phe Phe Asp Arg Ile Ile Ile Tyr Thr Gly Thr Val Arg Ser Thr Pro
    290                 295                 300

His Trp Glu Gly His Glu Val Ile Ser Arg Arg Thr Gly Gln Gly Asn
305                 310                 315                 320

Glu Ile Arg Ser Pro Leu Tyr Gly Val Ala Ala Asn Ala Glu Pro Pro
                325                 330                 335

Val Thr Ile Arg Pro Thr Gly Phe Thr Asp Glu Gln Arg Gln Val Tyr
            340                 345                 350

Arg Val Leu Ser Arg Val Ala Ser Phe Arg Asn Ser Gly Thr Asn Phe
        355                 360                 365

Ser Leu Val Asp Ala Ala Ser Phe Leu Thr Ile Phe Ser Ala Ser Ser
    370                 375                 380

Ile Tyr Arg Asn Gly Phe Gly Phe Asn Ala Asp Thr Ile Asp Glu Ile
385                 390                 395                 400

Pro Ile Glu Gly Thr Asp Pro Tyr Ile Gly Tyr Ser His Arg Leu Cys
                405                 410                 415

His Val Gly Phe Thr Ala Ser Ser Pro Phe Ile Ser Gln Tyr Ala Arg
            420                 425                 430

Ala Pro Val Phe Ser Trp Thr His Arg Ser Ala Thr Phe Thr Asn Thr
        435                 440                 445

Ile Asp Pro Glu Arg Ile Thr Gln Ile Pro Met Val Lys Ala Tyr Asn
    450                 455                 460

Leu His Ala Gly Ala Thr Val Val Arg Gly Pro Gly Phe Thr Gly Gly
465                 470                 475                 480

Asp Leu Leu Arg Arg Thr Asn Thr Gly Thr Phe Ala Asp Ile Arg Val
                485                 490                 495

Asn Ile Thr Gly Pro Leu Ser Gln Arg Tyr Arg Val Arg Ile Arg Tyr
            500                 505                 510

Ala Ser Thr Thr Asp Leu Gln Phe Phe Thr Arg Ile Asn Gly Thr Ser
        515                 520                 525

Val Asn Gln Gly Asn Phe Gln Arg Thr Met Asn Arg Gly Asp Asn Leu
    530                 535                 540

Glu Ser Gly Asn Phe Arg Thr Ala Gly Phe Ser Thr Pro Phe Ser Phe
545                 550                 555                 560

Ser Asn Ala Gln Ser Thr Phe Thr Leu Gly Thr Gln Ala Phe Ser Asn
                565                 570                 575

Gln Glu Val Tyr Ile Asp Arg Ile Glu Phe Val Pro Ala Glu Val Thr
            580                 585                 590

Phe Glu Ala Glu Ser Asp Leu Glu Arg Ala Gln Lys Ala Val Asn Ala
        595                 600                 605

Leu Phe Thr Ser Thr Ser Gln Leu Gly Leu Lys Thr Asn Val Thr Gly
    610                 615                 620

Tyr His Ile Asp Gln Val Ser Asn Leu Val Ala Cys Leu Ser Asp Glu
625                 630                 635                 640

Phe Cys Leu Asp Glu Lys Arg Glu Leu Ser Glu Lys Val Lys His Ala
                645                 650                 655

Lys Arg Leu Ser Asp Lys Arg Asn Leu Leu Gln Asp Pro Asn Phe Arg
            660                 665                 670

Gly Ile Asn Arg Gln Pro Asp His Gly Trp Arg Gly Ser Thr Asp Ile
        675                 680                 685

Thr Ile Gln Gly Gly Asp Asp Val Phe Lys Glu Asn Tyr Val Thr Leu
    690                 695                 700
```

```
Pro Gly Thr Phe Asp Glu Cys Tyr Pro Thr Tyr Leu Tyr Gln Lys Ile
705                 710                 715                 720

Asp Glu Ser Lys Leu Lys Ala Tyr Thr Arg Tyr Gln Leu Arg Gly Tyr
                725                 730                 735

Ile Glu Asp Ser Gln Asp Leu Glu Ile Tyr Leu Ile Arg Tyr Asn Ser
            740                 745                 750

Lys His Glu Ile Val Asn Val Pro Gly Thr Gly Ser Leu Trp Pro Leu
        755                 760                 765

Ser Val Glu Asn Gln Ile Gly Pro Cys Gly Glu Pro Asn Arg Cys Ala
    770                 775                 780

Pro His Leu Glu Trp Asn Pro Asp Leu His Cys Ser Cys Arg Asp Gly
785                 790                 795                 800

Glu Lys Cys Val His His Ser His His Phe Ser Leu Asp Ile Asp Val
                805                 810                 815

Gly Cys Thr Asp Leu Asn Glu Asp Leu Gly Val Trp Leu Ile Phe Lys
            820                 825                 830

Ile Lys Thr Gln Asp Gly His Ala Arg Leu Gly Asn Leu Glu Phe Leu
        835                 840                 845

Glu Glu Glu Pro Leu Leu Gly Glu Ala Leu Ala Arg Val Lys Arg Ala
    850                 855                 860

Glu Lys Lys Trp Arg Asp Lys Arg Glu Lys Leu Gln Leu Glu Thr Asn
865                 870                 875                 880

Ile Val Tyr Lys Glu Ala Lys Glu Ser Val Asp Ala Leu Phe Val Asn
                885                 890                 895

Ser Gln Tyr Asp Arg Leu Gln Ala Asp Thr Asn Ile Ala Met Ile His
            900                 905                 910

Ala Ala Asp Lys Arg Val His Arg Ile Arg Glu Ala Tyr Leu Pro Glu
        915                 920                 925

Leu Ser Val Ile Pro Gly Val Asn Ala Ala Ile Phe Glu Glu Leu Glu
    930                 935                 940

Gly Arg Ile Phe Thr Ala Tyr Ser Leu Tyr Asp Ala Arg Asn Val Ile
945                 950                 955                 960

Lys Asn Gly Asn Phe Asn Asn Gly Leu Leu Cys Trp Asn Val Lys Gly
                965                 970                 975

His Val Asp Val Glu Glu Gln Asn Asn His Arg Ser Val Leu Val Ile
            980                 985                 990

Pro Glu Trp Glu Ala Glu Val Ser  Gln Lys Val Arg Val  Cys Pro Gly
        995                 1000                 1005

Arg Gly  Tyr Ile Leu Arg Val  Thr Ala Tyr Lys Glu  Gly Tyr Gly
    1010                 1015                 1020

Glu Gly  Cys Val Thr Ile His  Glu Ile Glu Asp Asn  Thr Asp Glu
    1025                 1030                 1035

Leu Lys  Phe Ser Asn Cys Val  Glu Glu Gly Tyr Pro  Asn Asn Thr
    1040                 1045                 1050

Val Thr  Cys Asn Glu Tyr Thr  Met Asn Gln Gly Val  Gly Glu Cys
    1055                 1060                 1065

Thr Asp  Ala Cys Asn Val Arg  Asn Arg Gly Tyr Glu  Asp Ala Tyr
    1070                 1075                 1080

Gly His  Asn Pro Ser Thr Pro  Val His Tyr Thr Thr  Pro Tyr Glu
    1085                 1090                 1095

Glu Glu  Thr Tyr Thr Asp Glu  Arg Arg Glu Asn Pro  Cys Glu Ala
    1100                 1105                 1110

Asn Lys  Gly Tyr Val Asn Tyr  Thr Pro Leu Pro Val  Gly Tyr Val
```

```
    1115                1120                1125

Thr Lys  Glu Leu Glu Tyr Phe  Pro Glu Thr Asp Thr  Val Trp Ile
    1130                1135                1140

Glu Ile  Gly Glu Thr Glu Gly  Thr Phe Ile Val Asp  Ser Val Glu
    1145                1150                1155

Leu Leu  Leu Met Glu Glu
    1160


<210> SEQ ID NO 40
<211> LENGTH: 1166
<212> TYPE: PRT
<213> ORGANISM: Bacillus thuringiensis

<400> SEQUENCE: 40

Met Lys Ile Asn Asn Gln Asn Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Met Ser Leu Leu Gln Phe Leu Leu Asn Asn
        35                  40                  45

Phe Val Pro Gly Gly Gly Val Ile Ser Gly Leu Ile Asn Lys Ile Trp
    50                  55                  60

Gly Ala Leu Arg Pro Ser Glu Trp Glu Leu Phe Leu Ala Gln Ile Glu
65                  70                  75                  80

Gln Leu Ile Asp Arg Arg Ile Glu Ala Ala Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Ser Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Lys Arg Ile Asp Glu Tyr Ser Asp His Cys Val Asp
        195                 200                 205

Thr Tyr Lys Thr Glu Leu Glu Arg Leu Glu Phe Ser Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Gly Arg Leu Tyr Pro Ile
                245                 250                 255

Arg Thr Ile Ser Gln Leu Thr Arg Asp Ile Tyr Thr Ser Pro Val Ser
            260                 265                 270

Glu Phe Tyr Tyr Gly Pro Ile Tyr Asn Tyr Asn Ile Val Gly Arg Leu
        275                 280                 285

Thr Glu Gln Gln Leu Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320
```

```
Leu Glu Met Lys Ala Thr Asp Thr Ser Gly Asn Gln Val Ser Phe Pro
                325                 330                 335

Leu Ala Gly Thr Arg Gly Asn Ser Ala Pro Pro Val Thr Val Arg Asn
            340                 345                 350

Asn Gly Glu Gly Val Tyr Arg Ile Leu Ser Glu Pro Phe Tyr Ser Ser
        355                 360                 365

Pro Phe Leu Gly Thr Ser Val Leu Gly Ser Arg Gly Glu Glu Phe Ala
    370                 375                 380

Phe Ala Ser Asn Thr Thr Thr Ser Leu Pro Ser Thr Ile Tyr Arg Asn
385                 390                 395                 400

Arg Gly Thr Val Asp Ser Leu Val Ser Ile Pro Pro Gln Asp Tyr Ser
                405                 410                 415

Val Pro Pro His Arg Gly Tyr Ser His Leu Leu Ser His Val Thr Met
            420                 425                 430

His Asn Ser Ser Pro Ile Phe His Trp Thr His Arg Ser Ala Thr Pro
        435                 440                 445

Arg Asn Thr Ile Asp Pro Asp Ser Ile Thr Gln Ile Pro Val Val Lys
    450                 455                 460

Ala Ser His Leu Ser Gly Gly Ser Val Ile Lys Gly Pro Gly His Thr
465                 470                 475                 480

Gly Gly Asp Leu Ile Ser Leu Pro Val Asn Asn Phe Thr His Phe Arg
                485                 490                 495

Ile Pro Phe Gln Ala Asn Thr Pro Gln Arg Tyr Arg Ile Arg Ile Arg
            500                 505                 510

Tyr Ala Ala Asp Ser Asp Gly Thr Leu Asp Ser Gly Val Phe Leu Ser
        515                 520                 525

Ala Ala Ala Gly Asp Gly Phe Asn Thr Thr Ser Tyr Arg Ala Thr Met
    530                 535                 540

Ser Pro Gly Gly Ser Leu Thr Ser Arg Asp Phe Gln Phe Leu Asp Leu
545                 550                 555                 560

Asn Thr Ser Phe Thr Ser Asp Val Ala Ser Asn Leu Trp Leu His Phe
                565                 570                 575

Ile Arg Tyr Ile Arg Pro Gly Asn Leu Tyr Ile Asp Arg Ala Glu Phe
            580                 585                 590

Ile Pro Val Asp Ala Thr Phe Glu Ala Gly Tyr Asn Leu Glu Arg Ala
        595                 600                 605

Gln Lys Ala Val Asn Ala Leu Phe Thr Ser Thr Asn Gln Lys Gly Leu
    610                 615                 620

Gln Thr Asp Val Thr Asp Tyr His Ile Asp Gln Val Ser Asn Leu Val
625                 630                 635                 640

Asp Cys Leu Ser Asp Glu Phe Cys Leu Asp Glu Lys Arg Glu Leu Ser
                645                 650                 655

Glu Lys Val Lys Gln Ala Lys Arg Leu Ser Asp Glu Arg Asn Leu Leu
            660                 665                 670

Gln Asp Ser Asn Phe Arg Gly Ile Asn Arg Glu Gln Asp Arg Gly Trp
        675                 680                 685

Arg Gly Ser Thr His Ile Thr Ile Gln Gly Gly Asn Asp Val Phe Lys
    690                 695                 700

Glu Asn Phe Val Thr Leu Pro Gly Ala Phe Asp Ala Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Asp Ile Tyr
```

```
            740                 745                 750

Leu Ile Arg Tyr Asn Thr Lys His Glu Thr Leu Asn Val Pro Gly Thr
        755                 760                 765

Lys Ser Pro Trp Ser Leu Cys Thr Glu Ser Pro Leu Gly Lys Cys Gly
    770                 775                 780

Glu Pro Asn Arg Cys Ala Ser Gln Ile Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asn Leu Gly
            820                 825                 830

Ile Trp Val Ile Phe Lys Ile Lys Thr Gln Asp Gly His Ala Arg Leu
        835                 840                 845

Gly Asn Leu Glu Phe Leu Glu Glu Lys Pro Leu Leu Gly Glu Ala Leu
    850                 855                 860

Ala Arg Val Lys Arg Ala Glu Lys Lys Trp Arg Asp Lys Arg Glu Lys
865                 870                 875                 880

Leu Gln Ser Glu Thr Asn Ile Val Tyr Lys Glu Ala Lys Glu Ala Val
                885                 890                 895

Asp Gly Leu Phe Val Asp Ser Gln Tyr Glu Arg Leu Gln Ala Asp Thr
            900                 905                 910

Asn Ile Ala Met Ile His Ala Ala Asp Lys His Val His Gln Ile Arg
        915                 920                 925

Glu Val Tyr Phe Pro Glu Leu Ser Val Ile Pro Gly Val Asn Ala Ala
    930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Val Gln Asn Asn His
            980                 985                 990

Arg Ser Val Leu Val Ile Ala Glu  Trp Glu Ala Glu Val  Ser Gln Glu
        995                 1000                1005

Val Pro  Val Cys Pro Gly Arg  Gly Tyr Ile Leu Arg  Val Thr Ala
    1010                1015                1020

Tyr Lys  Glu Gly Tyr Gly Glu  Gly Cys Val Thr Ile  His Glu Ile
    1025                1030                1035

Glu Asp  His Thr Asp Glu Leu  Lys Phe Arg Asn Cys  Glu Glu Glu
    1040                1045                1050

Glu Val  Tyr Pro Asn Asn Thr  Val Thr Cys Asn Gly  Tyr Thr Ala
    1055                1060                1065

Thr Gln  Glu Glu Tyr Lys Asp  Ala Tyr Thr Ser Arg  Asn Arg Gly
    1070                1075                1080

Tyr Asp  Glu Ala Tyr Gly Asn  Asn Pro Ser Val Pro  Ala Asp Tyr
    1085                1090                1095

Ala Ser  Val Tyr Glu Glu Lys  Ala Tyr Thr Asp Gly  Arg Arg Glu
    1100                1105                1110

Asn Pro  Cys Glu Met Glu Arg  Gly Tyr Thr Pro Leu  Pro Val Gly
    1115                1120                1125

Tyr Ile  Thr Lys Glu Leu Glu  Tyr Phe Pro Glu Thr  Asp Thr Val
    1130                1135                1140

Trp Ile  Glu Ile Gly Glu Thr  Glu Gly Thr Phe Ile  Ile Asp Ser
    1145                1150                1155
```

```
Val Glu  Leu Leu Leu Met Glu  Glu
    1160                1165


<210> SEQ ID NO 41
<211> LENGTH: 1181
<212> TYPE: PRT
<213> ORGANISM: Artificial Sequence
<220> FEATURE:
<223> OTHER INFORMATION: Mutant BT-0001 protein

<400> SEQUENCE: 41

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350
```

```
Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Val Tyr Leu Ile Arg Tyr
        755                 760                 765
```

```
Asn Ala Lys His Glu Thr Leu Asn Val Pro Gly Thr Gly Ser Leu Trp
    770                 775                 780

Pro Leu Ala Val Lys Ser Pro Ile Gly Arg Cys Gly Glu Pro Asn Arg
785                 790                 795                 800

Cys Ala Pro Arg Ile Glu Trp Lys Pro Asp Val Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Lys Ile Gly Asn Leu Glu
    850                 855                 860

Phe Leu Glu Glu Lys Leu Leu Leu Gly Glu Ala Leu Ala Arg Val Lys
865                 870                 875                 880

Lys Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asp Ser Gln Tyr Asn Arg Leu Gln Thr Asp Thr Asn Ile Ala Met
        915                 920                 925

Ile His Ala Ala Asp Lys Arg Val His Arg Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Leu Ile Phe Thr Ala Phe Ser Leu Tyr Asp Ala Arg Asn
                965                 970                 975

Val Ile Lys Asn Gly Asp Phe Asn Tyr Gly Leu Ser Cys Trp Asn Val
            980                 985                 990

Lys Gly His Val Asp Val Glu Glu  Gln Asn Asn His Arg  Ser Val Leu
        995                 1000                1005

Val Ile  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035

Gly Tyr  Gly Glu Gly Cys Val  Thr Ile His Glu Ile  Glu Asp Asn
    1040                1045                1050

Thr Asp  Glu Leu Lys Phe Ser  Asn Cys Val Glu Glu  Glu Val Tyr
    1055                1060                1065

Pro Asn  Asn Thr Val Thr Cys  Asn Asp Tyr Thr Ala  Thr Gln Glu
    1070                1075                1080

Glu Tyr  Glu Gly Thr Tyr Thr  Ser Arg Asn Arg Gly  Tyr Asp Gly
    1085                1090                1095

Ala Tyr  Glu Ser Asn Ser Ser  Val Pro Ala Asp Tyr  Ala Ser Ala
    1100                1105                1110

Tyr Glu  Glu Lys Ala Tyr Thr  Asp Gly Arg Arg Asp  Asn Pro Cys
    1115                1120                1125

Glu Ser  Asn Arg Gly Tyr Arg  Asp Tyr Thr Pro Leu  Pro Ala Gly
    1130                1135                1140

Tyr Val  Thr Lys Glu Leu Glu  Tyr Phe Pro Glu Thr  Asp Lys Val
    1145                1150                1155

Trp Ile  Glu Leu Gly Glu Thr  Glu Gly Thr Phe Leu  Val Asp Ser
    1160                1165                1170

Val Glu  Leu Leu Leu Met Glu  Glu
```

1175 1180

<210> SEQ ID NO 42
<211> LENGTH: 1176
<212> TYPE: PRT
<213> ORGANISM: Artificial Sequence
<220> FEATURE:
<223> OTHER INFORMATION: Mutant BT-0003 protein

<400> SEQUENCE: 42

Met Glu Ile Val Asn Asn Gln Asn Gln Cys Val Pro Tyr Asn Cys Leu
1 5 10 15

Asn Asn Pro Glu Ile Glu Ile Leu Glu Gly Gly Arg Ile Ser Val Gly
20 25 30

Asn Thr Pro Ile Asp Ile Ser Leu Ser Leu Thr Gln Phe Leu Leu Ser
35 40 45

Glu Phe Val Pro Gly Ala Gly Phe Val Leu Gly Leu Ile Asp Leu Ile
50 55 60

Trp Gly Phe Val Gly Pro Ser Gln Trp Asp Ala Phe Leu Ala Gln Val
65 70 75 80

Glu Gln Leu Ile Asn Gln Arg Ile Ala Glu Ala Val Arg Asn Thr Ala
85 90 95

Ile Gln Glu Leu Glu Gly Met Ala Arg Val Tyr Arg Thr Tyr Ala Thr
100 105 110

Ala Phe Ala Glu Trp Glu Lys Ala Pro Asp Asp Pro Glu Leu Arg Glu
115 120 125

Ala Leu Arg Thr Gln Phe Thr Ala Thr Glu Thr Tyr Ile Ser Gly Arg
130 135 140

Ile Ser Val Leu Lys Ile Gln Thr Phe Glu Val Gln Leu Leu Ser Val
145 150 155 160

Phe Ala Gln Ala Ala Asn Leu His Leu Ser Leu Leu Arg Asp Val Val
165 170 175

Phe Phe Gly Gln Arg Trp Gly Phe Ser Thr Thr Thr Val Asn Asn Tyr
180 185 190

Tyr Asn Asp Leu Thr Glu Gly Ile Ser Thr Tyr Thr Asp Tyr Ala Val
195 200 205

Arg Trp Tyr Asn Thr Gly Leu Glu Arg Val Trp Gly Pro Asp Ser Arg
210 215 220

Asp Trp Val Arg Tyr Asn Gln Phe Arg Arg Glu Leu Thr Leu Thr Val
225 230 235 240

Leu Asp Ile Val Ala Leu Phe Ser Asn Tyr Asp Ser Arg Arg Tyr Pro
245 250 255

Ile Arg Thr Val Ser Gln Leu Thr Arg Glu Ile Tyr Thr Asn Pro Val
260 265 270

Leu Glu Asn Phe Asp Gly Ser Phe Arg Gly Met Ala Gln Arg Ile Glu
275 280 285

Gln Asn Ile Arg Gln Pro His Leu Met Asp Ile Leu Asn Ser Ile Thr
290 295 300

Ile Tyr Thr Asp Val His Arg Gly Phe Asn Tyr Trp Ser Gly His Gln
305 310 315 320

Ile Thr Ala Ser Pro Val Gly Phe Ser Gly Pro Glu Phe Ala Phe Pro
325 330 335

Leu Phe Gly Asn Ala Gly Asn Ala Ala Pro Pro Val Leu Val Ser Leu
340 345 350

Thr Gly Leu Gly Ile Phe Arg Thr Leu Ser Ser Pro Leu Tyr Arg Arg

```
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780
```

```
Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
    850                 855                 860

Leu Glu Glu Lys Pro Leu Val Gly Glu Ala Leu Ala Arg Val Lys Ile
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln  Asn Asn Gln Arg Ser  Val Leu Val
        995                 1000                1005

Val Pro  Glu Trp Glu Ala Glu  Val Ser Gln Glu Val  Arg Val Cys
    1010                 1015                 1020

Pro Gly  Arg Gly Tyr Ile Leu  Arg Val Thr Ala Tyr  Lys Glu Gly
    1025                 1030                 1035

Tyr Gly  Glu Gly Cys Val Thr  Ile His Glu Ile Glu  Asn Asn Thr
    1040                 1045                 1050

Asp Glu  Leu Lys Phe Ser Asn  Cys Val Glu Glu Glu  Ile Tyr Ser
    1055                 1060                 1065

Asn Asn  Thr Val Thr Cys Asn  Asp Tyr Thr Val Asn  Gln Glu Glu
    1070                 1075                 1080

Tyr Gly  Gly Ala Tyr Thr Ser  Arg Asn Arg Gly Tyr  Asn Glu Ala
    1085                 1090                 1095

Pro Ser  Val Pro Ala Asp Tyr  Ala Ser Val Tyr Glu  Glu Lys Ser
    1100                 1105                 1110

Tyr Thr  Asp Gly Arg Arg Glu  Asn Pro Cys Glu Phe  Asn Arg Gly
    1115                 1120                 1125

Tyr Arg  Asp Tyr Thr Pro Leu  Pro Val Gly Tyr Val  Thr Lys Glu
    1130                 1135                 1140

Leu Glu  Tyr Phe Pro Glu Thr  Asp Lys Val Trp Leu  Glu Ile Gly
    1145                 1150                 1155

Glu Thr  Glu Gly Thr Phe Ile  Val Asp Ser Leu Glu  Leu Leu Leu
    1160                 1165                 1170

Met Glu  Glu
    1175
```

<210> SEQ ID NO 43
<211> LENGTH: 1237
<212> TYPE: PRT
<213> ORGANISM: Artificial Sequence
<220> FEATURE:
<223> OTHER INFORMATION: Mutant BT-0020 protein

<400> SEQUENCE: 43

Met Asn Ser Asn Arg Lys Asn Glu Asn Glu Ile Ile Asp Ala Ser Phe
1 5 10 15

Ile Pro Ala Val Ser Asn Glu Ser Val Thr Ile Ser Lys Glu Tyr Ala
20 25 30

Gln Thr Asn Gln Leu Gln Asn Asn Ser Ile Glu Asp Gly Leu Cys Ile
35 40 45

Ala Glu Gly Glu Tyr Ile Asp Pro Phe Val Ser Ala Ser Thr Val Gln
50 55 60

Thr Gly Ile Ser Ile Ala Gly Arg Ile Leu Gly Val Leu Gly Val Pro
65 70 75 80

Phe Ala Gly Gln Leu Ala Ser Phe Tyr Ser Phe Ile Val Gly Glu Leu
85 90 95

Trp Pro Lys Gly Arg Asp Gln Trp Glu Ile Phe Met Glu His Val Glu
100 105 110

Gln Leu Val Arg Gln Gln Ile Thr Ala Asn Ala Arg Asn Thr Ala Leu
115 120 125

Ala Arg Leu Gln Gly Leu Gly Asn Ser Phe Arg Ala Tyr Gln Gln Ser
130 135 140

Leu Glu Asp Trp Leu Glu Asn Arg Asn Asp Ala Arg Thr Arg Ser Val
145 150 155 160

Leu Tyr Thr Gln Tyr Ile Ala Leu Glu Leu Asp Phe Leu Asn Ala Met
165 170 175

Pro Leu Phe Ala Ile Arg Glu Gln Glu Val Pro Leu Leu Met Val Tyr
180 185 190

Ala Gln Ala Ala Asn Leu His Leu Leu Leu Leu Arg Asp Ala Ser Leu
195 200 205

Tyr Gly Arg Glu Phe Gly Leu Thr Ser Gln Glu Ile Gln Arg Tyr Tyr
210 215 220

Glu Arg Gln Val Glu Arg Thr Arg Asp Tyr Ser Asp His Cys Val Gln
225 230 235 240

Trp Tyr Asn Thr Gly Leu Asn Asn Leu Arg Gly Thr Asn Ala Glu Ser
245 250 255

Trp Val Arg Tyr Asn Gln Phe Arg Arg Asp Leu Thr Leu Gly Val Leu
260 265 270

Asp Leu Val Ala Leu Phe Pro Ser Tyr Asp Thr Arg Thr Tyr Pro Ile
275 280 285

Asn Thr Ser Ala Gln Leu Thr Arg Glu Val Tyr Thr Asp Ala Ile Gly
290 295 300

Ala Thr Gly Val Asn Met Ala Ser Met Asn Trp Tyr Asn Asn Asn Ala
305 310 315 320

Pro Ser Phe Ser Ala Ile Glu Thr Ala Val Ile Arg Ser Pro His Leu
325 330 335

Leu Asp Phe Leu Glu Gln Leu Lys Ile Phe Ser Ala Ser Ser Arg Trp
340 345 350

Ser Asn Thr Arg His Met Thr Tyr Trp Arg Gly His Thr Ile Gln Ser
355 360 365

-continued

```
Arg Pro Ile Arg Gly Ala Leu Ile Thr Ser Thr His Gly Asn Thr Asn
    370                 375                 380

Thr Ser Ile Asn Pro Val Thr Phe Gln Phe Pro Ser Arg Asp Val Tyr
385                 390                 395                 400

Arg Thr Glu Ser Tyr Ala Gly Val Leu Leu Trp Gly Ile Tyr Leu Glu
                405                 410                 415

Pro Ile His Gly Val Pro Thr Val Arg Phe Asn Phe Arg Asn Pro Gln
            420                 425                 430

Asn Thr Phe Glu Arg Gly Thr Ala Asn Tyr Ser Gln Pro Tyr Glu Ser
        435                 440                 445

Pro Gly Leu Gln Leu Lys Asp Ser Glu Thr Glu Leu Pro Pro Glu Thr
    450                 455                 460

Thr Glu Arg Pro Asn Tyr Glu Ser Tyr Ser His Arg Leu Ser His Ile
465                 470                 475                 480

Gly Ile Ile Leu Gln Thr Arg Leu Asn Val Pro Val Tyr Ser Trp Thr
                485                 490                 495

His Arg Ser Ala Asp Arg Thr Asn Thr Ile Gly Pro Asn Arg Ile Thr
            500                 505                 510

Gln Ile Pro Ala Val Lys Gly Asn Leu Leu Phe Asn Gly Ser Val Ile
        515                 520                 525

Ser Gly Pro Gly Phe Thr Gly Gly Asp Leu Val Arg Leu Asn Asn Ser
    530                 535                 540

Gly Asn Asn Ile Gln Asn Arg Gly Tyr Leu Glu Val Pro Ile Gln Phe
545                 550                 555                 560

Thr Ser Thr Ser Thr Arg Tyr Arg Val Arg Val Arg Tyr Ala Ser Val
                565                 570                 575

Thr Pro Ile His Leu Ser Val Asn Trp Gly Asn Ser Asn Ile Phe Ser
            580                 585                 590

Ser Thr Val Pro Ala Thr Ala Ala Ser Leu Asp Asn Leu Gln Ser Arg
        595                 600                 605

Asp Phe Gly Tyr Phe Glu Ser Thr Asn Ala Phe Thr Ser Val Thr Gly
    610                 615                 620

Asn Val Val Gly Val Arg Asn Phe Ser Glu Asn Ala Arg Val Ile Ile
625                 630                 635                 640

Asp Arg Phe Glu Phe Ile Pro Val Thr Ala Thr Phe Glu Ala Glu Tyr
                645                 650                 655

Asp Leu Glu Arg Ala Gln Glu Ala Val Asn Ala Leu Phe Thr Asn Thr
            660                 665                 670

Asn Pro Arg Arg Leu Lys Thr Gly Val Thr Asp Tyr His Ile Asp Glu
        675                 680                 685

Val Ser Asn Leu Val Ala Cys Leu Ser Asp Glu Phe Cys Leu Asp Glu
    690                 695                 700

Lys Arg Glu Leu Leu Glu Lys Val Lys Tyr Ala Lys Arg Leu Ser Asp
705                 710                 715                 720

Glu Arg Asn Leu Leu Gln Asp Pro Asn Phe Thr Ser Ile Asn Lys Gln
                725                 730                 735

Pro Asp Phe Ile Ser Thr Asn Glu Gln Ser Asn Phe Thr Ser Ile His
            740                 745                 750

Glu Gln Ser Glu His Gly Trp Trp Gly Ser Glu Asn Ile Thr Ile Gln
        755                 760                 765

Glu Gly Asn Asp Val Phe Lys Glu Asn Tyr Val Thr Leu Pro Gly Thr
    770                 775                 780

Tyr Asn Glu Cys Tyr Pro Thr Tyr Leu Tyr Gln Lys Ile Gly Glu Ser
```

-continued

```
785                 790                 795                 800

Glu Leu Lys Ala Tyr Thr Arg Tyr Gln Leu Arg Gly Tyr Ile Glu Asp
                805                 810                 815

Ser Gln Asp Leu Glu Ile Tyr Leu Ile Arg Tyr Asn Ala Lys His Glu
            820                 825                 830

Thr Leu Asp Val Pro Gly Thr Glu Ser Val Trp Pro Leu Ser Val Glu
        835                 840                 845

Ser Pro Ile Arg Arg Cys Gly Glu Pro Asn Arg Cys Ala Pro His Phe
    850                 855                 860

Glu Trp Asn Pro Asp Leu Asp Cys Ser Cys Arg Asp Gly Glu Lys Cys
865                 870                 875                 880

Ala His His Ser His His Phe Ser Leu Asp Ile Asp Val Gly Cys Ile
                885                 890                 895

Asp Leu His Glu Asn Leu Gly Val Trp Val Val Phe Lys Ile Lys Thr
            900                 905                 910

Gln Glu Gly His Ala Arg Leu Gly Asn Leu Glu Phe Ile Glu Glu Lys
        915                 920                 925

Pro Leu Leu Gly Glu Ala Leu Ser Arg Val Lys Arg Ala Glu Lys Lys
    930                 935                 940

Trp Arg Asp Lys Arg Glu Lys Leu Gln Leu Glu Thr Lys Arg Val Tyr
945                 950                 955                 960

Thr Glu Ala Lys Glu Ala Val Asp Ala Leu Phe Val Asp Ser Gln Tyr
                965                 970                 975

Asp Arg Leu Gln Ala Asp Thr Asn Ile Gly Met Ile His Ala Ala Asp
            980                 985                 990

Lys Leu Val His Arg Ile Arg Glu  Ala Tyr Leu Ser Glu  Leu Ser Val
        995                 1000                1005

Ile Pro  Gly Val Asn Ala Glu  Ile Phe Glu Glu Leu  Glu Gly Arg
    1010                1015                1020

Ile Ile  Thr Ala Ile Ser Leu  Tyr Asp Ala Arg Asn  Val Val Lys
    1025                1030                1035

Asn Gly  Asp Phe Asn Asn Gly  Leu Ala Cys Trp Asn  Val Lys Gly
    1040                1045                1050

His Val  Asp Val Gln Gln Ser  His His Arg Ser Val  Leu Val Ile
    1055                1060                1065

Pro Glu  Trp Glu Ala Glu Val  Ser Gln Ala Val Arg  Val Cys Pro
    1070                1075                1080

Gly Arg  Gly Tyr Ile Leu Arg  Val Thr Ala Tyr Lys  Glu Gly Tyr
    1085                1090                1095

Gly Glu  Gly Cys Val Thr Ile  His Glu Ile Glu Asn  Asn Thr Asp
    1100                1105                1110

Glu Leu  Lys Phe Lys Asn Cys  Glu Glu Glu Glu Val  Tyr Pro Thr
    1115                1120                1125

Asp Thr  Gly Thr Cys Asn Asp  Tyr Thr Ala His Gln  Gly Thr Ala
    1130                1135                1140

Ala Cys  Asn Ser Arg Asn Ala  Gly Tyr Glu Asp Ala  Tyr Glu Val
    1145                1150                1155

Asp Thr  Thr Ala Ser Val Asn  Tyr Lys Pro Thr Tyr  Glu Glu Glu
    1160                1165                1170

Thr Tyr  Thr Asp Val Arg Arg  Asp Asn His Cys Glu  Tyr Asp Arg
    1175                1180                1185

Gly Tyr  Val Asn Tyr Pro Pro  Leu Pro Ala Gly Tyr  Val Thr Lys
    1190                1195                1200
```

```
Glu Leu  Glu Tyr Phe Pro Glu  Thr Asp Lys Val Trp  Ile Glu Leu
    1205                 1210                 1215

Gly Glu  Thr Glu Gly Thr Phe  Leu Val Asp Ser Ile  Glu Leu Leu
    1220                 1225                 1230

Leu Met  Glu Glu
    1235


<210> SEQ ID NO 44
<211> LENGTH: 715
<212> TYPE: PRT
<213> ORGANISM: Artificial Sequence
<220> FEATURE:
<223> OTHER INFORMATION: Mutant BT-0022 protein

<400> SEQUENCE: 44

Met Lys Ser Lys Asn Gln Asn Met His Gln Ser Leu Ser Asn Asn Ala
1               5                   10                  15

Thr Val Asp Lys Asn Phe Thr Gly Ser Leu Glu Asn Asn Thr Asn Thr
            20                  25                  30

Glu Leu Gln Asn Phe Asn His Glu Gly Ile Glu Pro Phe Val Ser Val
        35                  40                  45

Ser Thr Ile Gln Thr Gly Ile Gly Ile Ala Gly Lys Ile Leu Gly Asn
    50                  55                  60

Leu Gly Val Pro Phe Ala Gly Gln Val Ala Ser Leu Tyr Ser Phe Ile
65                  70                  75                  80

Leu Gly Glu Leu Trp Pro Lys Gly Lys Ser Gln Trp Glu Ile Phe Met
                85                  90                  95

Glu His Val Glu Glu Leu Ile Asn Gln Lys Ile Ser Thr Tyr Ala Arg
            100                 105                 110

Asn Lys Ala Leu Ala Asp Leu Lys Gly Leu Gly Asp Ala Leu Ala Val
        115                 120                 125

Tyr His Glu Ser Leu Glu Ser Trp Ile Lys Asn Arg Asn Asn Thr Arg
    130                 135                 140

Thr Arg Ser Val Val Lys Ser Gln Tyr Ile Thr Leu Glu Leu Met Phe
145                 150                 155                 160

Val Gln Ser Leu Pro Ser Phe Ala Val Ser Gly Glu Glu Val Pro Leu
                165                 170                 175

Leu Pro Ile Tyr Ala Gln Ala Ala Asn Leu His Leu Leu Leu Leu Arg
            180                 185                 190

Asp Ala Ser Ile Phe Gly Lys Glu Trp Gly Leu Ser Asp Ser Glu Ile
        195                 200                 205

Ser Thr Phe Tyr Asn Arg Gln Val Glu Arg Thr Ser Asp Tyr Ser Asp
    210                 215                 220

His Cys Thr Lys Trp Phe Asp Thr Gly Leu Asn Arg Leu Lys Gly Ser
225                 230                 235                 240

Asn Ala Glu Ile Trp Val Lys Tyr Asn Gln Phe Arg Arg Asp Met Thr
                245                 250                 255

Leu Met Val Leu Asp Leu Val Ala Leu Phe Gln Ser Tyr Asp Thr His
            260                 265                 270

Met Tyr Pro Ile Lys Thr Thr Ala Gln Leu Thr Arg Glu Val Tyr Thr
        275                 280                 285

Asn Ala Ile Gly Thr Val His Pro His Pro Ser Phe Thr Ser Thr Thr
    290                 295                 300

Trp Tyr Asn Asn Asn Ala Pro Ser Phe Ser Ala Ile Glu Ala Ala Val
305                 310                 315                 320
```

```
Ile Arg Ser Pro His Leu Leu Asp Phe Leu Glu Gln Val Thr Ile Tyr
                325                 330                 335

Ser Leu Leu Ser Arg Trp Ser Asn Thr Gln Tyr Met Asn Met Trp Gly
            340                 345                 350

Gly His Lys Leu Glu Phe Arg Thr Ile Gly Gly Thr Leu Asn Thr Ser
        355                 360                 365

Thr Gln Gly Ser Thr Asn Thr Ser Ile Asn Pro Val Thr Leu Pro Phe
    370                 375                 380

Thr Ser Arg Asp Ile Tyr Arg Thr Glu Ser Leu Ala Gly Leu Asn Leu
385                 390                 395                 400

Phe Leu Thr Gln Pro Val Asn Gly Val Pro Arg Val Asp Phe His Trp
                405                 410                 415

Lys Phe Val Thr His Pro Ile Ala Ser Asp Asn Phe Tyr Tyr Pro Gly
            420                 425                 430

Tyr Ala Gly Ile Gly Thr Gln Leu Gln Asp Ser Glu Asn Glu Leu Pro
        435                 440                 445

Pro Glu Thr Thr Gly Gln Pro Asn Tyr Glu Ser Tyr Ser His Arg Leu
    450                 455                 460

Ser His Ile Gly Leu Ile Ser Ala Ser His Val Lys Ala Leu Val Tyr
465                 470                 475                 480

Ser Trp Thr His Arg Ser Ala Asp Arg Thr Asn Thr Ile His Ser Asp
                485                 490                 495

Ser Ile Thr Gln Ile Pro Leu Val Lys Ala His Thr Leu Gln Ser Gly
            500                 505                 510

Thr Thr Val Val Lys Gly Pro Gly Phe Thr Gly Gly Asp Ile Leu Arg
        515                 520                 525

Arg Thr Ser Gly Gly Pro Phe Ala Phe Ser Asn Val Asn Leu Asp Trp
    530                 535                 540

Asn Leu Ser Gln Arg Tyr Arg Ala Arg Ile Arg Tyr Ala Ser Thr Thr
545                 550                 555                 560

Asn Leu Arg Met Tyr Val Thr Ile Ala Gly Glu Arg Ile Phe Ala Gly
                565                 570                 575

Gln Phe Asn Lys Thr Met Asn Thr Gly Asp Pro Leu Thr Phe Gln Ser
            580                 585                 590

Phe Ser Tyr Ala Thr Ile Asp Thr Ala Phe Thr Phe Pro Thr Lys Ala
        595                 600                 605

Ser Ser Leu Thr Val Gly Ala Asp Thr Phe Ser Ser Gly Asn Glu Val
    610                 615                 620

Tyr Val Asp Arg Phe Glu Leu Ile Pro Val Thr Ala Thr Leu Glu Ala
625                 630                 635                 640

Val Thr Asp Leu Glu Arg Ala Gln Lys Ala Val His Glu Leu Phe Thr
                645                 650                 655

Ser Thr Asn Pro Gly Gly Leu Lys Thr Asp Val Ala Lys Asp His Tyr
            660                 665                 670

Thr Asn Thr Leu Ser Lys Ser Val Gln Ser Val Phe Arg Cys Arg Cys
        675                 680                 685

Ser Glu Arg Thr Arg Leu Tyr Arg Trp Gly Tyr Pro Ser Lys Lys Glu
    690                 695                 700

Tyr Trp Tyr Ile Trp Gly Tyr Thr Ser Lys Tyr
705                 710                 715
```

<210> SEQ ID NO 45
<211> LENGTH: 1094

<212> TYPE: PRT
<213> ORGANISM: Artificial Sequence
<220> FEATURE:
<223> OTHER INFORMATION: Mutant BT-0027 protein

<400> SEQUENCE: 45

```
Met Phe Leu Glu Gln Ile Glu Gln Leu Ile Asp Gln Arg Ile Glu Thr
1               5                   10                  15

Val Glu Arg Asn Arg Ala Ile Gln Thr Leu Ile Gly Leu Ser Asn Ser
            20                  25                  30

Tyr Asp Val Tyr Ile Glu Ala Leu Lys Glu Trp Glu Asn Asn Pro Asp
        35                  40                  45

Asn Ser Ala Ser Gln Glu Arg Val Arg Asn Arg Phe Arg Thr Thr Asp
    50                  55                  60

Asp Ala Leu Ile Thr Gly Ile Pro Leu Leu Ala Ile Pro Asn Phe Glu
65                  70                  75                  80

Ile Ala Thr Leu Ser Val Tyr Val Gln Ala Ala Asn Leu His Leu Ser
                85                  90                  95

Leu Leu Arg Asp Ala Val Phe Phe Gly Glu Arg Trp Gly Leu Thr Gln
            100                 105                 110

Ile Asn Val Asp Asp Leu Tyr Arg Arg Leu Thr Asn Asn Ile Arg Asn
        115                 120                 125

Tyr Ser Asp His Cys Ala Arg Trp Tyr Asn Glu Gly Leu Asp Asn Ile
    130                 135                 140

Ser Gly Leu Ser Arg Ser Ile Asn Phe Gln Arg Glu Val Thr Ile Ser
145                 150                 155                 160

Val Leu Asp Ile Val Ala Leu Phe Pro Asn Tyr Asp Ile Arg Thr Tyr
                165                 170                 175

Pro Ile Ser Thr Thr Ser Gln Leu Thr Arg Glu Ile Phe Thr Ser Pro
            180                 185                 190

Ile Val Val Pro Asn Asp Phe Ser Val Ala Tyr Glu Gly Val Arg Arg
        195                 200                 205

Ala Pro His Leu Phe Glu Phe Leu Glu Lys Leu Val Ile Tyr Thr Gly
    210                 215                 220

Asp Arg Ser Gly Ile Arg His Trp Ala Gly His Glu Ile Thr Ser Arg
225                 230                 235                 240

Arg Thr Asp Ser Tyr His Gly Ile Ile Arg Tyr Pro Leu Tyr Gly Thr
                245                 250                 255

Ala Ala Asn Ala Glu Ser Pro Tyr Thr Leu Ala Leu Gln Pro Ser Glu
            260                 265                 270

Ser Ile Tyr Arg Thr Leu Ser Glu Pro Ile Phe Ser Gln Thr Gly Gly
        275                 280                 285

Leu Ser Pro His Arg Arg Arg Val Val Glu Gly Val Glu Phe Ser Ile
    290                 295                 300

Val Asn Asn Asn Val Asn Pro Ser Ser Phe Val Tyr Arg Arg Lys Gly
305                 310                 315                 320

Ser Leu Asp Ser Phe Thr Glu Leu Pro Pro Glu Asp Glu Ser Val Pro
                325                 330                 335

Pro Tyr Ile Gly Tyr Ser His Gln Leu Cys His Val Gly Phe Gly Arg
            340                 345                 350

Thr Asn Val Ile Phe Glu Pro Ser Asn Phe Ala Arg Val Pro Val Phe
        355                 360                 365

Ser Trp Thr His Arg Ser Ala Thr Pro Thr Asn Thr Ile Asp Pro Asp
    370                 375                 380
```

-continued

```
Arg Ile Thr Gln Ile Pro Ser Val Lys Ala Ser Ser Leu Arg Asn Ser
385                 390                 395                 400

Thr Val Val Ser Gly Pro Gly Phe Thr Gly Gly Asp Ile Val Arg Met
                405                 410                 415

Gly Ala Val His Gln Ile Tyr Ala Thr Asp Leu Ser Met Asn Val Arg
            420                 425                 430

Pro Ser Val Ala Leu Ser Arg Tyr Leu Ile Arg Leu Arg Tyr Ala Cys
        435                 440                 445

Arg Gly Ser Ser Asn Ile Val Ile His Gly Pro Ser Ile Arg Phe Val
    450                 455                 460

Ser Leu Pro Ser Thr Met Ser Asn Asp Glu Pro Leu Thr Tyr Gln Ser
465                 470                 475                 480

Phe Arg Tyr Ala Ser Ile Thr Thr Pro Ile Thr Arg Pro Ile Tyr Asn
                485                 490                 495

Met Phe Asn Leu Ser Ile Ser Arg Ile Ser Gly Val Gln Asn Leu Phe
            500                 505                 510

Ile Asp Arg Ile Glu Phe Ile Pro Val Asp Ala Asn Phe Glu Ala Glu
        515                 520                 525

Arg Asp Leu Glu Arg Ala Gln Lys Ala Val Asn Ala Leu Phe Thr Ser
    530                 535                 540

Thr Asn Gln Arg Gly Leu Lys Ile Asp Val Thr Asp Tyr His Ile Asp
545                 550                 555                 560

Gln Val Ser Asn Leu Val Asp Cys Leu Ser Asp Glu Phe Cys Leu Asp
                565                 570                 575

Glu Lys Arg Glu Leu Ser Glu Lys Ser Lys His Ala Lys Arg Leu Ser
            580                 585                 590

Asp Glu Arg Asn Leu Leu Gln Asp Leu Asn Phe Lys Asp Ile Asn Arg
        595                 600                 605

Gln Pro Glu Arg Gly Trp Ser Gly Ser Thr Gly Ile Thr Ile Gln Gly
    610                 615                 620

Gly Asp Asp Val Phe Lys Glu Asn Tyr Val Thr Leu Pro Gly Thr Phe
625                 630                 635                 640

Asp Glu Cys Tyr Pro Thr Tyr Leu Tyr Gln Lys Ile Asp Glu Ser Lys
                645                 650                 655

Leu Lys Ala Tyr Thr Arg Tyr Gln Leu Arg Gly Tyr Ile Glu Asp Ser
            660                 665                 670

Gln Asp Leu Glu Ile Tyr Leu Ile Arg Tyr Asn Ala Lys His Glu Thr
        675                 680                 685

Val Asn Val Pro Gly Ser Gly Ser Leu Trp Pro Leu Ser Val Glu Ser
    690                 695                 700

Ser Val Gly Lys Cys Gly Glu Pro Asn Arg Cys Ala Ser Arg Met Glu
705                 710                 715                 720

Trp Asn Pro Asp Leu Asp Cys Ser Cys Arg Asp Gly Glu Lys Cys Ala
                725                 730                 735

His His Ser His His Phe Ser Leu Asp Ile Asp Val Gly Cys Thr Asp
            740                 745                 750

Leu Asn Glu Asp Leu Gly Val Trp Val Ile Phe Lys Ile Lys Thr Gln
        755                 760                 765

Asp Gly His Ala Lys Ile Gly Asn Leu Glu Phe Leu Lys Glu Lys Leu
    770                 775                 780

Leu Leu Gly Glu Ala Leu Ala Arg Val Lys Lys Ala Glu Lys Lys Trp
785                 790                 795                 800

Arg Asp Lys Arg Asp Lys Leu Glu Trp Glu Thr Asn Val Val Tyr Lys
```

```
                805                 810                 815

Glu Ala Lys Glu Ser Val Asp Ala Leu Phe Val Asp Ser Gln Tyr Ser
            820                 825                 830

Arg Leu Gln Ala Asp Thr Asn Ile Ala Met Ile His Ala Ala Asp Lys
        835                 840                 845

Arg Val His Arg Ile Arg Glu Ala Tyr Leu Pro Glu Leu Thr Val Ile
    850                 855                 860

Pro Gly Val Asn Ala Ser Ile Phe Glu Glu Leu Glu Gly Arg Ile Phe
865                 870                 875                 880

Thr Ala Tyr Ser Leu Tyr Gly Ala Arg Asn Val Ile Lys Asn Gly Asp
                885                 890                 895

Phe Asn Asn Gly Leu Ser Cys Trp Asn Val Lys Gly His Val Glu Val
            900                 905                 910

Gln Gln Ile His His Arg Ser Val Leu Val Val Pro Ser Trp Lys Thr
        915                 920                 925

Glu Val Ser Gln Glu Val Cys Val Cys Pro Gly Arg Gly Tyr Ile Leu
    930                 935                 940

Arg Val Thr Ala Tyr Lys Glu Gly Tyr Gly Glu Gly Asn Val Thr Ile
945                 950                 955                 960

His Glu Ile Glu Asn Asn Thr Asp Glu Leu Lys Phe Arg Asn Cys Glu
                965                 970                 975

Glu Glu Glu Val Tyr Pro Asn Asn Thr Val Thr Cys Asn Asp Tyr Thr
            980                 985                 990

Val Asn Gln Glu Glu Tyr Lys Gly  Thr Cys Thr Ser Arg  Asn Arg Gly
        995                 1000                1005

Tyr Asp  Glu Ser Tyr Glu Ser  Ser Ser Ser Glu Ser  Ala Tyr Tyr
    1010                1015                1020

Ala Ser  Val Tyr Glu Glu Lys  Gly Tyr Thr Asp Gly  Arg Arg Glu
    1025                1030                1035

Asn Leu  Cys Glu Phe Asn Arg  Gly Tyr Gly Asp Tyr  Thr Ser Ile
    1040                1045                1050

Pro Thr  Ala Tyr Val Thr Lys  Glu Leu Glu Tyr Phe  Pro Glu Thr
    1055                1060                1065

Asp Lys  Val Trp Ile Glu Leu  Gly Glu Thr Glu Gly  Ala Phe Ile
    1070                1075                1080

Leu Asp  Ser Val Glu Leu Leu  Leu Met Glu Glu
    1085                1090


<210> SEQ ID NO 46
<211> LENGTH: 1169
<212> TYPE: PRT
<213> ORGANISM: Artificial Sequence
<220> FEATURE:
<223> OTHER INFORMATION: Mutant BT-0029 protein

<400> SEQUENCE: 46

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
```

```
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255

Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala Phe Asn Leu His Ser Gly Ala Thr Ile Val Lys Gly Pro
465                 470                 475                 480

Gly Phe Thr Gly Gly Asp Ile Leu Arg Arg Thr Asn Val Gly Ser Phe
                485                 490                 495
```

-continued

```
Gly Asp Met Arg Val Asn Ile Thr Ala Pro Leu Ser Gln Arg Tyr Arg
            500                 505                 510

Val Arg Ile Arg Tyr Ala Ser Thr Thr Asp Leu Gln Phe Tyr Thr Asn
        515                 520                 525

Ile Asn Gly Thr Thr Ile Asn Ile Gly Asn Phe Ser Ser Thr Met Asp
    530                 535                 540

Ser Gly Asp Asp Leu Gln Tyr Gly Arg Phe Arg Val Ala Gly Phe Thr
545                 550                 555                 560

Thr Pro Phe Thr Phe Ser Asp Ala Met Ser Thr Phe Thr Ile Gly Ala
                565                 570                 575

Phe Ser Phe Ser Ser Asn Asn Glu Val Tyr Ile Asp Arg Ile Glu Phe
            580                 585                 590

Val Pro Ala Glu Val Thr Phe Glu Ala Glu Tyr Asp Leu Glu Lys Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
            660                 665                 670

Gln Asp Pro Asn Phe Arg Gly Ile Asn Arg Gln Pro Asp Arg Gly Trp
        675                 680                 685

Arg Gly Ser Thr Asp Ile Thr Ile Gln Gly Gly Asp Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Gln Ser Pro Ile Gly Lys Cys Gly
    770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
    850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Glu Ala Lys Lys Ser Val
                885                 890                 895

Asp Ala Leu Phe Val Asn Ser Gln Tyr Asp Arg Leu Gln Ala Asp Thr
            900                 905                 910
```

```
Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
    930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                 1005

Val Arg  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  Asn Thr Asp Glu Leu  Lys Phe Ser Asn Cys  Val Glu Glu
    1040                 1045                 1050

Glu Ile  Tyr Pro Asn Asn Thr  Val Thr Cys Asn Asp  Tyr Thr Ala
    1055                 1060                 1065

Thr Gln  Glu Glu Tyr Glu Gly  Thr Tyr Thr Ser Arg  Asn Arg Gly
    1070                 1075                 1080

Tyr Asp  Gly Ala Tyr Glu Ser  Asn Ser Ser Val Pro  Ala Asp Tyr
    1085                 1090                 1095

Ala Ser  Ala Tyr Glu Glu Lys  Ala Tyr Thr Asp Gly  Arg Arg Asp
    1100                 1105                 1110

Asn Thr  Cys Glu Ser Asn Arg  Gly Tyr Gly Asp Tyr  Thr Pro Leu
    1115                 1120                 1125

Pro Ala  Gly Tyr Val Thr Lys  Glu Leu Glu Tyr Phe  Pro Glu Thr
    1130                 1135                 1140

Asp Lys  Val Trp Leu Glu Ile  Gly Glu Thr Glu Gly  Thr Phe Ile
    1145                 1150                 1155

Val Asp  Ser Val Glu Leu Leu  Ile Met Glu Glu
    1160                 1165


<210> SEQ ID NO 47
<211> LENGTH: 1169
<212> TYPE: PRT
<213> ORGANISM: Artificial Sequence
<220> FEATURE:
<223> OTHER INFORMATION: Mutant BT-0020 protein

<400> SEQUENCE: 47

Met Glu Val Asn His Gln Asn Glu Cys Val Pro Tyr Asn Cys Leu Lys
1               5                   10                  15

Asn Pro Lys Ile Glu Met Leu Asp Ile Glu Gly Ile Ser Ser Arg Ser
            20                  25                  30

Arg Glu Gln Val Ala Glu Ile Ser Leu Gly Leu Thr Arg Phe Leu Leu
        35                  40                  45

Glu Ser Leu Leu Pro Gly Ala Ser Phe Gly Phe Gly Leu Phe Asp Ile
    50                  55                  60

Ile Trp Gly Val Ile Gly Pro Asp Gln Trp Ser Leu Phe Leu Thr Gln
65                  70                  75                  80

Ile Glu Gln Leu Ile Asp Gln Arg Ile Glu Ala His Val Arg Asn Gln
                85                  90                  95
```

```
Ala Ile Ser Arg Leu Glu Gly Leu Gly Asp Ser Tyr Glu Val Tyr Ile
            100                 105                 110

Glu Ser Leu Arg Glu Trp Glu Ala Ser Pro Asn Asn Glu Ser Leu Gln
        115                 120                 125

Gln Asp Val Arg Asn Arg Phe Ser Asn Thr Asp Asn Ala Leu Ile Thr
    130                 135                 140

Ala Ile Pro Ile Leu Arg Glu Gln Gly Phe Glu Ile Pro Leu Leu Thr
145                 150                 155                 160

Val Tyr Val Gln Ala Ala Asn Leu His Leu Ser Leu Leu Arg Asp Ala
                165                 170                 175

Val Tyr Phe Gly Gln Arg Trp Gly Leu Asp Thr Ala Thr Val Asn Asn
            180                 185                 190

His Tyr Asn Arg Leu Ile Asn Leu Ile Asn Thr Tyr Ser Asp His Cys
        195                 200                 205

Ala Gln Trp Phe Asn Arg Gly Leu Asp Asn Phe Gly Val Val Thr Ala
    210                 215                 220

Arg Tyr Leu Asp Phe Gln Arg Glu Val Thr Ile Ser Val Leu Asp Ile
225                 230                 235                 240

Val Ala Leu Phe Pro Asn Tyr Asp Ile Arg Thr Tyr Pro Ile Gln Thr
                245                 250                 255

Leu Ser Gln Leu Thr Arg Glu Ile Tyr Thr Ser Pro Val Ala Glu Pro
            260                 265                 270

Gly Ala Ser Leu Asn Val Asp Leu Arg Asn Ile Leu Arg Glu Pro His
        275                 280                 285

Leu Met Asp Phe Leu Thr Arg Leu Val Ile Tyr Thr Gly Val Gln Gly
    290                 295                 300

Gly Ile Tyr His Trp Ala Gly His Glu Ile Ser Ser Arg Thr Thr Gly
305                 310                 315                 320

Asn Leu Ser Ser Asn Ile Gln Phe Pro Leu Tyr Gly Thr Ser Ala Asn
                325                 330                 335

Ala Asp Arg Pro Phe Asn Leu Ala Ile His Tyr Ser Glu Thr Ile Tyr
            340                 345                 350

Arg Thr Leu Ser Ala Pro Ile Tyr Ser Val Ser Gly Gly Ile Ser Pro
        355                 360                 365

Asn Arg Thr Arg Ala Val Glu Gly Val Arg Phe Leu Thr Ala Arg Asp
    370                 375                 380

Asn Asn Leu Asn Ser Leu Pro Phe Leu Tyr Arg Lys Glu Gly Ser Leu
385                 390                 395                 400

Asp Ser Phe Thr Glu Leu Pro Pro Glu Asp Glu Asn Glu Pro Pro Tyr
                405                 410                 415

Ile Gly Tyr Ser His Arg Leu Cys His Ala Arg Phe Ala Arg Ser Ser
            420                 425                 430

Val Val Leu Glu Pro Ser Asn Phe Ala Arg Ile Pro Val Phe Ser Trp
        435                 440                 445

Thr His Arg Ser Ala Gly Pro Thr Asn Glu Val Ser Ser Ser Arg Ile
    450                 455                 460

Thr Gln Ile Pro Trp Val Lys Ala His Thr Leu Asp Ser Gly Ala Phe
465                 470                 475                 480

Val Ile Lys Gly Pro Gly Phe Thr Gly Gly Asp Ile Leu Thr Arg Pro
                485                 490                 495

Asn Leu Gly Thr Leu Gly Ala Leu Arg Val Thr Leu Thr Gly Gln Leu
            500                 505                 510

Pro Gln Thr Tyr Asn Ile Arg Ile Arg Tyr Ala Ser Ile Ala Asn Arg
```

```
        515                 520                 525

Gly Gly Thr Leu Ile Phe Ser Gln Pro Pro Ser Tyr Gly Leu Thr Phe
    530                 535                 540

Pro Lys Thr Met Asp Ile Asp Glu Pro Leu Thr Ser Arg Ser Phe Ala
545                 550                 555                 560

Arg Thr Thr Leu Phe Thr Pro Ile Thr Phe Thr Gln Ala Gln Ala Glu
                565                 570                 575

Leu Asn Leu Thr Ile Gln Gln Gly Val Tyr Ile Asp Arg Ile Glu Phe
            580                 585                 590

Ile Pro Val Asn Ala Thr Phe Glu Ala Glu Tyr Asp Leu Glu Arg Ala
        595                 600                 605

Gln Lys Ala Val Asn Ala Leu Phe Thr Ser Ser Asn Gln Leu Gly Leu
    610                 615                 620

Lys Thr Asp Leu Thr Asp Tyr His Ile Asp Gln Val Ser Asn Leu Val
625                 630                 635                 640

Asp Cys Leu Ser Asp Glu Phe Cys Ile Asp Glu Lys Arg Glu Leu Ser
                645                 650                 655

Glu Lys Val Lys His Ala Lys Arg Leu Ser Asp Glu Arg Asn Leu Leu
            660                 665                 670

Gln Asp Ser Asn Phe Arg Gly Ile Asn Arg Gln Pro Asp Arg Gly Trp
        675                 680                 685

Arg Gly Ser Thr Asp Ile Thr Ile Gln Gly Gly Asn Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Gln Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Val Glu Ser Pro Ile Gly Lys Cys Gly
    770                 775                 780

Glu Pro Asn Arg Cys Val Pro Gln Leu Glu Trp Asn Ser Asn Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu His Asp Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
    850                 855                 860

Ala Arg Val Lys Arg Ala Glu Lys Lys Trp Arg Asp Lys Arg Glu Thr
865                 870                 875                 880

Leu Gln Leu Glu Thr Asn Ile Val Tyr Lys Glu Ala Lys Glu Ser Val
                885                 890                 895

Asp Ala Leu Phe Ala Asn Ser Gln Tyr Asn Arg Leu Gln Ala Asp Thr
            900                 905                 910

Asn Ile Ala Met Ile His Ala Ala Asp Lys Arg Val His Arg Ile Arg
        915                 920                 925

Glu Ala Tyr Leu Pro Glu Leu Ser Val Ile Pro Gly Val Asn Ala Gly
    930                 935                 940
```

```
Ile Phe Glu Glu Leu Glu Gly Arg Ile Phe Thr Ala Phe Ser Leu Tyr
945                 950                 955                 960

Asp Ala Arg Asn Val Ile Lys Asn Ser Asp Phe Asn Asn Gly Leu Ser
                965                 970                 975

Cys Trp Asn Val Lys Gly His Val Asp Ile Glu Glu Gln Asn Asn His
            980                 985                 990

Arg Ser Val Leu Val Val Pro Glu  Trp Glu Ala Glu Val  Ser Gln Lys
        995                 1000                 1005

Val His  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  His Thr Asp Glu Leu  Lys Phe Arg Asn Cys  Glu Glu Asp
    1040                 1045                 1050

Glu Val  Tyr Pro Asn Asn Thr  Arg Thr Cys Asn Ala  Tyr Pro Ala
    1055                 1060                 1065

Asp Gln  Glu Gly Tyr Glu Gly  Ala Cys Thr Ser Arg  Asn Arg Gly
    1070                 1075                 1080

Tyr Asp  Glu Val Tyr Gly Asn  Thr Pro Ser Leu Pro  Ala Asp Tyr
    1085                 1090                 1095

Ala Pro  Ile Tyr Glu Glu Asn  Ala Tyr Thr Asp Gly  Arg Arg Gly
    1100                 1105                 1110

Asn Pro  Cys Glu Ser Ser Arg  Gly Tyr Gly Asp Tyr  Thr Pro Leu
    1115                 1120                 1125

Pro Ala  Gly Tyr Glu Thr Lys  Glu Leu Glu Tyr Phe  Pro Glu Thr
    1130                 1135                 1140

Asp Thr  Val Trp Ile Lys Leu  Gly Glu Thr Glu Gly  Thr Phe Ile
    1145                 1150                 1155

Val Asp  Ser Val Glu Leu Leu  Ile Met Glu Glu
    1160                 1165


<210> SEQ ID NO 48
<211> LENGTH: 719
<212> TYPE: PRT
<213> ORGANISM: Artificial Sequence
<220> FEATURE:
<223> OTHER INFORMATION: Mutant BT-0031 protein

<400> SEQUENCE: 48

Met Lys Leu Lys Asn Pro Asp Lys His Gln Ser Leu Ser Ser Asn Ala
1               5                   10                  15

Lys Val Asp Lys Ile Ala Thr Asp Ser Leu Lys Asn Glu Thr Asp Ile
            20                  25                  30

Glu Leu Lys Asn Met Asn Asn Glu Asp Tyr Leu Arg Met Ser Glu His
        35                  40                  45

Glu Ser Ile Asp Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Ile Ala Ser Leu Tyr Ser Phe Ile Leu Gly Glu Leu Trp Pro Lys
                85                  90                  95

Gly Lys Ser Gln Trp Glu Ile Phe Met Glu His Val Glu Glu Ile Ile
            100                 105                 110

Asn Gln Lys Ile Leu Thr Tyr Ala Arg Asn Lys Ala Leu Ser Asp Leu
        115                 120                 125
```

```
Arg Gly Leu Gly Asp Ala Leu Ala Val Tyr His Glu Ser Leu Glu Ser
    130                 135                 140

Trp Val Lys Asn Arg Asn Asn Thr Arg Ala Arg Ser Val Val Lys Asn
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205

Glu Trp Gly Leu Ser Ala Ser Glu Ile Ser Thr Phe Tyr Asn Arg Gln
    210                 215                 220

Val Glu Arg Thr Arg Asp Tyr Ser Asp His Cys Val Lys Trp Tyr Asn
225                 230                 235                 240

Thr Gly Leu Asn Asn Leu Arg Gly Thr Asn Ala Lys Ser Trp Val Arg
                245                 250                 255

Tyr Asn Gln Phe Arg Lys Asp Met Thr Leu Met Val Leu Asp Leu Val
            260                 265                 270

Ala Leu Phe Pro Ser Tyr Asp Thr Leu Val Tyr Pro Ile Lys Thr Thr
        275                 280                 285

Ser Gln Leu Thr Arg Glu Val Tyr Thr Asp Ala Ile Gly Thr Val His
    290                 295                 300

Pro Ser Gly Ala Val Ala Ser Thr Thr Trp Tyr Asn Asn Asn Ala Pro
305                 310                 315                 320

Ser Phe Ser Thr Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Thr Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Thr Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Asn Ser Asp Ser Ile Thr Gln Ile Pro Leu
            500                 505                 510

Val Lys Ala Phe Asn Leu Pro Ser Gly Ala Ser Val Val Arg Gly Pro
        515                 520                 525

Gly Phe Thr Gly Gly Asp Ile Leu Arg Arg Thr Asn Thr Gly Thr Phe
    530                 535                 540
```

-continued

```
Gly Asp Ile Arg Val Asn Ile Asn Pro Pro Phe Ala Gln Arg Tyr Arg
545                 550                 555                 560

Leu Arg Ile Arg Tyr Ala Ser Thr Thr Asn Leu Glu Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Ala Phe Arg Thr Val Gly Phe Thr
        595                 600                 605

Thr Pro Phe Ser Phe Ser Asn Ala Gln Ser Thr Phe Thr Ile Gly Ala
    610                 615                 620

Trp Asn Phe Ser Leu Gly Asn Glu Val Tyr Ile Asp Arg Ile Glu Phe
625                 630                 635                 640

Val Pro Val Glu Val Thr Tyr Glu Ala Glu His Asp Phe Glu Lys Ala
                645                 650                 655

Gln Glu Glu Val Thr Ala Leu Phe Thr Ser Thr Asn Pro Gly Gly Leu
            660                 665                 670

Lys Thr Asn Val Thr Glu Tyr His Ile Asp Gln Val Ser Asn Leu Val
        675                 680                 685

Glu Ser Leu Ser Asn Glu Phe Tyr Leu Asp Glu Lys Arg Glu Leu Phe
    690                 695                 700

Glu Leu Val Lys Tyr Ala Lys Gln Leu His Leu Gly Arg Asn Met
705                 710                 715


<210> SEQ ID NO 49
<211> LENGTH: 1164
<212> TYPE: PRT
<213> ORGANISM: Artificial Sequence
<220> FEATURE:
<223> OTHER INFORMATION: Mutant BT-0201 protein

<400> SEQUENCE: 49

Met Glu Arg Asn Asn Gln Asp Gln Cys Ile Pro Tyr Asn Cys Leu Asn
1               5                   10                  15

Asn Pro Glu Val Gly Ile Leu Asp Ile Glu Asn Phe Asn Leu Glu Leu
            20                  25                  30

Val Ser Gln Val Ser Val Gly Leu Thr Arg Phe Leu Leu Glu Ala Ser
        35                  40                  45

Ile Pro Gly Ala Gly Phe Ala Leu Gly Leu Phe Asp Ile Ile Trp Gly
    50                  55                  60

Ala Leu Gly Val Asp Gln Trp Ser Leu Phe Leu Ala Gln Ile Glu Gln
65                  70                  75                  80

Leu Ile Asn Glu Arg Ile Thr Thr Val Glu Arg Asn Arg Ala Ile Gln
                85                  90                  95

Ala Leu Ser Gly Leu Ser Ser Ser Tyr Glu Val Tyr Ile Glu Ala Leu
            100                 105                 110

Arg Glu Trp Glu Asn Asp Leu Asp Asn Pro Ala Ser Arg Asp Arg Val
        115                 120                 125

Val Ala Arg Phe Arg Ala Thr Asp Asn Ser Leu Ile Thr Asp Ile Pro
    130                 135                 140

Leu Leu Glu Ile Pro Gly Phe Glu Ile Ala Thr Leu Ser Val Tyr Thr
145                 150                 155                 160

Gln Ala Ala Asn Leu His Leu Ala Leu Leu Arg Asp Ala Val Tyr Phe
                165                 170                 175

Gly Glu Arg Trp Gly Leu Thr Gln Thr Asn Ile Glu Asp Leu His Thr
            180                 185                 190
```

```
Arg Leu Thr Arg Tyr Ile Gln Glu Tyr Ser Asp His Cys Ala Arg Trp
        195                 200                 205

Tyr Asn Gln Gly Leu Asn Asn Ile Gly Gly Ile Asn Thr Arg Tyr Leu
    210                 215                 220

Asp Phe Gln Arg Glu Leu Thr Ile Ser Val Leu Asp Ile Val Ala Leu
225                 230                 235                 240

Phe Pro Asn Tyr Asp Ile Arg Thr Tyr Pro Ile Pro Thr Gln Ser Gln
                245                 250                 255

Leu Thr Arg Glu Ile Tyr Thr Ser Pro Val Val Ala Pro Gly Val Asn
            260                 265                 270

Trp Ile Leu Ser Ile Ser Asn Val Leu Arg Ala Pro His Leu Met Asp
        275                 280                 285

Phe Phe Asp Arg Ile Ile Ile Tyr Thr Gly Thr Val Arg Ser Thr Pro
    290                 295                 300

His Trp Glu Gly His Glu Val Ile Ser Arg Arg Thr Gly Gln Gly Asn
305                 310                 315                 320

Glu Ile Arg Ser Pro Leu Tyr Gly Val Ala Ala Asn Ala Glu Pro Pro
                325                 330                 335

Val Thr Ile Arg Pro Thr Gly Phe Thr Asp Glu Gln Arg Gln Val Tyr
            340                 345                 350

Arg Val Leu Ser Arg Val Ala Ser Phe Arg Asn Ser Gly Thr Asn Phe
        355                 360                 365

Ser Leu Val Asp Ala Ala Ser Phe Leu Thr Ile Phe Ser Ala Ser Ser
    370                 375                 380

Ile Tyr Arg Asn Gly Phe Gly Phe Asn Ala Asp Thr Ile Asp Glu Ile
385                 390                 395                 400

Pro Ile Glu Gly Thr Asp Pro Tyr Ile Gly Tyr Ser His Arg Leu Cys
                405                 410                 415

His Val Gly Phe Thr Ala Ser Ser Pro Phe Ile Ser Gln Tyr Ala Arg
            420                 425                 430

Ala Pro Val Phe Ser Trp Thr His Arg Ser Ala Thr Phe Thr Asn Thr
        435                 440                 445

Ile Asp Pro Glu Arg Ile Thr Gln Ile Pro Met Val Lys Ala Tyr Asn
    450                 455                 460

Leu His Ala Gly Ala Thr Val Val Arg Gly Pro Gly Phe Thr Gly Gly
465                 470                 475                 480

Asp Leu Leu Arg Arg Thr Asn Thr Gly Thr Phe Ala Asp Ile Arg Val
                485                 490                 495

Asn Ile Thr Gly Pro Leu Ser Gln Arg Tyr Arg Val Arg Ile Arg Tyr
            500                 505                 510

Ala Ser Thr Thr Asp Leu Gln Phe Phe Thr Arg Ile Asn Gly Thr Ser
        515                 520                 525

Val Asn Gln Gly Asn Phe Gln Arg Thr Met Asn Arg Gly Asp Asn Leu
    530                 535                 540

Glu Ser Gly Asn Phe Arg Thr Ala Gly Phe Ser Thr Pro Phe Ser Phe
545                 550                 555                 560

Ser Asn Ala Gln Ser Thr Phe Thr Leu Gly Thr Gln Ala Phe Ser Asn
                565                 570                 575

Gln Glu Val Tyr Ile Asp Arg Ile Glu Phe Val Pro Ala Glu Val Thr
            580                 585                 590

Phe Glu Ala Glu Ser Asp Leu Glu Arg Ala Gln Lys Ala Val Asn Ala
        595                 600                 605

Leu Phe Thr Ser Thr Ser Gln Leu Gly Leu Lys Thr Asn Val Thr Gly
```

```
    610                 615                 620

Tyr His Ile Asp Gln Val Ser Asn Leu Val Ala Cys Leu Ser Asp Glu
625                 630                 635                 640

Phe Cys Leu Asp Glu Lys Arg Glu Leu Ser Glu Lys Val Lys His Ala
                645                 650                 655

Lys Arg Leu Ser Asp Lys Arg Asn Leu Leu Gln Asp Pro Asn Phe Arg
            660                 665                 670

Gly Ile Asn Arg Gln Pro Asp His Gly Trp Arg Gly Ser Thr Asp Ile
        675                 680                 685

Thr Ile Gln Gly Gly Asp Asp Val Phe Lys Glu Asn Tyr Val Thr Leu
    690                 695                 700

Pro Gly Thr Phe Asp Glu Cys Tyr Pro Thr Tyr Leu Tyr Gln Lys Ile
705                 710                 715                 720

Asp Glu Ser Lys Leu Lys Ala Tyr Thr Arg Tyr Gln Leu Arg Gly Tyr
                725                 730                 735

Ile Glu Asp Ser Gln Asp Leu Glu Ile Tyr Leu Ile Arg Tyr Asn Ser
            740                 745                 750

Lys His Glu Ile Val Asn Val Pro Gly Thr Gly Ser Leu Trp Pro Leu
        755                 760                 765

Ser Val Glu Asn Gln Ile Gly Pro Cys Gly Glu Pro Asn Arg Cys Ala
    770                 775                 780

Pro His Leu Glu Trp Asn Pro Asp Leu His Cys Ser Cys Arg Asp Gly
785                 790                 795                 800

Glu Lys Cys Val His His Ser His His Phe Ser Leu Asp Ile Asp Val
                805                 810                 815

Gly Cys Thr Asp Leu Asn Glu Asp Leu Gly Val Trp Leu Ile Phe Lys
            820                 825                 830

Ile Lys Thr Gln Asp Gly His Ala Arg Leu Gly Asn Leu Glu Phe Leu
        835                 840                 845

Glu Glu Glu Pro Leu Leu Gly Glu Ala Leu Ala Arg Val Lys Arg Ala
    850                 855                 860

Glu Lys Lys Trp Arg Asp Lys Arg Glu Lys Leu Gln Leu Glu Thr Asn
865                 870                 875                 880

Ile Val Tyr Lys Glu Ala Lys Glu Ser Val Asp Ala Leu Phe Val Asn
                885                 890                 895

Ser Gln Tyr Asp Arg Leu Gln Ala Asp Thr Asn Ile Ala Met Ile His
            900                 905                 910

Ala Ala Asp Lys Arg Val His Arg Ile Arg Glu Ala Tyr Leu Pro Glu
        915                 920                 925

Leu Ser Val Ile Pro Gly Val Asn Ala Ala Ile Phe Glu Glu Leu Glu
    930                 935                 940

Gly Arg Ile Phe Thr Ala Tyr Ser Leu Tyr Asp Ala Arg Asn Val Ile
945                 950                 955                 960

Lys Asn Gly Asn Phe Asn Asn Gly Leu Leu Cys Trp Asn Val Lys Gly
                965                 970                 975

His Val Asp Val Glu Glu Gln Asn Asn His Arg Ser Val Leu Val Ile
            980                 985                 990

Pro Glu Trp Glu Ala Glu Val Ser  Gln Lys Val Arg Val  Cys Pro Gly
        995                 1000                1005

Arg Gly  Tyr Ile Leu Arg Val  Thr Ala Tyr Lys Glu  Gly Tyr Gly
    1010                1015                1020

Glu Gly  Cys Val Thr Ile His  Glu Ile Glu Asp Asn  Thr Asp Glu
    1025                1030                1035
```

Leu Lys Phe Ser Asn Cys Val Glu Glu Gly Tyr Pro Asn Asn Thr
    1040                1045                1050

Val Thr Cys Asn Glu Tyr Thr Met Asn Gln Gly Val Gly Glu Cys
    1055                1060                1065

Thr Asp Ala Cys Asn Val Arg Asn Arg Gly Tyr Glu Asp Ala Tyr
    1070                1075                1080

Gly His Asn Pro Ser Thr Pro Val His Tyr Thr Thr Pro Tyr Glu
    1085                1090                1095

Glu Glu Thr Tyr Thr Asp Glu Arg Arg Glu Asn Pro Cys Glu Ala
    1100                1105                1110

Asn Lys Gly Tyr Val Asn Tyr Thr Pro Leu Pro Val Gly Tyr Val
    1115                1120                1125

Thr Lys Glu Leu Glu Tyr Phe Pro Glu Thr Asp Thr Val Trp Ile
    1130                1135                1140

Glu Ile Gly Glu Thr Glu Gly Thr Phe Leu Val Asp Ser Val Glu
    1145                1150                1155

Leu Leu Ile Met Glu Glu
    1160

<210> SEQ ID NO 50
<211> LENGTH: 1166
<212> TYPE: PRT
<213> ORGANISM: Artificial Sequence
<220> FEATURE:
<223> OTHER INFORMATION: Mutant BT-0202 protein

<400> SEQUENCE: 50

Met Lys Ile Asn Asn Gln Asn Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Met Ser Leu Leu Gln Phe Leu Leu Asn Asn
        35                  40                  45

Phe Val Pro Gly Gly Gly Val Ile Ser Gly Leu Ile Asn Lys Ile Trp
    50                  55                  60

Gly Ala Leu Arg Pro Ser Glu Trp Glu Leu Phe Leu Ala Gln Ile Glu
65                  70                  75                  80

Gln Leu Ile Asp Arg Arg Ile Glu Ala Ala Val Arg Ala Lys Ala Ile
                85                  90                  95

Ala Glu Leu Glu Gly Leu Gly Arg Ser Tyr Gln Leu Tyr Gly Glu Ala
            100                 105                 110

Phe Lys Glu Trp Glu Lys Thr Pro Asp Asn Thr Ala Ala Arg Ser Arg
        115                 120                 125

Val Thr Glu Arg Phe Arg Ile Ile Asp Ala Gln Ile Glu Ala Asn Ile
    130                 135                 140

Pro Ser Phe Arg Val Ser Gly Phe Glu Val Pro Leu Leu Ser Val Tyr
145                 150                 155                 160

Thr Gln Ala Ala Asn Leu His Leu Ala Leu Leu Arg Asp Ser Val Val
                165                 170                 175

Phe Gly Glu Arg Trp Gly Leu Thr Thr Thr Asn Val Asn Asp Ile Tyr
            180                 185                 190

Asn Arg Gln Val Lys Arg Ile Asp Glu Tyr Ser Asp His Cys Val Asp
        195                 200                 205

Thr Tyr Lys Thr Glu Leu Glu Arg Leu Glu Phe Ser Ser Ile Ala Gln
    210                 215                 220

Trp Arg Ile Tyr Asn Gln Phe Arg Arg Glu Leu Thr Leu Thr Val Leu
225 230 235 240

Asp Ile Val Ala Leu Phe Pro Asn Tyr Asp Gly Arg Leu Tyr Pro Ile
245 250 255

Arg Thr Ile Ser Gln Leu Thr Arg Asp Ile Tyr Thr Ser Pro Val Ser
260 265 270

Glu Phe Tyr Tyr Gly Pro Ile Tyr Asn Tyr Asn Ile Val Gly Arg Leu
275 280 285

Thr Glu Gln Gln Leu Arg Arg Pro His Leu Met Asp Phe Phe Asn Ser
290 295 300

Met Ile Met Tyr Thr Ser Asp Asn Arg Arg Glu His Tyr Trp Ser Gly
305 310 315 320

Leu Glu Met Lys Ala Thr Asp Thr Ser Gly Asn Gln Val Ser Phe Pro
325 330 335

Leu Ala Gly Thr Arg Gly Asn Ser Ala Pro Pro Val Thr Val Arg Asn
340 345 350

Asn Gly Glu Gly Val Tyr Arg Ile Leu Ser Glu Pro Phe Tyr Ser Ser
355 360 365

Pro Phe Leu Gly Thr Ser Val Leu Gly Ser Arg Gly Glu Glu Phe Ala
370 375 380

Phe Ala Ser Asn Thr Thr Thr Ser Leu Pro Ser Thr Ile Tyr Arg Asn
385 390 395 400

Arg Gly Thr Val Asp Ser Leu Val Ser Ile Pro Pro Gln Asp Tyr Ser
405 410 415

Val Pro Pro His Arg Gly Tyr Ser His Leu Leu Ser His Val Thr Met
420 425 430

His Asn Ser Ser Pro Ile Phe His Trp Thr His Arg Ser Ala Thr Pro
435 440 445

Arg Asn Thr Ile Asp Pro Asp Ser Ile Thr Gln Ile Pro Val Val Lys
450 455 460

Ala Ser His Leu Ser Gly Gly Ser Val Ile Lys Gly Pro Gly His Thr
465 470 475 480

Gly Gly Asp Leu Ile Ser Leu Pro Val Asn Asn Phe Thr His Phe Arg
485 490 495

Ile Pro Phe Gln Ala Asn Thr Pro Gln Arg Tyr Arg Ile Arg Ile Arg
500 505 510

Tyr Ala Ala Asp Ser Asp Gly Thr Leu Asp Ser Gly Val Phe Leu Ser
515 520 525

Ala Ala Ala Gly Asp Gly Phe Asn Thr Thr Ser Tyr Arg Ala Thr Met
530 535 540

Ser Pro Gly Gly Ser Leu Thr Ser Arg Asp Phe Gln Phe Leu Asp Leu
545 550 555 560

Asn Thr Ser Phe Thr Ser Asp Val Ala Ser Asn Leu Trp Leu His Phe
565 570 575

Ile Arg Tyr Ile Arg Pro Gly Asn Leu Tyr Ile Asp Arg Ala Glu Phe
580 585 590

Ile Pro Val Asp Ala Thr Phe Glu Ala Gly Tyr Asn Leu Glu Arg Ala
595 600 605

Gln Lys Ala Val Asn Ala Leu Phe Thr Ser Thr Asn Gln Lys Gly Leu
610 615 620

Gln Thr Asp Val Thr Asp Tyr His Ile Asp Gln Val Ser Asn Leu Val
625 630 635 640

-continued

```
Asp Cys Leu Ser Asp Glu Phe Cys Leu Asp Glu Lys Arg Glu Leu Ser
                645                 650                 655

Glu Lys Val Lys Gln Ala Lys Arg Leu Ser Asp Glu Arg Asn Leu Leu
            660                 665                 670

Gln Asp Ser Asn Phe Arg Gly Ile Asn Arg Glu Gln Asp Arg Gly Trp
        675                 680                 685

Arg Gly Ser Thr His Ile Thr Ile Gln Gly Gly Asn Asp Val Phe Lys
    690                 695                 700

Glu Asn Phe Val Thr Leu Pro Gly Ala Phe Asp Ala Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Asp Ile Tyr
            740                 745                 750

Leu Ile Arg Tyr Asn Thr Lys His Glu Thr Leu Asn Val Pro Gly Thr
        755                 760                 765

Lys Ser Pro Trp Ser Leu Cys Thr Glu Ser Pro Leu Gly Lys Cys Gly
    770                 775                 780

Glu Pro Asn Arg Cys Ala Ser Gln Ile Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asn Leu Gly
            820                 825                 830

Ile Trp Val Ile Phe Lys Ile Lys Thr Gln Asp Gly His Ala Arg Leu
        835                 840                 845

Gly Asn Leu Glu Phe Leu Glu Glu Lys Pro Leu Leu Gly Glu Ala Leu
    850                 855                 860

Ala Arg Val Lys Arg Ala Glu Lys Lys Trp Arg Asp Lys Arg Glu Lys
865                 870                 875                 880

Leu Gln Ser Glu Thr Asn Ile Val Tyr Lys Glu Ala Lys Glu Ala Val
                885                 890                 895

Asp Gly Leu Phe Val Asp Ser Gln Tyr Glu Arg Leu Gln Ala Asp Thr
            900                 905                 910

Asn Ile Ala Met Ile His Ala Ala Asp Lys His Val His Gln Ile Arg
        915                 920                 925

Glu Val Tyr Phe Pro Glu Leu Ser Val Ile Pro Gly Val Asn Ala Ala
    930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Val Gln Asn Asn His
            980                 985                 990

Arg Ser Val Leu Val Ile Ala Glu  Trp Glu Ala Glu Val  Ser Gln Glu
        995                 1000                1005

Val Pro  Val Cys Pro Gly Arg  Gly Tyr Ile Leu Arg  Val Thr Ala
    1010                1015                1020

Tyr Lys  Glu Gly Tyr Gly Glu  Gly Cys Val Thr Ile  His Glu Ile
    1025                1030                1035

Glu Asp  His Thr Asp Glu Leu  Lys Phe Arg Asn Cys  Glu Glu Glu
    1040                1045                1050

Glu Val  Tyr Pro Asn Asn Thr  Val Thr Cys Asn Gly  Tyr Thr Ala
```

```
    1055                1060                1065

Thr Gln  Glu Glu Tyr Lys Asp  Ala Tyr Thr Ser Arg  Asn Arg Gly
    1070                1075                1080

Tyr Asp  Glu Ala Tyr Gly Asn  Asn Pro Ser Val Pro  Ala Asp Tyr
    1085                1090                1095

Ala Ser  Val Tyr Glu Glu Lys  Ala Tyr Thr Asp Gly  Arg Arg Glu
    1100                1105                1110

Asn Pro  Cys Glu Met Glu Arg  Gly Tyr Thr Pro Leu  Pro Val Gly
    1115                1120                1125

Tyr Ile  Thr Lys Glu Leu Glu  Tyr Phe Pro Glu Thr  Asp Thr Val
    1130                1135                1140

Trp Ile  Glu Leu Gly Glu Thr  Glu Gly Thr Phe Leu  Ile Asp Ser
    1145                1150                1155

Val Glu  Leu Leu Leu Met Glu  Glu
    1160                1165


<210> SEQ ID NO 51
<211> LENGTH: 1161
<212> TYPE: PRT
<213> ORGANISM: Bacillus thuringiensis

<400> SEQUENCE: 51

Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255
```

```
Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Phe Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Ser Ser Ser Ser Val Ser Ile Ile Arg
        435                 440                 445

Ala Pro Met Phe Ser Trp Ile His Arg Ser Ala Glu Phe Asn Asn Ile
    450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510

Ile Glu Val Pro Ile His Phe Pro Ser Thr Ser Thr Arg Tyr Arg Val
        515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
```

```
        675                 680                 685

Phe Lys Asp Ile Asn Arg Gln Pro Glu Arg Gly Trp Gly Gly Ser Thr
    690                 695                 700

Gly Ile Thr Ile Gln Gly Val Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Val Tyr Leu Ile Arg Tyr
        755                 760                 765

Asn Ala Lys His Glu Thr Leu Asn Val Pro Gly Thr Gly Ser Leu Trp
    770                 775                 780

Pro Leu Ala Val Lys Ser Pro Ile Gly Arg Cys Gly Glu Pro Asn Arg
785                 790                 795                 800

Cys Ala His His Ser His His Phe Ser Leu Asp Ile Asp Val Gly Cys
                805                 810                 815

Thr Asp Leu Asn Glu Asp Leu Gly Val Trp Val Ile Phe Lys Ile Lys
            820                 825                 830

Thr Gln Asp Gly His Ala Lys Ile Gly Asn Leu Glu Phe Leu Glu Glu
        835                 840                 845

Lys Leu Leu Leu Gly Glu Ala Leu Ala Arg Val Lys Lys Ala Glu Lys
    850                 855                 860

Lys Trp Arg Asp Lys Arg Glu Lys Leu Glu Trp Glu Thr Asn Ile Val
865                 870                 875                 880

Tyr Lys Glu Ala Lys Glu Ser Val Asp Ala Leu Phe Val Asp Ser Gln
                885                 890                 895

Tyr Asn Arg Leu Gln Thr Asp Thr Asn Ile Ala Met Ile His Ala Ala
            900                 905                 910

Asp Lys Arg Val His Arg Ile Arg Glu Ala Tyr Leu Pro Glu Leu Ser
        915                 920                 925

Val Ile Pro Gly Val Asn Ala Ala Ile Phe Glu Glu Leu Glu Gly Leu
    930                 935                 940

Ile Phe Thr Ala Phe Ser Leu Tyr Asp Ala Arg Asn Val Ile Lys Asn
945                 950                 955                 960

Gly Asp Phe Asn Tyr Gly Leu Ser Cys Trp Asn Val Lys Gly His Val
                965                 970                 975

Asp Val Glu Glu Gln Asn Asn His Arg Ser Val Leu Val Ile Pro Glu
            980                 985                 990

Trp Glu Ala Glu Val Ser Gln Glu  Val Arg Val Cys Pro  Gly Arg Gly
        995                 1000                1005

Tyr Ile  Leu Arg Val Thr Ala  Tyr Lys Glu Gly Tyr  Gly Glu Gly
    1010                 1015                 1020

Cys Val  Thr Ile His Glu Ile  Glu Asp Asn Thr Asp  Glu Leu Lys
    1025                 1030                 1035

Phe Ser  Asn Cys Val Glu Glu  Glu Val Tyr Pro Asn  Asn Thr Val
    1040                 1045                 1050

Thr Cys  Asn Asp Tyr Thr Ala  Thr Gln Glu Glu Tyr  Glu Gly Thr
    1055                 1060                 1065

Tyr Thr  Ser Arg Asn Arg Gly  Tyr Asp Gly Ala Tyr  Glu Ser Asn
    1070                 1075                 1080

Ser Ser  Val Pro Ala Asp Tyr  Ala Ser Ala Tyr Glu  Glu Lys Ala
    1085                 1090                 1095
```

```
Tyr Thr  Asp Gly Arg Arg Asp  Asn Pro Cys Glu Ser  Asn Arg Gly
    1100                 1105                 1110

Tyr Arg  Asp Tyr Thr Pro Leu  Pro Ala Gly Tyr Val  Thr Lys Glu
    1115                 1120                 1125

Leu Glu  Tyr Phe Pro Glu Thr  Asp Lys Val Trp Ile  Glu Ile Gly
    1130                 1135                 1140

Glu Thr  Glu Gly Thr Phe Ile  Val Asp Ser Val Glu  Leu Leu Leu
    1145                 1150                 1155

Met Glu  Glu
    1160


<210> SEQ ID NO 52
<211> LENGTH: 1176
<212> TYPE: PRT
<213> ORGANISM: Bacillus thuringiensis

<400> SEQUENCE: 52

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Pro Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
```

```
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr Phe Glu Ala Glu Tyr Asp Leu Glu Arg Ala Gln Lys Ala Val Asn
    610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
    690                 695                 700

Ile Thr Ile Gln Gly Gly Asp Asp Val Phe Lys Glu Asn Tyr Val Thr
705                 710                 715                 720
```

```
Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
        755                 760                 765

Ala Lys His Glu Thr Val Asn Val Pro Gly Thr Gly Ser Leu Trp Pro
    770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
        835                 840                 845

Lys Ile Lys Thr Gln Asp Gly His Ala Arg Leu Gly Asn Leu Glu Phe
    850                 855                 860

Leu Glu Glu Lys Pro Leu Val Gly Glu Ala Leu Ala Arg Val Lys Arg
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln  Asn Asn Gln Arg Ser  Val Leu Val
        995                 1000                1005

Leu Pro  Glu Trp Glu Ala Glu  Val Ser Gln Glu Val  Arg Val Cys
    1010                1015                1020

Pro Gly  Arg Gly Tyr Ile Leu  Arg Val Thr Ala Tyr  Lys Glu Gly
    1025                1030                1035

Tyr Gly  Glu Gly Cys Val Thr  Ile His Glu Ile Glu  Asn Asn Thr
    1040                1045                1050

Asp Glu  Leu Lys Phe Ser Asn  Cys Val Glu Glu Glu  Ile Tyr Pro
    1055                1060                1065

Asn Asn  Thr Val Thr Cys Asn  Asp Tyr Thr Val Asn  Gln Glu Glu
    1070                1075                1080

Tyr Gly  Gly Ala Tyr Thr Ser  Arg Asn Arg Gly Tyr  Asn Glu Ala
    1085                1090                1095

Pro Ser  Val Pro Ala Asp Tyr  Ala Ser Val Tyr Glu  Glu Lys Ser
    1100                1105                1110

Tyr Thr  Asp Gly Arg Arg Glu  Asn Pro Cys Glu Phe  Asn Arg Gly
    1115                1120                1125
```

-continued

| | | | | | | | | | | | | | |
|---|---|---|---|---|---|---|---|---|---|---|---|---|---|
| Tyr | Arg | Asp | Tyr | Thr | Pro | Leu | Pro | Val | Gly | Tyr | Val | Thr | Lys | Glu |
| | 1130 | | | | | 1135 | | | | | 1140 | | | |
| Leu | Glu | Tyr | Phe | Pro | Glu | Thr | Asp | Lys | Val | Trp | Ile | Glu | Ile | Gly |
| | 1145 | | | | | 1150 | | | | | 1155 | | | |
| Glu | Thr | Glu | Gly | Thr | Phe | Ile | Val | Asp | Ser | Val | Glu | Leu | Leu | Leu |
| | 1160 | | | | | 1165 | | | | | 1170 | | | |
| Met | Glu | Glu | | | | | | | | | | | | |
| | 1175 | | | | | | | | | | | | | |